US008927692B2

(12) United States Patent
Weiner et al.

(10) Patent No.: US 8,927,692 B2
(45) Date of Patent: Jan. 6, 2015

(54) CONSENSUS PROSTATE ANTIGENS, NUCLEIC ACID MOLECULE ENCODING THE SAME AND VACCINE AND USES COMPRISING THE SAME

(75) Inventors: David B Weiner, Merion, PA (US); Jian Yan, Havertown, PA (US); Bernadette Ferraro, Philadelphia, PA (US); Niranjan Y Sardesai, Blue Bell, PA (US); Mathura P Ramanathan, Ardmore, PA (US)

(73) Assignees: The Trustees of the University of Pennsylvania, Philadelphia, PA (US); Inovio Pharmaceuticals, Inc., Plymouth Meeting, PA (US)

( * ) Notice: Subject to any disclaimer, the term of this patent is extended or adjusted under 35 U.S.C. 154(b) by 0 days.

(21) Appl. No.: 13/883,978

(22) PCT Filed: Nov. 14, 2011

(86) PCT No.: PCT/US2011/060592
§ 371 (c)(1),
(2), (4) Date: Jul. 29, 2013

(87) PCT Pub. No.: WO2012/065164
PCT Pub. Date: May 18, 2012

(65) Prior Publication Data
US 2013/0302361 A1 Nov. 14, 2013

Related U.S. Application Data

(60) Provisional application No. 61/413,176, filed on Nov. 12, 2010, provisional application No. 61/417,817, filed on Nov. 29, 2010.

(51) Int. Cl.
C07K 7/00 (2006.01)
A61K 39/00 (2006.01)
(52) U.S. Cl.
CPC .................................. A61K 39/0011 (2013.01)
USPC ........................................................ 530/350
(58) Field of Classification Search
None
See application file for complete search history.

(56) References Cited

U.S. PATENT DOCUMENTS

| | | | |
|---|---|---|---|
| 4,554,101 A | 11/1985 | Hopp | |
| 4,945,050 A | 7/1990 | Sanford et al. | |
| 5,036,006 A | 7/1991 | Sanford et al. | |
| 5,580,859 A | 12/1996 | Felgner et al. | |
| 5,593,972 A | 1/1997 | Weiner et al. | |
| 5,676,594 A | 10/1997 | Joosten | |
| 5,703,055 A | 12/1997 | Felgner et al. | |
| 5,739,118 A | 4/1998 | Carrano et al. | |
| 5,817,637 A | 10/1998 | Weiner et al. | |
| 5,830,876 A | 11/1998 | Weiner et al. | |
| 5,962,428 A | 10/1999 | Carrano et al. | |
| 5,981,505 A | 11/1999 | Weiner et al. | |
| 6,110,161 A | 8/2000 | Mathiesen et al. | |
| 6,261,281 B1 | 7/2001 | Mathiesen et al. | |
| 6,329,503 B1 * | 12/2001 | Afar et al. | 530/350 |
| 6,630,305 B1 * | 10/2003 | Xu et al. | 435/6.14 |
| 6,697,669 B2 | 2/2004 | Dev et al. | |
| 6,939,862 B2 | 9/2005 | Bureau et al. | |
| 6,958,060 B2 | 10/2005 | Mathiesen et al. | |
| 7,238,522 B2 | 7/2007 | Hebel et al. | |
| 7,245,963 B2 | 7/2007 | Draghia-Akli et al. | |
| 7,273,525 B2 | 9/2007 | Vaartstra | |
| 7,328,064 B2 | 2/2008 | Mathiesen et al. | |
| 2002/0081680 A1 | 6/2002 | Xu et al. | |
| 2005/0052630 A1 | 3/2005 | Smith et al. | |
| 2005/0266530 A1 | 12/2005 | Marshall et al. | |

FOREIGN PATENT DOCUMENTS

WO 93/24640 12/1993
WO 94/16737 8/1994

OTHER PUBLICATIONS

Haigh et al, Oncology vol. 13(11) p. 1561 (Nov. 1999).*
Liu, M.A. and J.B. Ulmer, Human clinical trials of plasmid DNA vaccines. Adv Genet, 2005. 55: p. 25-40.
Andre, S., et al., Increased immune response elicited by DNA vaccination with a synthetic gp120 sequence with optimized codon usage. J Virol, 1998. 72(2): p. 1497-1503.
Deml, L., et al., Multiple effects of codon usage optimization on expression and immunogenicity of DNA candidate 10 vaccines encoding the human immunodeficiency virus type 1 Gag protein. J Virol, 2001. 75(22): p. 10991-1001.
Laddy, D.J., et al., Immunogenicity of novel consensus-based DNA vaccines against avian influenza. Vaccine, 2007. 25(16): p. 2984-2989.
Frelin, L., et al., Codon optimization and mRNA amplification effectively enhances the immunogenicity of the hepatitis C virus nonstructural3/4A gene. Gene Ther, 2004. 11(6): p. 522-533.
Hirao, L.A., et al., Intradermal/subcutaneous immunization by electroporation improves plasmid vaccine delivery and potency in pigs and rhesus macaques. Vaccine, 2008. 26(3): p. 440-448.
Luckay, A., et al., Effect of plasmid DNA vaccine design and in vivo electroporation on the resulting vaccine-specific immune responses in rhesus macaques. J Virol, 2007. 81(10): p. 5257-5269.
Ahlen, G., et al., In vivo electroporation enhances the immunogenicity of hepatitis C virus nonstructural 3/4A DNA by increased local DNA uptake, protein expression, inflammation, and infiltration of CD3+ T cells. J Immunol, 2007. 179(7): p. 4741-4753.
Yan, J., et al., Enhanced cellular immune responses elicited by an engineered HIV-1 subtype B consensus-based envelope DNA vaccine. Mol Ther, 2007. 15(2): p. 411-421.
Rolland, M., et al., Reconstruction and function of ancestral center-of-tree human immunodeficiency virus type 1 proteins. J Virol, 2007. 81(16): p. 8507-8514.

* cited by examiner

*Primary Examiner* — Sheela J Huff
(74) *Attorney, Agent, or Firm* — Riverside Law LLP

(57) ABSTRACT

Provided herein are consensus amino acid sequences of prostate antigens that are capable of breaking tolerance in a targeted species, including PSA, PSMA, STEAP and PSCA antigens. Also provided are nucleic acid sequences that encode one or more consensus amino acid sequences of prostate antigens PSA, PSMA, STEAP and PSCA, as well genetic constructs/vectors and vaccines expressing the sequences. Also provided herein are methods for generating an autoimmune response against prostate cancer cells by administering one or more of the vaccines, proteins, and/or nucleic acid sequences that are provided.

3 Claims, 5 Drawing Sheets

Figures 3A, 3B and 3C    CD4+ T Cell Responses

Figures 4A, 4B and 4C CD8+ T Cell Responses

Figures 5A and 5B    PSA-Specific IgG Seroconversion

CONSENSUS PROSTATE ANTIGENS, NUCLEIC ACID MOLECULE ENCODING THE SAME AND VACCINE AND USES COMPRISING THE SAME

CROSS-REFERENCE TO RELATED APPLICATIONS

This application claims priority to and is a United States National Stage filing under 35 USC §371 of International PCT Application Serial No. PCT/US2011/060592, filed Nov. 14, 2011, which claims priority to U.S. Provisional Application Nos. 61/413,176, filed Nov. 12, 2010, and 61/417,817, filed Nov. 29, 2010, each of which is incorporated herein by reference in its entirety.

FIELD OF THE INVENTION

The present invention relates to nucleic acid sequences encoding consensus prostate proteins and fragments thereof; to improved prostate cancer vaccines, improved methods for inducing immune responses against prostate cancer cells, improved methods for prophylactically and/or therapeutically immunizing individuals against prostate cancer.

BACKGROUND OF THE INVENTION

Prostate cancer is an important therapeutic immune target. The development of an immune therapeutic approach is complex, in that immunogens need to be developed that are capable of inducing strong immune responses including preferably CTL responses.

The direct administration of nucleic acid sequences to vaccinate against animal and human diseases has been studied and much effort has focused on effective and efficient means of nucleic acid delivery in order to yield necessary expression of the desired antigens, resulting immunogenic response and ultimately the success of this technique.

DNA vaccines have many conceptual advantages over more traditional vaccination methods, such as live attenuated viruses and recombinant protein-based vaccines. DNA vaccines are safe, stable, easily produced, and well tolerated in humans with preclinical trials indicating little evidence of plasmid integration [Martin, T., et al., Plasmid DNA malaria vaccine: the potential for genomic integration after intramuscular injection. Hum Gene Ther, 1999. 10(5): p. 759-68; Nichols, W. W., et al., Potential DNA vaccine integration into host cell genome. Ann N Y Acad Sci, 1995. 772: p. 30-9]. In addition, DNA vaccines are well suited for repeated administration due to the fact that efficacy of the vaccine is not influenced by pre-existing antibody titers to the vector [Chattergoon, M., J. Boyer, and D. B. Weiner, Genetic immunization: a new era in vaccines and immune therapeutics. FASEB J, 1997. 11(10): p. 753-63]. However, one major obstacle for the clinical adoption of DNA vaccines has been a decrease in the platform's immunogenicity when moving to larger animals [Liu, M. A. and J. B. Ulmer, Human clinical trials of plasmid DNA vaccines. Adv Genet, 2005. 55: p. 25-40]. Recent technological advances in the engineering of DNA vaccine immunogen, such has codon optimization, RNA optimization and the addition of immunoglobulin leader sequences have improved expression and immunogenicity of DNA vaccines [Andre, S., et al., Increased immune response elicited by DNA vaccination with a synthetic gp120 sequence with optimized codon usage. J Virol, 1998. 72(2): p. 1497-503; Deml, L., et al., Multiple effects of codon usage optimization on expression and immunogenicity of DNA candidate vaccines encoding the human immunodeficiency virus type 1 Gag protein. J Virol, 2001. 75(22): p. 10991-1001; Laddy, D. J., et al., Immunogenicity of novel consensus-based DNA vaccines against avian influenza. Vaccine, 2007. 25(16): p. 2984-9; Frelin, L., et al., Codon optimization and mRNA amplification effectively enhances the immunogenicity of the hepatitis C virus nonstructural 3/4A gene. Gene Ther, 2004. 11(6): p. 522-33].

Recent technological advances in plasmid delivery systems have improved expression and immunogenicity of DNA vaccines including technologies such as electroporation [Hirao, L. A., et al., Intradermal/subcutaneous immunization by electroporation improves plasmid vaccine delivery and potency in pigs and rhesus macaques. Vaccine, 2008. 26(3): p. 440-8; Luckay, A., et al., Effect of plasmid DNA vaccine design and in vivo electroporation on the resulting vaccine-specific immune responses in rhesus macaques. J Virol, 2007. 81(10): p. 5257-69; Ahlen, G., et al., In vivo electroporation enhances the immunogenicity of hepatitis C virus nonstructural 3/4A DNA by increased local DNA uptake, protein expression, inflammation, and infiltration of CD3+ T cells. J Immunol, 2007. 179(7): p. 4741-53].

In addition, studies have suggested that the use of consensus immunogens can be able to increase the breadth of the cellular immune response as compared to native antigens alone [Yan, J., et al., Enhanced cellular immune responses elicited by an engineered HIV-1 subtype B consensus-based envelope DNA vaccine. Mol Ther, 2007. 15(2): p. 411-21; Rolland, M., et al., Reconstruction and function of ancestral center-of-tree human immunodeficiency virus type 1 proteins. J Virol, 2007. 81(16): p. 8507-14]. However, it is recognized that breaking immune tolerance for cancer antigens and generating autoimmunity is a major obstacle for cancer vaccines.

There still remains a need for nucleic acid constructs that encode prostate cancer antigens and for compositions useful to induce immune responses against prostate cancer antigens and thus break immune tolerance. There remains a need for effective prophylactic and therapeutic vaccines against prostate cancer that are economical and effective.

SUMMARY OF THE PREFERRED EMBODIMENTS

Aspects of the present invention include nucleic acid molecules comprising a coding sequence encoding one or more proteins selected from the group comprising: a) SEQ ID NO:2; a protein that is 98% homologous to SEQ ID NO:2, provided amino acids 69, 78, 80, 82, 102, 110, 137, 139, 165, 189, 203, 220, 232 and 248 of SEQ ID NO:2 are conserved; or an immunogenic fragment of SEQ ID NO:2 comprising amino acids corresponding to at least 256 amino acid residues of SEQ ID NO:2, provided amino acids 69, 78, 80, 82, 102, 110, 137, 139, 165, 189, 203, 220, 232 and 248 of SEQ ID NO:2 are conserved; b) SEQ ID NO:4; a protein that is 98% homologous to SEQ ID NO:4, provided amino acids 21, 86, 127, 129, 154, 156, 182, 195, 206, 218, 220, 237, 249, 255, 265, 271 and 275 of SEQ ID NO:4 are conserved; or an immunogenic fragment of SEQ ID NO:4 comprising amino acids corresponding to at least 274 amino acid residues of SEQ ID NO:4, provided amino acids 21, 86, 127, 129, 154, 156, 182, 195, 206, 218, 220, 237, 249, 255, 265, 271 and 275 of SEQ ID NO:4 are conserved; c) SEQ ID NO:6; a protein that is 98% homologous to SEQ ID NO:6, provided amino acids 14, 15, 32, 47, 58, 79, 111, 157, 223, 320, 350, 475, 499, 569, 613, 624, 653, 660, 663, 733 and 734 of SEQ ID NO:6 are conserved; or an immunogenic fragment of SEQ ID NO:6 comprising amino acids corresponding to at least 735 amino acid residues of SEQ ID NO:6, provided amino acids 14, 15, 32, 47, 58, 79, 111, 157, 223, 320, 350, 475, 499, 569, 613, 624, 653, 660, 663, 733 and 734 of SEQ ID NO:6 are conserved; d) SEQ ID NO:8; a protein that is 98% homologous to SEQ ID NO:8, provided amino acids 21, 31, 32, 49, 64, 75, 96, 128, 174, 240, 337, 367, 492, 516, 565, 586, 630, 641, 670, 677, 680, 750, and 751 of SEQ ID NO:8 are conserved; or an immunogenic fragment of SEQ ID NO:8 comprising amino acids corresponding to at least 752 amino acid residues of SEQ ID NO:8, provided amino acids 21, 31, 32, 49, 64, 75, 96, 128, 174, 240, 337, 367, 492, 516, 565, 586, 630, 641, 670, 677, 680, 750, and 751 of SEQ ID NO:8 are conserved; e) SEQ ID NO:10; a protein that is 98% homologous to SEQ ID NO:10; or an immunogenic fragment of SEQ ID NO:10 comprising amino acids corresponding to at least 333 amino acid residues of SEQ ID NO:10; f) SEQ ID NO:12; a protein that is 98% homologous to SEQ ID NO:12; or an immunogenic fragment of SEQ ID NO:12 comprising amino acids corresponding to at least 349 amino acid residues of SEQ ID NO:12; g) SEQ ID NO:14; a protein that is 98% homologous to SEQ ID NO:14 or an immunogenic fragment of SEQ ID NO:14 comprising amino acids corresponding to at least 129 amino acid residues of SEQ ID NO:14; or h) a signal peptide linked to amino acids 19-131 of SEQ ID NO:14; a protein that has a signal peptide linked to an amino acid sequence that is 98% homologous to amino acids 19-131 of SEQ ID NO:14; or protein that has a signal peptide linked to an immunogenic fragment of amino acids 19-131 of SEQ ID NO:14, the fragment comprising at least 110 amino acid residues of SEQ ID NO:14 and linked to a signal peptide. In some embodiments the nucleic acid molecules are chosen from ones encoding proteins a), b), c), or d).

In another aspect, the invention includes methods of treating an individual who has been diagnosed with prostate cancer comprising administering a nucleic acid molecule described herein to an individual.

In another aspect, there are provided proteins selected from the group consisting of: a) SEQ ID NO:2; a protein that is 98% homologous to SEQ ID NO:2, provided amino acids 69, 78, 80, 82, 102, 110, 137, 139, 165, 189, 203, 220, 232 and 248 of SEQ ID NO:2 are conserved; or an immunogenic fragment of SEQ ID NO:2 comprising amino acids corresponding to at least 261 amino acid residues of SEQ ID NO:2, provided amino acids 69, 78, 80, 82, 102, 110, 137, 139, 165, 189, 203, 220, 232 and 248 of SEQ ID NO:2 are conserved; b) SEQ ID NO:4; a protein that is 98% homologous to SEQ ID NO:4, provided amino acids 21, 86, 127, 129, 154, 156, 182, 195, 206, 218, 220, 237, 249, 255, 265, 271 and 275 of SEQ ID NO:4 are conserved; or an immunogenic fragment of SEQ ID NO:4 comprising amino acids corresponding to at least 274 amino acid residues of SEQ ID NO:4, provided amino acids 21, 86, 127, 129, 154, 156, 182, 195, 206, 218, 220, 237, 249, 255, 265, 271 and 275 of SEQ ID NO:4 are conserved; c) SEQ ID NO:6; a protein that is 98% homologous to SEQ ID NO:6, provided amino acids 14, 15, 32, 47, 58, 79, 111, 157, 223, 320, 350, 475, 499, 569, 613, 624, 653, 660, 663, 733 and 734 of SEQ ID NO:6 are conserved; or an immunogenic fragment of SEQ ID NO:6 comprising amino acids corresponding to at least 735 amino acid residues of SEQ ID NO:6, provided amino acids 14, 15, 32, 47, 58, 79, 111, 157, 223, 320, 350, 475, 499, 569, 613, 624, 653, 660, 663, 733 and 734 of SEQ ID NO:6 are conserved; d) SEQ ID NO:8; a protein that is 98% homologous to SEQ ID NO:8, provided amino acids 21, 31, 32, 49, 64, 75, 96, 128, 174, 240, 337, 367, 492, 516, 565, 586, 630, 641, 670, 677, 680, 750, and 751 of SEQ ID NO:8 are conserved; or an immunogenic fragment of SEQ ID NO:8 comprising amino acids corresponding to at least 752 amino acid residues of SEQ ID NO:8, provided amino acids 21, 31, 32, 49, 64, 75, 96, 128, 174, 240, 337, 367, 492, 516, 565, 586, 630. 641, 670, 677, 680, 750, and 751 of SEQ ID NO:8 are conserved; e) SEQ ID NO:10; a protein that is 98% homologous to SEQ ID NO:10; or an immunogenic fragment of SEQ ID NO:10 comprising amino acids corresponding to at least 333 amino acid residues of SEQ ID NO:10; f) SEQ ID NO:12; a protein that is 98% homologous to SEQ ID NO:12; or an immunogenic fragment of SEQ ID NO:12 comprising amino acids corresponding to at least 349 amino acid residues of SEQ ID NO:12; g) SEQ ID NO:14; a protein that is 98% homologous to SEQ ID NO:14; or an immunogenic fragment of SEQ ID NO:14 comprising amino acids corresponding to at least 129 amino acid residues of SEQ ID NO:14; or h) a signal peptide linked to amino acids 19-131 of SEQ ID NO:14; a protein that has a signal peptide linked to an amino acid sequence that is 98% homologous to amino acids 19-131 of SEQ ID NO:14; or protein that has a signal peptide linked to an immunogenic fragment of amino acids 19-131 of SEQ ID NO:14, the fragment comprising at least 110 amino acid residues of SEQ ID NO:14 and linked to a signal peptide. In some embodiments, the protein is selected from the group comprising: proteins a), b), c), or d).

Some aspects of the invention include methods of treating an individual who has been diagnosed with prostate cancer comprising delivering to said individual a protein described herein.

Other aspects of the invention are pharmaceutical compositions comprising the nucleic acid molecules provided herein and a pharmaceutically acceptable excipient.

BRIEF DESCRIPTION OF THE FIGURES

(FIG. 5A) PSA IgG endpoint titers. (FIG. 5B) Representative IgG titration curves.

DETAILED DESCRIPTION

Figure 1:
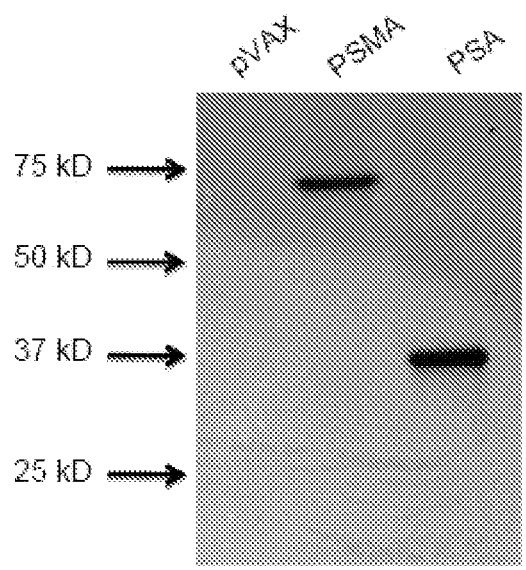
FIG. 1 shows results from in vitro translation performed to confirm the expression of the PSA and PSMA antigens.

Provided herein are consensus sequence prostate proteins and isolated nucleic acid molecules that encode them, and in particular, the prostate antigens prostate specific antigen (PSA), prostate specific membrane antigen (PSMA), sixtransmembrane epithelial antigen of the prostate antigen (STEAP) and prostate specific stem cell antigen (PSCA).

The prostate cancer antigens described herein are consensus sequences derived from a pool of homologous antigens from across multiple species, including the specie that the vaccine is targeted for. The selected species from which antigen sequences are aligned to form a consensus shall be chosen based on close proximity of the species on a phylogenic tree, e.g., *H. sapiens* (humans), *M. mulatta* (rhesus macaques), and *M. fascicularis* (cynomolgus monkey). The consensus antigen is not identical to the native prostate antigen but will have close identity, which sequences share at least 85%, and preferably 90%, 91%, 92%, 93%, 94%, 95%, 96%, 97%, 98%, or 99% identity. These described consensus cancer antigens are able to break tolerance in the targeted specie (or cause autoimmunity) and generate an effective immune response against the prostate cancer antigen. Provided herein are methods to generate a consensus cancer antigen based DNA vaccine.

Aspects of the present invention include nucleic acid molecules comprising a coding sequence encoding one or more proteins selected from the group comprising: a) SEQ ID NO:2; a protein that is 98% homologous to SEQ ID NO:2, provided amino acids 69, 78, 80, 82, 102, 110, 137, 139, 165, 189, 203, 220, 232 and 248 of SEQ ID NO:2 are conserved; or an immunogenic fragment of SEQ ID NO:2 comprising amino acids corresponding to at least 256 amino acid residues of SEQ ID NO:2, provided amino acids 69, 78, 80, 82, 102, 110, 137, 139, 165, 189, 203, 220, 232 and 248 of SEQ ID NO:2 are conserved; b) SEQ ID NO:4; a protein that is 98% homologous to SEQ ID NO:4, provided amino acids 21, 86, 127, 129, 154, 156, 182, 195, 206, 218, 220, 237, 249, 255, 265, 271 and 275 of SEQ ID NO:4 are conserved; or an immunogenic fragment of SEQ ID NO:4 comprising amino acids corresponding to at least 274 amino acid residues of SEQ ID NO:4, provided amino acids 21, 86, 127, 129, 154, 156, 182, 195, 206, 218, 220, 237, 249, 255, 265, 271 and 275 of SEQ ID NO:4 are conserved; c) SEQ ID NO:6; a protein that is 98% homologous to SEQ ID NO:6, provided amino acids 14, 15, 32, 47, 58, 79, 111, 157, 223, 320, 350, 475, 499, 569, 613, 624, 653, 660, 663, 733 and 734 of SEQ ID NO:6 are conserved; or an immunogenic fragment of SEQ ID NO:6 comprising amino acids corresponding to at least 735 amino acid residues of SEQ ID NO:6, provided amino acids 14, 15, 32, 47, 58, 79, 111, 157, 223, 320, 350, 475, 499, 569, 613, 624, 653, 660, 663, 733 and 734 of SEQ ID NO:6 are conserved; d) SEQ ID NO:8; a protein that is 98% homologous to SEQ ID NO:8, provided amino acids 21, 31, 32, 49, 64, 75, 96, 128, 174, 240, 337, 367, 492, 516, 565, 586, 630, 641, 670, 677, 680, 750, and 751 of SEQ ID NO:8 are conserved; or an immunogenic fragment of SEQ ID NO:8 comprising amino acids corresponding to at least 752 amino acid residues of SEQ ID NO:8, provided amino acids 21, 31, 32, 49, 64, 75, 96, 128, 174, 240, 337, 367, 492, 516, 565, 586, 630. 641, 670, 677, 680, 750, and 751 of SEQ ID NO:8 are conserved; e) SEQ ID NO:10; a protein that is 98% homologous to SEQ ID NO:10; or an immunogenic fragment of SEQ ID NO:10 comprising amino acids corresponding to at least 333 amino acid residues of SEQ ID NO:10; f) SEQ ID NO:12; a protein that is 98% homologous to SEQ ID NO:12; or an immunogenic fragment of SEQ ID NO:12 comprising amino acids corresponding to at least 349 amino acid residues of SEQ ID NO:12; g) SEQ ID NO:14; a protein that is 98% homologous to SEQ ID NO:14; or an immunogenic fragment of SEQ ID NO:14 comprising amino acids corresponding to at least 129 amino acid residues of SEQ ID NO:14; or an immunogenic fragment of SEQ ID NO:14 comprising at least 129 amino acid residues of SEQ ID NO:14; or h) a signal peptide linked to amino acids 19-131 of SEQ ID NO:14; a protein that has a signal peptide linked to an amino acid sequence that is 98% homologous to amino acids 19-131 of SEQ ID NO:14; or protein that has a signal peptide linked to an immunogenic fragment of amino acids 19-131 of SEQ ID NO:14, the fragment comprising at least 110 amino acid residues of SEQ ID NO:14 and linked to a signal peptide. Two consensus protein sequences for PSA are disclosed: PSA Consensus Antigen sequence 1 (SEQ ID NO:2) and PSA Consensus Antigen sequence 2 (SEQ ID NO:4). Two consensus protein sequences for PSMA are disclosed: PSMA Consensus Antigen sequence 1 (SEQ ID NO:6) and PSMA Consensus Antigen sequence 2 (SEQ ID N0:8). Two consensus protein sequences for STEAP (also referred to herein as STEAP1) are disclosed: STEAP Consensus Antigen sequence 1 (SEQ ID NO:10) and STEAP Consensus Antigen sequence 2 (SEQ ID NO:12). One consensus protein sequence for PSCA is disclosed: PSCA Consensus Antigen sequence (SEQ ID NO:14). SEQ ID NO:14 includes an IgE signal peptide. In some embodiments, a PSCA Consensus antigen may include amino acids 19-131 of SEQ ID NO:14 linked to a signal sequence other than the IgE signal in SEQ ID NO:14. In some embodiments the nucleic acid molecules are chosen from ones encoding proteins a), b), c), or d), above. In other embodiments the nucleic acid molecules are ones encoding one or more proteins selected from the group comprising: at least one selected from ones encoding either proteins a) or b), and at least one selected from ones encoding either proteins c) or d).

The nucleic acid molecules can further be molecules encoding one or more proteins selected from the group comprising: SEQ ID NO:2; SEQ ID NO:4; SEQ ID NO:6; SEQ ID NO:8; SEQ ID NO:10; SEQ ID NO:12; or SEQ ID NO:14; and preferably, SEQ ID NO:2; SEQ ID NO:4; SEQ ID NO:6; or SEQ ID NO:8. In some embodiments, the nucleic acid molecule of can be ones that encode one or more proteins selected from the group comprising: at least one selected from either SEQ ID NO:2 or SEQ ID NO:4, and at least one selected from either SEQ ID NO:6 or SEQ ID NO:8.

In another aspect, there are provided proteins selected from the group consisting of: a) SEQ ID NO:2; a protein that is 98% homologous to SEQ ID NO:2, provided amino acids 69, 78, 80, 82, 102, 110, 137, 139, 165, 189, 203, 220, 232 and 248 of SEQ ID NO:2 are conserved; or an immunogenic fragment of SEQ ID NO:2 comprising amino acids corresponding to at least 256 amino acid residues of SEQ ID NO:2, provided amino acids 69, 78, 80, 82, 102, 110, 137, 139, 165, 189, 203, 220, 232 and 248 of SEQ ID NO:2 are conserved; b) SEQ ID NO:4; a protein that is 98% homologous to SEQ ID NO:4, provided amino acids 21, 86, 127, 129, 154, 156, 182, 195, 206, 218, 220, 237, 249, 255, 265, 271 and 275 of SEQ ID NO:4 are conserved; or an immunogenic fragment of SEQ ID NO:4 comprising amino acids corresponding to at least 274 amino acid residues of SEQ ID NO:4, provided amino acids 21, 86, 127, 129, 154, 156, 182, 195, 206, 218, 220, 237, 249, 255, 265, 271 and 275 of SEQ ID NO:4 are conserved; c) SEQ ID NO:6; a protein that is 98% homologous to SEQ ID NO:6, provided amino acids 14, 15, 32, 47, 58, 79, 111, 157, 223, 320, 350, 475, 499, 569, 613, 624, 653, 660, 663, 733 and 734 of SEQ ID NO:6 are conserved; or an immunogenic fragment of SEQ ID NO:6 comprising amino acids corresponding to at least 735 amino acid residues of SEQ ID NO:6, provided amino acids 14, 15, 32, 47, 58, 79, 111, 157, 223, 320, 350, 475, 499, 569, 613, 624, 653, 660, 663, 733 and 734 of SEQ ID NO:6 are conserved; d) SEQ ID NO:8; a protein that is 98% homologous to SEQ ID NO:8, provided amino acids 21, 31, 32, 49, 64, 75, 96, 128, 174, 240, 337, 367, 492, 516, 565, 586, 630, 641, 670, 677, 680, 750, and 751 of SEQ ID NO:8 are conserved; or an immunogenic fragment of SEQ ID NO:8 comprising amino acids corresponding to at least 752 amino acid residues of SEQ ID NO:8, provided amino acids 21, 31, 32, 49, 64, 75, 96, 128, 174, 240, 337, 367, 492, 516, 565, 586, 630, 641, 670, 677, 680, 750, and 751 of SEQ ID NO:8 are conserved; e) SEQ ID NO:10; a protein that is 98% homologous to SEQ ID NO:10; or an immunogenic fragment of SEQ ID NO:10 comprising amino acids corresponding to at least 333 amino acid residues of SEQ ID NO:10; f) SEQ ID NO:12; a protein that is 98% homologous to SEQ ID NO:12; or an immunogenic fragment of SEQ ID NO:12 comprising amino acids corresponding to at least 349 amino acid residues of SEQ ID NO:12; g) SEQ ID NO:14; a protein that is 98% homologous to SEQ ID NO:14; or an immunogenic fragment of SEQ ID NO:14 comprising amino acids corresponding to at least 129 amino acid residues of SEQ ID NO:14; or h) a signal peptide linked to amino acids 19-131 of SEQ ID NO:14; a protein that has a signal peptide linked to an amino acid sequence that is 98% homologous to amino acids 19-131 of SEQ ID NO:14; or protein that has a signal peptide linked to an immunogenic fragment of amino acids 19-131 of SEQ ID NO:14, the fragment comprising at least 110 amino acid residues of SEQ ID NO:14 and linked to a signal peptide. In some embodiments, the protein is selected from the group comprising: proteins a), b), c), or d). In other embodiments the proteins are ones encoding one or more proteins selected from the group comprising: at least one selected from either proteins a) or b), and at least one selected from either proteins c) or d).

The proteins can further be proteins selected from the group comprising: SEQ ID NO:2; SEQ ID NO:4; SEQ ID NO:6; SEQ ID NO:8; SEQ ID NO:10; SEQ ID NO:12; or SEQ ID NO:14; and preferably, SEQ ID NO:2; SEQ ID NO:4; SEQ ID NO:6; or SEQ ID NO:8. In some embodiments, the proteins can be ones selected from the group comprising: at least one selected from either SEQ ID NO:2 or SEQ ID NO:4, and at least one selected from either SEQ ID NO:6 or SEQ ID NO:8.

Nucleic acid coding sequences have been generated to improve and optimize expression. The codons used in these nucleic acid molecules were selected to generate RNA having reduced secondary structure formation due to intramolecular hybridization. Nucleic acid sequences encoding PSA Consensus Antigen sequence 1 (SEQ ID NO:1) and PSA Consensus Antigen sequence 2 (SEQ ID NO:3) are disclosed. Likewise, nucleic acid coding sequence for PSMA Consensus Antigen sequence 1 (SEQ ID NO:5 of nucleotides 1-2250 of SEQ ID NO:5) and PSMA Consensus Antigen sequence 2 (SEQ ID NO:7 or nucleotides 1-2301 of SEQ ID NO:7) as well as STEAP Consensus Antigen sequence 1 (SEQ ID NO:9), STEAP Consensus Antigen sequence 2 (SEQ ID NO:11) and PSCA Consensus Antigen sequence (SEQ ID NO:13) are provided. Also provides are nucleic acid sequences that are 98% homologous to SEQ ID NO:1 and encode either PSA Consensus Antigen sequence 1 (SEQ ID NO:2) or a protein up to 98% homologous to SEQ ID NO:2, preferably including amino acids 69, 78, 80, 82, 102, 110, 137, 139, 165, 189, 203, 220, 232 and 248 of SEQ ID NO:2, and nucleic acid sequences that are 98% homologous to SEQ ID NO:3 and encode either PSA Consensus Antigen sequence 2 (SEQ ID NO:4) or a protein up to 98% homologous to SEQ ID NO:4, preferably including amino acids 21, 86, 127, 129, 154, 156, 182, 195, 206, 218, 220, 237, 249, 255, 265, 271 and 275 of SEQ ID NO:4. Likewise, nucleic acid sequences that are 98% homologous to nucleotides 2250 of SEQ ID NO:5 and encode either PSMA Consensus Antigen sequence 1 (SEQ ID NO:6) or a protein up to 98% homologous to SEQ ID NO:6, preferably including amino acids 14, 15, 32, 47, 58, 79, 111, 157, 223, 320, 350, 475, 499, 569, 613, 624, 653, 660, 663, 733 and 734 of SEQ ID NO:6, or nucleic acid sequences that are 98% homologous to nucleotides 2301 of SEQ ID NO:7 and encode either PSMA Consensus Antigen sequence 1 (SEQ ID NO:8) or a protein up to 98% homologous to SEQ ID NO:8, preferably including amino acids 21, 31, 32, 49, 64, 75, 96, 128, 174, 240, 337, 367, 492, 516, 565, 586, 630, 641, 670, 677, 680, 750, and 751 of SEQ ID NO:8 as well as nucleotides 98% homologous to SEQ ID NO 9 and encode either STEAP Consensus Antigen sequence 1 (SEQ ID NO: 10) or a protein that is up to 98% homologous to SEQ ID NO:10, nucleotides 98% homologous to SEQ ID NO:11 and encode either STEAP Consensus Antigen sequence 2 (SEQ ID NO:12) or a protein that is up to 98% homologous to SEQ ID NO:12, and nucleotides 98% homologous to SEQ ID NO:13 and encodes with PSCA Consensus Antigen sequence (SEQ ID NO:14) or a protein that is up to 98% homologous to SEQ ID NO: 14. In some embodiments nucleic acid molecules encode a protein that comprises an IgE signal peptide (for example, SEQ ID NO:3 which encodes SEQ ID NO:4; nucleotides 1-2301 of SEQ ID NO:7 which encodes SEQ ID NO:8; SEQ ID NO:11 which encodes SEQ ID NO:12, and SEQ ID NO:13 which encodes SEQ ID NO:14).

Compositions comprising nucleic acid molecules which comprise the coding sequences of the isolated nucleic acid molecules provided herein may be useful for inducing immune responses against a prostate protein when administered into an animal. Compositions containing one or more of these nucleic acid sequences may be used as vaccines or vaccine components to prophylactically or therapeutically immunize against prostate cancer. Likewise, compositions comprising consensus proteins may be useful for inducing immune responses against a prostate protein when administered into an animal. Combinations of compositions comprising nucleic acid molecules which comprise the coding sequences of the isolated nucleic acid molecules provided herein may be useful to induce immune responses against a prostate protein and may collectively be used as vaccines or vaccine components to prophylactically or therapeutically immunize against prostate cancer. Likewise, compositions comprising consensus proteins may be useful for inducing immune responses against a prostate protein when administered into an animal. Compositions containing one or more of these consensus proteins may be used as vaccines or vaccine components to prophylactically or therapeutically immunize against prostate cancer.

Vaccines are provided which comprises nucleic acid sequences provided herein. In some embodiments, vaccines are provided which comprises nucleic acid sequences encoding one or more consensus prostate antigens selected from the group consisting of: consensus PSA antigen 1, consensus PSA antigen 2, consensus PSMA antigen 1, consensus PSMA antigen 2, consensus STEAP antigen 1, consensus STEAP antigen 2, and consensus PSCA. Methods of inducing immune responses using nucleic acid sequences encoding one or more prostate antigens selected from the group consisting of: consensus PSA antigen 1, consensus PSA antigen 2, consensus PSMA antigen 1, consensus PSMA antigen 2, consensus STEAP antigen 1, consensus STEAP antigen 2, and consensus PSCA.

Vaccines which comprise one or more of consensus PSA antigen 1, consensus PSA antigen 2, consensus PSMA antigen 1, consensus PSMA antigen 2, consensus STEAP antigen 1, consensus STEAP antigen 2, and consensus PSCA are provided. Methods of inducing immune responses using one or more of consensus PSA antigen 1, consensus PSA antigen 2, consensus PSMA antigen 1, consensus PSMA antigen 2, consensus STEAP antigen 1, consensus STEAP antigen 2, and consensus PSCA are also provided.

Methods of protecting an individual against prostate cancer or of treating an individual who has been identified as having prostate cancer are provided. The methods comprise the step of: administering to said individual an effective amount of one or more nucleic acid molecules comprising one or more nucleic acid sequences provided herein. In some methods, the delivery of the nucleic acid molecules is facilitated by electroporation of the targeted tissue or the tissue that receives the nucleic acid molecules. The nucleic acid sequence is expressed in cells of the individual and an immune response is induced against the prostate protein encoded by the nucleic acid sequence.

1. DEFINITIONS

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6, 9, and 7.0 are explicitly contemplated.

a. Adjuvant

"Adjuvant" as used herein means any molecule added to the DNA plasmid vaccines described herein to enhance the immunogenicity of the antigens encoded by the DNA plasmids and the encoding nucleic acid sequences described hereinafter.

b. Antibody "Antibody" as used herein means an antibody of classes IgG, IgM, IgA, IgD or IgE, or fragments, fragments or derivatives thereof, including Fab, F(ab')2, Fd, and single chain antibodies, diabodies, bispecific antibodies, bifunctional antibodies and derivatives thereof. The antibody can be an antibody isolated from the serum sample of mammal, a polyclonal antibody, affinity purified antibody, or mixtures thereof which exhibits sufficient binding specificity to a desired epitope or a sequence derived therefrom.

c. Coding Sequence

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to whom the nucleic acid is administered.

d. Complement

"Complement" or "complementary" as used herein means a nucleic acid can mean Watson-Crick (e.g., A-T/U and C-G) or Hoogsteen base pairing between nucleotides or nucleotide analogs of nucleic acid molecules.

e. Consensus or Consensus Sequence

"Consensus" or "consensus sequence" as used herein means a polypeptide sequence based on analysis of an alignment of multiple subtypes of a particular prostate antigen. Nucleic acid sequences that encode a consensus polypeptide sequence may be prepared. Vaccines comprising proteins that comprise consensus sequences and/or nucleic acid molecules that encode such proteins can be used to induce broad immunity against a particular prostate antigen.

f. Electroporation

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

g. Fragment

"Fragment" as used herein with respect to nucleic acid sequences means a nucleic acid sequence or a portion thereof, that encodes a polypeptide capable of eliciting an immune response in a mammal that cross reacts with a full length prostate antigen. The fragments can be DNA fragments selected from at least one of the various nucleotide sequences that encode the consensus amino acid sequences and constructs comprising such sequences. DNA fragments can comprise coding sequences for the immunoglobulin leader such as IgE or IgG sequences. DNA fragments can encode the protein fragments set forth below.

"Fragment" with respect to polypeptide sequences means a polypeptide capable of eliciting an immune response in a mammal that cross reacts with a prostate antigen, including, e.g. PSA, PSMA, STEAP and PSCA.

The human PSMA sequence is about 749-750 amino acids. Fragments of PSMA consensus antigen 1 may comprise at least 90%, 91%, 92%, 93%, 94%, 95%, 96%, 97%, 98%, or 99% of SEQ ID NO:6, and preferably 98% or 99%, provided the fragments include one or more of amino acids 14, 15, 32, 47, 58, 79, 111, 157, 223, 320, 350, 475, 499, 569, 613, 624, 653, 660, 663, 733 and 734. Fragments of PSMA consensus antigen 1 may comprise 745, 746, 747, 748 or 749 amino acids of SEQ ID NO:6, but preferably 735 amino acids or more. Fragments of PSMA consensus antigen 2 may comprise at least 90%, 91%, 92%, 93%, 94%, 95%, 96%, 97%, 98%, or 99% of SEQ ID NO:8, and preferably 98% or 99%, provided the fragments include one or more of amino acids 20, 30, 31, 48, 63, 74, 95, 127, 173, 239, 336, 366, 491, 515, 564, 585, 629, 640, 669, 676, 679, 749 and 750. All such fragments of PSMA consensus antigen 2 may also optionally exclude amino acids 1-16. In some embodiments, fragments of PSMA consensus antigen 2 may optionally comprise one or more of amino acids 1-16 and of the amino acids from amino acid 17 to amino acid 766, fragments of PSMA consensus antigen 2 may also comprise 760, 761, 762, 763, 764 or 765 amino acids of SEQ ID NO:8, but preferably 751 amino acids or more.

The human PSMA sequence is about 749-750 amino acids. Fragments of PSMA consensus antigen 1 may comprise at least 90%, 91%, 92%, 93%, 94%, 95%, 96%, 97%, 98%, or 99% of SEQ ID NO:6, and preferably 98% or 99%, provided the fragments include one or more of amino acids 14, 15, 32, 47, 58, 79, 111, 157, 223, 320, 350, 475, 499, 569, 613, 624, 653, 660, 663, 733 and 734. Fragments of PSMA consensus antigen 1 may comprise 745, 746, 747, 748 or 749 amino acids of SEQ ID NO:6, but preferably 735 amino acids or more. Fragments of PSMA consensus antigen 2 may comprise at least 90%, 91%, 92%, 93%, 94%, 95%, 96%, 97%, 98%, or 99% of SEQ ID NO:8, and preferably 98% or 99%, provided the fragments include one or more of amino acids 20, 30, 31, 48, 63, 74, 95, 127, 173, 239, 336, 366, 491, 515, 564, 585, 629, 640, 669, 676, 679, 749 and 750. All such fragments of PSA consensus antigen 2 may also optionally exclude amino acids 1-16. In some embodiments, fragments of PSA consensus antigen 2 may optionally comprise one or more of amino acids 1-16 and of the amino acids from amino acid 17 to amino acid 766, fragments of PSMA consensus antigen 2 may also comprise 760, 761, 762, 763, 764 or 765 amino acids of SEQ ID NO:8, but preferably 751 amino acids or more.

The human STEAP sequence is about 339 amino acids. Consensus STEAP sequences may comprise amino acid sequences for the immunoglobulin leader such as IgE or IgG. Consensus STEAP antigen 2 contains an 18 amino acid leader sequence in place of the methionine at position 1. Fragments of STEAP consensus antigen 2 may comprise a leader sequence and at least 90%, 91%, 92%, 93%, 94%, 95%, 96%, 97%, 98%, or 99% of amino acids 18-356 of SEQ ID NO:12, and preferably 98% or 99%. Fragments of STEAP consensus antigen 1 may comprise amino acids 1-350, 1-351, 1-352, 1-353, 1-354 or 1-355 of SEQ ID NO:12.

The human PSCA sequence is about 114 amino acids. Consensus PSCA sequences may comprise amino acid sequences for the immunoglobulin leader such as IgE or IgG. Consensus PSCA antigen contains an 18 amino acid leader sequence in place of the methionine at position 1. Fragments of PSCA consensus antigen may comprise a leader sequence and at least 90%, 91%, 92%, 93%, 94%, 95%, 96%, 97%, 98%, or 99% of amino acids 18-131 of SEQ ID NO:14, and preferably 98% or 99%. Fragments of PSCA consensus antigen 1 may comprise amino acids 1-125, 1-126, 1-127, 1-128, 1-129 or 1-130 of SEQ ID NO:14.

h. Genetic Construct

As used herein, the term "genetic construct" refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

i. Homology

Homology of multiple sequence alignments and phylogram were generated using ClustalW, a general purpose multiple sequence alignment program for DNA or proteins.

j. Identical

"Identical" or "identity" as used herein in the context of two or more nucleic acids or polypeptide sequences, means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

k. Immune Response

"Immune response" as used herein means the activation of a host's immune system, e.g., that of a mammal, in response to the introduction of antigen such as a prostate consensus antigen. The immune response can be in the form of a cellular or humoral response, or both.

l. Nucleic Acid

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

m. Operably Linked

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

n. Promoter

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

o. Stringent Hybridization Conditions

"Stringent hybridization conditions" as used herein means conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5-10° C. lower than the thermal melting point ($T_m$) for the specific sequence at a defined ionic strength pH. The $T_m$ can be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

p. Substantially Complementary

"Substantially complementary" as used herein means that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, 630, 720, 810, 900, 990, 1080, 1170, 1260, 1350, 1440, 1530, 1620, 1710, 1800, 1890, 1980, 2070 or more nucleotides or amino acids, or that the two sequences hybridize under stringent hybridization conditions.

q. Substantially Identical

"Substantially identical" as used herein means that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, 630, 720, 810, 900, 990, 1080, 1170, 1260, 1350, 1440, 1530, 1620, 1710, 1800, 1890, 1980, 2070 or more nucleotides or amino acids, or with respect to nucleic acids, if the first sequence is substantially complementary to the complement of the second sequence.

r. Subtype or Serotype

"Subtype" or "serotype": as used herein, interchangeably, and in reference to prostate cancer antigens, means genetic variants of a prostate cancer antigen such that one subtype (or variant) is recognized by an immune system apart from a different subtype.

s. Variant

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retains protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

t. Vector

"Vector" as used herein means a nucleic acid sequence containing an origin of replication. A vector can be a vector, bacteriophage, bacterial artificial chromosome or yeast artificial chromosome. A vector can be a DNA or RNA vector. A vector can be a self-replicating extrachromosomal vector, and preferably, is a DNA plasmid.

2. CONSENSUS PROSTATE ANTIGENS

Provided herein are consensus antigens capable of eliciting an immune response in a mammal against a prostate antigen. The consensus antigen can comprise epitopes that make them particularly effective as immunogens against prostate cancer cells can be induced. The consensus prostate antigen can comprise the full length translation product, a variant thereof, a fragment thereof or a combination thereof.

Seven different consensus prostate antigens have been designed. Two of the consensus prostate antigens are consensus PSA antigen 1 (SEQ ID NO:2) and consensus PSA antigen 2 (SEQ ID NO:4). Two of the consensus prostate antigens are consensus PSMA antigen 1 (SEQ ID NO:6) and consensus PSMA antigen 2 (SEQ ID NO:8). Two of the consensus prostate antigens are consensus STEAP antigen 1 (SEQ ID NO:10) and consensus STEAP antigen 2 (SEQ ID NO:12). One of the consensus prostate antigens is consensus PSCA antigen (SEQ ID NO:14). Proteins may comprise sequences homologous to the prostate antigens, fragments of the prostate antigens and proteins with sequences homologous to fragments of the prostate antigens.

Consensus PSA antigen 1 (SEQ ID NO:2) is about 91% homologous to human PSA sequences, about 95% homologous to *M. fascicuaris* PSA and about 96% homologous to *M. mulatta* PSA. Consensus PSA antigen 1 differs from human PSA sequences at amino acids 69, 78, 80, 82, 102, 110, 137, 139, 165, 189, 203, 220, 232 and 248 of SEQ ID NO:2.

Consensus PSA antigen 2 (SEQ ID NO:4) is about 90-91% homologous to human PSA sequences, about 95% homologous to *M. fascicuaris* PSA and about 95% homologous to *M.*

*mulatta* PSA. Consensus PSA antigen 2 comprises a leader sequence at its N terminus Consensus PSA antigen 2 also differs from human PSA sequences at amino acids 21, 86, 127, 129, 154, 156, 182, 195, 206, 218, 220, 237, 249, 255, 265, 271 and 275 of SEQ ID NO:4.

Consensus PSMA antigen 1 (SEQ ID NO:6) is about 96% homologous to human PSMA sequences and about 94% homologous to *M. mulatta* PSMA. Consensus PSMA antigen 1 differs from human PSMA sequences at amino acids 14, 15, 32, 47, 58, 79, 111, 157, 223, 320, 350, 475, 499, 569, 613, 624, 653, 660, 663, 733 and 734 of SEQ ID NO:6.

Consensus PSMA antigen 2 (SEQ ID NO:8) is about 96% homologous to human PSA sequences and about 94% homologous to *M. mulatta* PSA. Consensus PSMA antigen 2 comprises a leader sequence at its N terminus. Consensus PSMA antigen 2 also differs from human PSA sequences at amino acids 21, 31, 32, 49, 64, 75, 96, 128, 174, 240, 337, 367, 492, 516, 565, 586, 630 641 670 677 680 750 and 751 of SEQ ID NO:8.

Consensus STEAP antigen 1 (SEQ ID NO:10) is about 94% homologous to some human STEAP sequences and about 99% homologous to other human STEAP sequences. Consensus STEAP antigen 1 (SEQ ID NO:10) is also about 94% homologous to *M. mulatta* PSMA.

Consensus STEAP antigen 2 (SEQ ID NO:12) is about 88% homologous to some human STEAP sequences and about 94% homologous to other human STEAP sequences. Consensus STEAP antigen 2 (SEQ ID NO:12) is also about 94% homologous to *M. mulatta* PSMA. Consensus STEAP antigen 2 comprises a leader sequence at its N terminus.

Consensus PSCA antigen (SEQ ID NO:14) is about 87% homologous to human PSCA. Consensus PSCA antigen (SEQ ID NO:14) differs from human PSCA by inclusion of a leader sequence at its N terminus.

Proteins may have sequences 98% homologous to PSA Consensus Antigen sequence 1 (SEQ ID NO:2), PSA Consensus Antigen sequence 2 (SEQ ID NO:4), PSMA Consensus Antigen sequence 1 (SEQ ID NO:6), PSMA Consensus Antigen sequence 2 (SEQ ID NO:8), STEAP Consensus Antigen sequence 1 (SEQ ID NO:10), STEAP Consensus Antigen sequence 2 (SEQ ID NO:12) or PSCA Consensus Antigen sequence (SEQ ID NO:14).

Proteins may have sequences 99% homologous to PSA Consensus Antigen sequence 1 (SEQ ID NO:2), PSA Consensus Antigen sequence 2 (SEQ ID NO:4), PSMA Consensus Antigen sequence 1 (SEQ ID NO:6), PSMA Consensus Antigen sequence 2 (SEQ ID NO:8), STEAP Consensus Antigen sequence 1 (SEQ ID NO:10), STEAP Consensus Antigen sequence 2 (SEQ ID NO:12) or PSCA Consensus Antigen sequence (SEQ ID NO:14).

As noted above, some embodiments comprise a leader sequence at the N terminus. In some embodiments, the leader sequence is an IgE leader sequence that is SEQ ID NO:16. In some embodiments of the protein sequences provided herein, SEQ ID NO:16 is removed therefrom. Likewise, in some embodiments of the nucleic acid sequences provided herein, SEQ ID NO:15 (which encodes SEQ ID NO:16) is removed therefrom.

Accordingly, some embodiments related protein that comprise a signal peptide linked to SEQ ID NO:2, SEQ ID NO:6, or SEQ ID NO:10 in place of the N terminal methionine set forth in the claim (the coding sequence of the signal peptide typically includes a stsart codon encoding an N terminal methionine). Some embodiments relate to a protein that comprises a signal peptide linked to amino acid 19-131 of SEQ ID NO:14. Some embodiments related to proteins that comprise a signal peptide linked to a protein 98% homologous to SEQ ID NO:2 provided amino acids 69, 78, 80, 82, 102, 110, 137, 139, 165, 189, 203, 220, 232 and 248 of SEQ ID NO:2 are conserved. Some embodiments related to proteins that comprise a signal peptide linked to a protein 98% homologous to SEQ ID NO:6 provided amino acids 14, 15, 32, 47, 58, 79, 111, 157, 223, 320, 350, 475, 499, 569, 613, 624, 653, 660, 663, 733 and 734 of SEQ ID NO:6 are conserved. Some embodiments related to proteins that comprise a signal peptide linked to a protein 98% homologous to SEQ ID NO:10, In each instance in which the signal peptide is linked at the N terminal it is linked in place of the N terminal methionine set forth in the claim (the coding sequence of the signal peptide typically includes a stsart codon encoding an N terminal methionine). Some embodiments relate to a protein that comprises a signal peptide linked to linked to a protein 98% homologous to amino acid 19-131 of SEQ ID NO:14. Some embodiments relate to a protein that comprises a signal peptide linked to linked to an immunogenic fragment of SEQ ID NO:2 comprising amino acids corresponding to at least 256 amino acid residues of SEQ ID NO:2, provided amino acids 69, 78, 80, 82, 102, 110, 137, 139, 165, 189, 203, 220, 232 and 248 of SEQ ID NO:2 are conserved. Some embodiments relate to a protein that comprises a signal peptide linked to linked to an immunogenic fragment of SEQ ID NO:6 comprising amino acids corresponding to at least 735 amino acid residues of SEQ ID NO:6, provided amino acids 14, 15, 32, 47, 58, 79, 111, 157, 223, 320, 350, 475, 499, 569, 613, 624, 653, 660, 663, 733 and 734 of SEQ ID NO:6 are conserved. Some embodiments relate to a protein that comprises a signal peptide linked to an immunogenic fragment of SEQ ID NO:10 comprising amino acids corresponding to at least 333 amino acid residues of SEQ ID NO:10. Some embodiments relate to a protein that comprises a signal peptide linked to linked to protein that has a signal peptide linked to an immunogenic fragment of amino acids 19-131 of SEQ ID NO:14, the fragment comprising at least 110 amino acid residues of SEQ ID NO:14.

3. GENETIC SEQUENCES, CONSTRUCTS AND PLASMIDS

Nucleic acid molecules encoding the consensus amino acid sequences were generated to optimize stability and expression in humans. Codon selection was determined based upon, inter alia, an effort to minimize intramolecular interactions and secondary structure formation as well as using codons which result in improved expression. Vaccines may comprise one or more nucleic acid sequences that encode one or more of the consensus versions of the immunogenic proteins selected from this group of sequences generated to optimize stability and expression in humans. Nucleic acid sequences incorporating coding sequence for the IgE leader at the 5' end of the optimized, consensus encoding nucleic acid sequence were generated which encoded proteins having the IgE leader sequence at the N terminus of the consensus amino acid sequence. In some embodiments, the nucleic acid sequence that encodes the IgE leader is SEQ ID NO:15

Nucleic acid sequences are provided which encode PSA Consensus Antigen sequence 1 (protein sequence SEQ ID NO:2; nucleic acid sequence SEQ ID NO:1), PSA Consensus Antigen sequence 2 (protein sequence SEQ ID NO:4; nucleic acid sequence SEQ ID NO:3), PSMA Consensus Antigen sequence 1 (protein sequence SEQ ID NO:6; nucleic acid sequence having nucleotides 1-2250 of SEQ ID NO:5), PSMA Consensus Antigen sequence 2 (protein sequence SEQ ID NO:8; nucleic acid sequence having nucleotides 1-2301 of SEQ ID NO:7), STEAP Consensus Antigen sequence 1 (protein sequence SEQ ID NO:10; nucleic acid sequence SEQ ID NO:9), STEAP Consensus Antigen sequence 2 (protein sequence SEQ ID NO:12; nucleic acid sequence SEQ ID NO:11) or PSCA Consensus Antigen sequence (protein sequence SEQ ID NO:14; nucleic acid sequence SEQ ID NO:13). The nucleic acid sequence SEQ ID NO:5 which encodes PSMA Consensus Antigen sequence 1 comprises, in addition to PSMA encoding nucleotides, an additional 9 codons (27 nucleotides) immediately before the stop codons which encode the HA Tag (SEQ ID NO:32), not shown in SEQ ID NO:6. The HA Tag is peptide sequence that corresponds to an influenza epitope useful for among other things detection of protein. expression using commercially available anti-HA Tag antibodies. SEQ ID NO:5 encodes SEQ ID NO:6 plus an additional 9 amino acid sequence SEQ ID NO:32 linked to at its N terminus to the C terminus of SEQ ID NO:6. In some embodiments, the PSMA-1 Consensus antigen is encoded by SEQ ID NO:5 and comprises a proteins having an amino acid sequence of SEQ ID NO:6 linked at its C terminus to the N terminus of SEQ ID NO:32. In some embodiments, the PSMA-1 Consensus antigen is encoded by nucleotides 1-2250 of SEQ ID NO:5 and comprises a proteins having an amino acid sequence of SEQ ID NO:6. The coding sequence having nucleotides 1-2250 of SEQ ID NO:5 has one or more stop codons at its 3' end. The nucleic acid sequence SEQ ID NO:7 which encodes PSMA Consensus Antigen sequence 2 comprises, in addition to nucleotides encoding the IgE signal linked to the PSMA, protein plus an additional 9 codons (27 nucleotides) immediately before the stop codons which encode the HA Tag (SEQ ID NO:32), not shown in SEQ ID NO:8. SEQ ID NO:7 encodes SEQ ID NO:8 plus an additional 9 amino acid sequence SEQ ID NO:32 linked to at its N terminus to the C terminus of SEQ ID NO:8. In some embodiments, the PSMA-2 Consensus antigen is encoded by SEQ ID NO:7 and comprises a proteins having an amino acid sequence of SEQ ID NO:8 linked at its C terminus to the N terminus of SEQ ID NO:32. In some embodiments, the PSMA-2 Consensus antigen is encoded by nucleotides 1-2301 of SEQ ID NO:7 and comprises a proteins having an amino acid sequence of SEQ ID NO:8. The coding sequence having nucleotides 1-2301 of SEQ ID NO:7 has one or more stop codons at its 3' end.

Isolated nucleic acid molecules can encode proteins that have sequences 98% homologous to PSA Consensus Antigen sequence 1 (SEQ ID NO:2), provided amino acids 69, 78, 80, 82, 102, 110, 137, 139, 165, 189, 203, 220, 232 and 248 of SEQ ID NO:2 are conserved, PSA Consensus Antigen sequence 2 (SEQ ID NO:4), provided amino acids 21, 86, 127, 129, 154, 156, 182, 195, 206, 218, 220, 237, 249, 255, 265, 271 and 275 of SEQ ID NO:4 are conserved, PSMA Consensus Antigen sequence 1 (SEQ ID NO:6), provided amino acids 14, 15, 32, 47, 58, 79, 111, 157, 223, 320, 350, 475, 499, 569, 613, 624, 653, 660, 663, 733 and 734 of SEQ ID NO:6 are conserved, PSMA Consensus Antigen sequence 2 (SEQ ID NO:8), provided amino acids 20, 30, 31, 48, 63, 74, 95, 127, 173, 239, 336, 366, 491, 515, 564, 585, 629, 640, 669, 676, 679, 749 and 750 of SEQ ID NO:8 are conserved, STEAP Consensus Antigen sequence 1 (SEQ ID NO:10), STEAP Consensus Antigen sequence 2 (SEQ ID NO:12) or PSCA Consensus Antigen sequence (SEQ ID NO:14).

Isolated nucleic acid molecules can encode proteins that have sequences 99% homologous to PSA Consensus Antigen sequence 1 (SEQ ID NO:2), provided amino acids 69, 78, 80, 82, 102, 110, 137, 139, 165, 189, 203, 220, 232 and 248 of SEQ ID NO:2 are conserved, PSA Consensus Antigen sequence 2 (SEQ ID NO:4), provided amino acids 21, 86, 127, 129, 154, 156, 182, 195, 206, 218, 220, 237, 249, 255, 265, 271 and 275 of SEQ ID NO:4 are conserved, PSMA Consensus Antigen sequence 1 (SEQ ID NO:6), provided amino acids 14, 15, 32, 47, 58, 79, 111, 157, 223, 320, 350, 475, 499, 569, 613, 624, 653, 660, 663, 733 and 734 of SEQ ID NO:6 are conserved, PSMA Consensus Antigen sequence 2 (SEQ ID NO:8), provided amino acids 21, 31, 32, 49, 64, 75, 96, 128, 174, 240, 337, 367, 492, 516, 565, 586, 630, 641, 670, 677, 680, 750, and 751 of SEQ ID NO:8 are conserved, STEAP Consensus Antigen sequence 1 (SEQ ID NO:10), STEAP Consensus Antigen sequence 2 (SEQ ID NO:12) or PSCA Consensus Antigen sequence (SEQ ID NO:14).

Isolated nucleic acid molecules can encode proteins that have sequences 98% homologous to the sequence encoding PSA Consensus Antigen sequence 1 (SEQ ID NO:1), PSA Consensus Antigen sequence 2 (SEQ ID NO:3), PSMA Consensus Antigen sequence 1 (SEQ ID NO:5 or preferably nucleotides 1-2250 of SEQ ID NO:5), PSMA Consensus Antigen sequence 2 (SEQ ID NO:7 or preferably nucleotides 1-2301 of SEQ ID NO:7), STEAP Consensus Antigen sequence 1 (SEQ ID NO:9), STEAP Consensus Antigen sequence 2 (SEQ ID NO:11) or PSCA Consensus Antigen sequence (SEQ ID NO:13).

Isolated nucleic acid molecules can encode proteins that have sequences 99% homologous to the sequence encoding PSA Consensus Antigen sequence 1 (SEQ ID NO:1), PSA Consensus Antigen sequence 2 (SEQ ID NO:3), PSMA Consensus Antigen sequence 1 (SEQ ID NO:5 or preferably nucleotides 1-2250 of SEQ ID NO:5), PSMA Consensus Antigen sequence 2 (SEQ ID NO:7 0r preferably nucleotides 1-2301 of SEQ ID NO:7), STEAP Consensus Antigen sequence 1 (SEQ ID NO:9), STEAP Consensus Antigen sequence 2 (SEQ ID NO:11) or PSCA Consensus Antigen sequence (SEQ ID NO:13).

Isolated nucleic acid molecules can encode proteins that comprise a leader sequence at the N terminus. In some embodiments, the nucleic acid molecules can encode the IgE leader sequence that is SEQ ID NO:16. In some embodiments isolated nucleic acid molecules can encode proteins that comprise a signal peptide linked to SEQ ID NO:2, SEQ ID NO:6, or SEQ ID NO:10 in place of the N terminal methionine set forth in the claim (the coding sequence of the signal peptide typically includes a stsart codon encoding an N terminal methionine). In some embodiments isolated nucleic acid molecules can encode proteins that comprise a signal peptide linked to amino acid 19-131 of SEQ ID NO:14. In some embodiments isolated nucleic acid molecules can encode proteins that comprise a signal peptide linked to a protein 98% homologous to SEQ ID NO:2 provided amino acids 69, 78, 80, 82, 102, 110, 137, 139, 165, 189, 203, 220, 232 and 248 of SEQ ID NO:2 are conserved. In some embodiments isolated nucleic acid molecules can encode proteins that comprise a signal peptide linked to a protein 98% homologous to SEQ ID NO:6 provided amino acids 14, 15, 32, 47, 58, 79, 111, 157, 223, 320, 350, 475, 499, 569, 613, 624, 653, 660, 663, 733 and 734 of SEQ ID NO:6 are conserved. In some embodiments isolated nucleic acid molecules can encode proteins that comprise a signal peptide linked to a protein 98% homologous to SEQ ID NO:10. In instance in which coding sequence for a signal peptide is provides, the signal peptide is linked to the peptide sequence in place of the N terminal methionine set forth in the sequences shown (the coding sequence of the signal peptide typically includes a stsart codon encoding an N terminal methionine). In some embodiments isolated nucleic acid molecules can encode proteins that comprise a signal peptide linked to linked to a protein 98% homologous to amino acid 19-131 of SEQ ID NO:14. In some embodiments isolated nucleic acid molecules can encode proteins that comprise a signal peptide linked to linked to an immunogenic fragment of SEQ ID NO:2 comprising amino acids corresponding to at least 256 amino acid residues of SEQ ID NO:2, provided amino acids 69, 78, 80, 82, 102, 110, 137, 139, 165, 189, 203, 220, 232 and 248 of SEQ ID NO:2 are conserved. In some embodiments isolated nucleic acid molecules can encode proteins that comprise a signal peptide linked to linked to an immunogenic fragment of SEQ ID NO:6 comprising amino acids corresponding to at least 735 amino acid residues of SEQ ID NO:6, provided amino acids 14, 15, 32, 47, 58, 79, 111, 157, 223, 320, 350, 475, 499, 569, 613, 624, 653, 660, 663, 733 and 734 of SEQ ID NO:6 are conserved. S In some embodiments isolated nucleic acid molecules can encode proteins that comprise a signal peptide linked to an immunogenic fragment of SEQ ID NO:10 comprising amino acids corresponding to at least 333 amino acid residues of SEQ ID NO:10. In some embodiments isolated nucleic acid molecules can encode proteins that comprise a signal peptide linked to linked to protein that has a signal peptide linked to an immunogenic fragment of amino acids 19-131 of SEQ ID NO:14, the fragment comprising at least 110 amino acid residues of SEQ ID NO:14.

Provided herein are genetic constructs that can comprise a nucleic acid sequence that encodes consensus prostate antigen disclosed herein including consensus protein sequences, sequences homologous to consensus protein sequences, fragments of consensus protein sequences and sequences homologous to fragments of consensus protein sequences. The genetic construct can be present in the cell as a functioning extrachromosomal molecule. The genetic construct can be linear minichromosome including centromere, telomers or plasmids or cosmids.

The genetic construct can also be part of a genome of a recombinant viral vector, including recombinant adenovirus, recombinant adenovirus associated virus and recombinant vaccinia. The genetic construct can be part of the genetic material in attenuated live microorganisms or recombinant microbial vectors which live in cells.

The genetic constructs can comprise regulatory elements for gene expression of the coding sequences of the nucleic acid. The regulatory elements can be a promoter, an enhancer an initiation codon, a stop codon, or a polyadenylation signal.

The nucleic acid sequences may make up a genetic construct that can be a vector. The vector can be capable of expressing an antigen in the cell of a mammal in a quantity effective to elicit an immune response in the mammal. The vector can be recombinant. The vector can comprise heterologous nucleic acid encoding the antigen. The vector can be a plasmid. The vector can be useful for transfecting cells with nucleic acid encoding an antigen, which the transformed host cell is cultured and maintained under conditions wherein expression of the antigen takes place.

In some embodiments, coding sequences for a single consensus prostate antigen is provided on a single vector. In some embodiments, coding sequences for a multiple consensus prostate antigen are provided on a single vector. In some embodiments, compositions are provided comprising coding sequences for a multiple consensus prostate antigens on multiple vectors, either one antigen per vector or multiple antigens per vector.

In some embodiments, coding sequences for two or more different consensus prostate antigens may be provided on a single vector. In some embodiments, the coding sequences may have separate promoters controlling expression. In some embodiments, the coding sequences may have a single promoters controlling expression with an IRES sequence separating coding sequence. The presence of the IRES sequence results in the separate translation of the transcription product. In some embodiments, the coding sequences may have a single promoters controlling expression with coding sequence encoding a proteolytic cleavage peptide sequence separating coding sequences of the antigens. A single translation product is produced which is then processed by the protease that recognizes the protease cleavage site to generate separate protein molecules. The protease cleave sites used is typically recognized by a protease endogenously present in the cell where expression occurs. In some embodiments, a separate coding sequence for a protease may be included to provide for the production of the protease needed to process the polyprotein translation product. In some embodiment, vectors comprise coding sequences for one, two, three, four, five, six or all seven consensus prostate antigens.

In each and every instance set forth herein, coding sequences may be optimized for stability and high levels of expression. In some instances, codons are selected to reduce secondary structure formation of the RNA such as that formed due to intramolecular bonding.

The vector can comprise heterologous nucleic acid encoding an antigen and can further comprise an initiation codon, which can be upstream of the antigen coding sequence, and a stop codon, which can be downstream of the antigen coding sequence. The initiation and termination codon can be in frame with the antigen coding sequence. The vector can also comprise a promoter that is operably linked to the antigen coding sequence. The promoter operably linked to the antigen coding sequence can be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter can also be a promoter from a human gene such as human actin, human myosin, human hemoglobin, human muscle creatine, or human metalothionein. The promoter can also be a tissue specific promoter, such as a muscle or skin specific promoter, natural or synthetic. Examples of such promoters are described in US patent application publication no. US20040175727, the contents of which are incorporated herein in its entirety.

The vector can also comprise a polyadenylation signal, which can be downstream of the consensus prostate antigen coding sequence. The polyadenylation signal can be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal can be a polyadenylation signal from a pCEP4 vector (Invitrogen, San Diego, Calif.).

The vector can also comprise an enhancer upstream of the consensus prostate antigen coding sequence. The enhancer can be necessary for DNA expression. The enhancer can be human actin, human myosin, human hemoglobin, human muscle creatine or a viral enhancer such as one from CMV, HA, RSV or EBV. Polynucleotide function enhances are described in U.S. Pat. Nos. 5,593,972, 5,962,428, and WO94/016737, the contents of each are fully incorporated by reference.

The vector can also comprise a mammalian origin of replication in order to maintain the vector extrachromosomally and produce multiple copies of the vector in a cell. The vector can be pVAX1, pCEP4 or pREP4 from Invitrogen (San Diego, Calif.), which can comprise the Epstein Barr virus origin of replication and nuclear antigen EBNA-1 coding region, which can produce high copy episomal replication without integration. The backbone of the vector can be pAV0242. The vector can be a replication defective adenovirus type 5 (Ad5) vector.

The vector can also comprise a regulatory sequence, which can be well suited for gene expression in a mammalian or human cell into which the vector is administered. The consensus prostate antigen coding sequence can comprise a codon, which can allow more efficient transcription of the coding sequence in the host cell.

The vector can be pSE420 (Invitrogen, San Diego, Calif.), which can be used for protein production in *Escherichia coli* (*E. coli*). The vector can also be pYES2 (Invitrogen, San Diego, Calif.), which can be used for protein production in *Saccharomyces cerevisiae* strains of yeast. The vector can also be of the MAXBAC™ complete baculovirus expression system (Invitrogen, San Diego, Calif.), which can be used for protein production in insect cells. The vector can also be pcDNA I or pcDNA3 (Invitrogen, San Diego, Calif.), which may be used for protein production in mammalian cells such as Chinese hamster ovary (CHO) cells. The vector can be expression vectors or systems to produce protein by routine techniques and readily available starting materials including Sambrook et al., Molecular Cloning and Laboratory Manual, Second Ed., Cold Spring Harbor (1989), which is incorporated fully by reference.

Vaccines may comprise one or more of the prostate antigens set forth herein and/or vaccines may comprise one or more nucleic acid sequences that encode one or more of the consensus prostate antigen selected from this group. Vaccines may comprise one or more of the consensus prostate antigens set forth herein in combination with other immunogenic prostate proteins with sequences other than the consensus sequences disclosed herein including native sequences and/or vaccines may comprise one or more nucleic acid sequences that encode one or more of the consensus prostate antigens selected from this group in combination with nucleic acid molecules that encode other prostate antigens with sequences other than the consensus sequences disclosed herein.

While not being bound by scientific theory, a vaccine that can be used to elicit an immune response (humoral, cellular, or both) broadly against prostate cancer cells may comprise one or more of the following nucleic acid sequences that encodes one or more proteins selected from the group consisting of: consensus, PSA antigen 1, consensus, PSA antigen 2, consensus, PSMA antigen 1, consensus, PSMA antigen 2, consensus STEAP antigen 1, consensus STEAP antigen 2 and consensus PSCA antigen 1. Coding sequences may also include those provided herein that comprise homologous sequences, fragments, and homologous sequences of fragments.

Some embodiments provide methods of generating immune responses against prostate cancer cells comprise administering to an individual one or more compositions which collectively comprise one or more coding sequences or combinations described herein. Some embodiments provide methods of prophylactically vaccinating an individual against prostate cancer comprise administering one or more compositions which collectively comprise one or more coding sequences or combinations described herein. Some embodiments provide methods of therapeutically vaccinating an individual has prostate cancer that comprise administering one or more compositions which collectively comprise one or more coding sequences or combinations described herein.

4. PHARMACEUTICAL COMPOSITIONS

Provided herein are pharmaceutical compositions according to the present invention which comprise about 1 nanogram to about 10 mg of DNA. In some embodiments, pharmaceutical compositions according to the present invention comprise from between: 1) at least 10, 15, 20, 25, 30, 35, 40, 45, 50, 55, 60, 65, 70, 75, 80, 85, 90, 95 or 100 nanograms, or at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995 or 1000 micrograms, or at least 1.5, 2, 2.5, 3, 3.5, 4, 4.5, 5, 5.5, 6, 6.5, 7, 7.5, 8, 8.5, 9, 9.5 or 10 mg or more; and 2) up to and including 15, 20, 25, 30, 35, 40, 45, 50, 55, 60, 65, 70, 75, 80, 85, 90, 95 or 100 nanograms, or up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or 1000 micrograms, or up to and including 1.5, 2, 2.5, 3, 3.5, 4, 4.5, 5, 5.5, 6, 6.5, 7, 7.5, 8, 8.5, 9, 9.5 or 10 mg. In some embodiments, pharmaceutical compositions according to the present invention comprise about 5 nanogram to about 10 mg of DNA. In some embodiments, pharmaceutical compositions according to the present invention comprise about 25 nanogram to about 5 mg of DNA. In some embodiments, the pharmaceutical compositions contain about 50 nanograms to about 1 mg of DNA. In some embodiments, the pharmaceutical compositions contain about 0.1 to about 500 micrograms of DNA. In some embodiments, the pharmaceutical compositions contain about 1 to about 350 micrograms of DNA. In some embodiments, the pharmaceutical compositions contain about 5 to about 250 micrograms of DNA. In some embodiments, the pharmaceutical compositions contain about 10 to about 200 micrograms of DNA. In some embodiments, the pharmaceutical compositions contain about 15 to about 150 micrograms of DNA. In some embodiments, the pharmaceutical compositions contain about 20 to about 100 micrograms of DNA. In some embodiments, the pharmaceutical compositions contain about 25 to about 75 micrograms of DNA. In some embodiments, the pharmaceutical compositions contain about 30 to about 50 micrograms of DNA. In some embodiments, the pharmaceutical compositions contain about 35 to about 40 micrograms of DNA. In some embodiments, the pharmaceutical compositions contain about 100 to about 200 microgram DNA. In some embodiments, the pharmaceutical compositions comprise about 10 microgram to about 100 micrograms of DNA. In some embodiments, the pharmaceutical compositions comprise about 20 micrograms to about 80 micrograms of DNA. In some embodiments, the pharmaceutical compositions comprise about 25 micrograms to about 60 micrograms of DNA. In some embodiments, the pharmaceutical compositions comprise about 30 nanograms to about 50 micrograms of DNA. In some embodiments, the pharmaceutical compositions comprise about 35 nanograms to about 45 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

Preferably the pharmaceutical composition is a vaccine, and more preferably a DNA vaccine.

The vaccine may be a DNA vaccine. The DNA vaccine may comprise a plurality of the same or different plasmids comprising nucleic acid coding sequences for one or more of consensus prostate antigens. The DNA vaccine may comprise one or more nucleic acid sequences that encode one or more of consensus prostate antigens. When the DNA vaccine comprises coding sequences of more than one consensus prostate antigens all such sequences may be present on a single plasmid, or each such sequences may be present on a different plasmids.

In some embodiments, vaccines may comprise nucleic acid sequences that encode one or more of consensus prostate antigens in combination with one or more of consensus prostate antigens.

DNA vaccines are disclosed in U.S. Pat. Nos. 5,593,972, 5,739,118, 5,817,637, 5,830,876, 5,962,428, 5,981,505, 5,580,859, 5,703,055, and 5,676,594, which are incorporated herein fully by reference. The DNA vaccine can further comprise elements or reagents that inhibit it from integrating into the chromosome. The vaccine can be an RNA of the prostate antigen. The RNA vaccine can be introduced into the cell.

The vaccine can be a recombinant vaccine comprising the genetic construct or antigen described above. The vaccine can also comprise one or more consensus prostate antigens in the form of one or more protein subunits, or one or more attenuated viral particles comprising one or more consensus prostate antigens. The attenuated vaccine can be attenuated live vaccines, killed vaccines and vaccines that use recombinant vectors to deliver foreign genes that encode one or more consensus prostate antigens, and well as subunit and glycoprotein vaccines. Examples of attenuated live vaccines, those using recombinant vectors to deliver prostate antigens, subunit vaccines and glycoprotein vaccines are described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

The vaccine provided may be used to induce immune responses including therapeutic or prophylactic immune responses. Antibodies and/or killer T cells may be generated which are directed to the consensus prostate antigen. Such antibodies and cells may be isolated.

The vaccine can further comprise a pharmaceutically acceptable excipient. The pharmaceutically acceptable excipient can be functional molecules as vehicles, adjuvants, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the vaccine at a concentration less than 6 mg/ml. The transfection facilitating agent can also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid can also be used administered in conjunction with the genetic construct. In some embodiments, the DNA vector vaccines can also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient may be an adjuvant. The adjuvant may be other genes that are expressed in alternative plasmid or are delivered as proteins in combination with the plasmid above in the vaccine. The adjuvant may be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant may be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

Other genes which may be useful adjuvants include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRCS, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The vaccine can further comprise a genetic vaccine facilitator agent as described in U.S. Ser. No. 021,579 filed Apr. 1, 1994, which is fully incorporated by reference.

5. METHODS OF DELIVERY

Provided herein is a method for delivering the pharmaceutical formulations, preferably vaccines, for providing genetic constructs and consensus prostate antigen which comprise epitopes that make them particular effective immunogens against which an immune response to prostate cancer cells can be induced. The method of delivering the vaccine, or vaccination, can be provided to induce a therapeutic and/or prophylactic immune response. The vaccine can be delivered to an individual to modulate the activity of the mammal's immune system and enhance the immune response.

Upon delivery of the vaccine to the mammal, and thereupon the vector into the cells of the mammal, the transfected cells will express and secrete the corresponding prostate consensus protein. These secreted proteins, or synthetic antigens, will be recognized by the immune system, which will mount an immune response that can include: antibodies made against the antigens, and T-cell response specifically against the antigen. In some examples, a mammal vaccinated with the vaccines discussed herein will have a primed immune system. The vaccine can be delivered to an individual to modulate the activity of the individual's immune system thereby enhancing the immune response.

The vaccine can be delivered in the form of a DNA vaccine and methods of delivering a DNA vaccines are described in U.S. Pat. Nos. 4,945,050 and 5,036,006, which are both incorporated fully by reference.

The vaccine can be administered to a mammal to elicit an immune response in a mammal. The mammal can be human, non-human primate, cow, pig, sheep, goat, antelope, bison, water buffalo, bovids, deer, hedgehogs, elephants, llama, alpaca, mice, rats, or chicken, and preferably human, cow, pig, or chicken.

a. Combination Treatments

The pharmaceutical compositions, preferably vaccines, can be administered in combination with one or more other prostate proteins or genes. The vaccine can be administered in combination with proteins or genes encoding adjuvants, which can include: α-interferon (IFN-α), β-interferon (IFN-β), γ-interferon, IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, MCP-1, MIP-1a, MIP-1p, IL-8, RANTES, L-selectin, P-selectin, E-selectin, CD34, Gly-CAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRCS, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, or TAP2, or functional fragments thereof.

b. Routes of Administration

The vaccine can be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition can be administered as a suitably acceptable formulation in accordance with normal veterinary practice. The veterinarian can readily determine the dosing regimen and route of administration that is most appropriate for a particular animal. The vaccine can be administered by traditional syringes, needleless injection devices, "microprojectile bombardment gone guns", or other physical methods such as electroporation ("EP"), "hydrodynamic method", or ultrasound.

The vector of the vaccine can be delivered to the mammal by several well known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. The prostate antigen can be delivered via DNA injection and along with in vivo electroporation.

c. Electroporation

Administration of the vaccine via electroporation of the plasmids of the vaccine may be accomplished using electroporation devices that can be configured to deliver to a desired tissue of a mammal a pulse of energy effective to cause reversible pores to form in cell membranes, and in some embodiments, the pulse of energy is a constant current similar to a preset current input by a user.

In some embodiments where electroporation is utilized, the electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA® EP system (Inovio Pharmaceuticals, Inc., Blue Bell, Pa.) or Elgen electroporator (Inovio Pharmaceuticals, Inc., Blue Bell, Pa.) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 µs, 20 µs, 10 µs or 1 µs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the DNA vaccines of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the DNA vaccines include those provided in co-pending and co-owned U.S. patent application Ser. No. 11/874,072, filed Oct. 17, 2007, which claims the benefit under 35 USC 119(e) to U.S. Provisional Application Ser. Nos. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety. Another embodiment of an electroporation device to be used with the cancer antigens described herein is the Elgen EP device (Inovio Pharmaceuticals, Inc., Blue Bell, Pa.).

d. Method of Preparing Vaccine

Provided herein is methods for preparing the DNA plasmids that comprise the DNA vaccines discussed herein. The DNA plasmids, after the final subcloning step into the mammalian expression plasmid, can be used to inoculate a cell culture in a large scale fermentation tank, using known methods in the art.

The DNA plasmids for use with the EP devices of the present invention can be formulated or manufactured using a combination of known devices and techniques, but preferably they are manufactured using an optimized plasmid manufacturing technique that is described in a licensed, co-pending U.S. provisional application U.S. Ser. No. 60/939,792, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Consensus immunogens for PSA and PSMA were designed from the available full-length human and macaque sequences in the GenBank database as previously described in Laddy, D. J., Yan, J., Corbitt, N., Kobasa, D., Kobinger, G. P., Weiner, D. B. (2007). Immunogenicity of novel consensus-based DNA vaccines against avian influenza. Vaccine. 25, 2984-2989, and Laddy, D. J., Yan, J., Kutzler, M., Kobasa, D., Kobinger, G. P., Khan, A. S., Greenhouse, J., Sardesai, N. Y., Draghia-Akli, R., Weiner, D. B. (2008). Heterosubtypic Protection against Pathogenic Human and Avian Influenza Viruses via In Vivo Electroporation of Synthetic Consensus DNA Antigens. PLoS ONE. 3,e2517.

The consensus antigen sequences were synthesized by GeneScript (Piscataway, N.J.). An HA tag was included in the C-terminus of the antigen sequence. The antigen sequences were optimized for mRNA stability and codon usage in humans. The final sequences were cloned in the BamHI and XhoI sites of the pVAX1 vector (Invitrogen, Carlsbad, Calif.).

A consensus PSA antigen 1 (SEQ ID NO:2) was generated. This sequence, which comprises 261 amino acids, was compared to each of the PSA sequences set forth in Table 1. The PSA sequences used include two human sequences, a sequence from M. fascicularis, and a sequence from M. mulatta. Table 1 includes the SEQ ID NO: and Accession number for each sequence used in the comparison with consensus PSA antigen 1 (SEQ ID NO:2).

TABLE 1

| SEQ ID NO | Species and protein | Accession Number | Number of amino acids | % homology to SEQ ID NO: 2 |
|---|---|---|---|---|
| 17 | H. sapiens PSA isol | NP001639.1 | 261 | 91 |
| 18 | H. sapiens PSA | gbAAA60193.1 | 262 | 91 |
| 19 | M. fascicularis KLK3 | Q6DT45.1 | 261 | 95 |
| 20 | M. mulatta PSA | NP001036241.1 p | 261 | 96 |

A multiple sequence alignment of H. Sapiens (SEQ ID NO:17 and SEQ ID NO:18), M. mulatta (SEQ ID NO:20) and M. facicularis (SEQ ID NO:19) PSA sequences was generated with the consensus PSA antigen 1 (SEQ ID NO:2). KLK3 (kallikrein 3) is the gene encoding PSA and is pseudonymous with PSA. The PSA antigen 1 is 91% homologous to H. sapiens, 96% homologous to M. mulatta and 95% homologous M. facicularis full-length PSA protein sequences.

Example 2

A consensus PSA antigen 2 (SEQ ID NO:4) was generated. This sequence, which comprises 279 amino acids including an IgE leader sequence, was compared to each of the PSA sequences set forth in Table 2. The PSA sequences used include two human sequences, a sequence from M. fascicularis, and a sequence from M. mulatta. Table 2 includes the SEQ ID NO: and Accession number for each sequence used in the comparison with consensus PSA antigen 2 (SEQ ID NO:4).

TABLE 2

| SEQ ID NO | Species and protein | Accession Number | Number of amino acids | % homology to SEQ ID NO: 4 |
|---|---|---|---|---|
| 17 | H. sapiens PSA isol | NP001639.1 | 261 | 91 |
| 18 | H. sapiens PSA | gbAAA60193.1 | 262 | 90 |
| 19 | M. fascicularis KLK3 | Q6DT45.1 | 261 | 95 |
| 21 | M. mulatta PSA | AAZ82258.1 | 244 | 95 |

A multiple sequence alignment of H. Sapiens (SEQ ID NO:17 and SEQ ID NO:18), M. mulatta (SEQ ID NO:21) and M. facicularis (SEQ ID NO:19) PSA sequences was generated with the consensus PSA antigen 1 (SEQ ID NO:4). KLK3 (kallikrein 3) is the gene encoding PSA and is pseudonymous with PSA. The PSA antigen 1 is 90-91% homologous to H. sapiens and 95% homologous M. facicularis full-length PSA protein sequences, and 95% homologous to M. mulatta partial PSA protein sequence.

Example 3

A consensus PSMA antigen 1 (SEQ ID NO:6) was generated. This sequence, which comprises 750 amino acids was compared to each of the PSMA sequences set forth in Table 3. The PSMA sequences used include two human sequences and a sequence from M. mulatta. Table 3 includes the SEQ ID NO: and Accession number for each sequence used in the comparison with consensus PSMA antigen 1 (SEQ ID NO:6).

TABLE 3

| SEQ ID NO | Species and protein | Accession Number | Number of amino acids | % homology to SEQ ID NO: 6 |
|---|---|---|---|---|
| 22 | H. sapiens PSMA GCPII_isol | NP_004467.1 | 750 | 96 |
| 23 | H. sapiens PSMA | AAC83972.1 | 749 | 96 |
| 24 | M. mulatta GCPII isol | XP_001096141.2 | 735 | 94 |

A multiple sequence alignment of H. Sapiens and M. mulatta PSMA sequences was generated with PSMA antigen 1. The PSMA antigen 1 consensus sequence (SEQ ID NO:6)

is 96% homologous to *H. sapiens* PSMA (SEQ ID NO:22 and SEQ ID NO:23) and 94% homologous to *M. mulatta* full-length PSMA protein sequence (SEQ ID NO:24).

Example 4

A consensus PSMA antigen 2 (SEQ ID NO:8) was generated. This sequence, which comprises 767 amino acids including an IgE leader sequence, was compared to each of the PSMA sequences set forth in Table 4. The PSMA sequences used include two human sequences and a sequence from *M. mulatta*. Table 4 includes the SEQ ID NO: and Accession number for each sequence used in the comparison with consensus PSMA antigen 2 (SEQ ID NO:8).

TABLE 4

| SEQ ID NO | Species and protein | Accession Number | Number of amino acids | % homology to SEQ ID NO: 8 |
|---|---|---|---|---|
| 22 | *H. sapiens* PSMA GCPII_iso1 | NP_004467.1 | 750 | 96 |
| 23 | *H. sapiens* PSMA | AAC83972.1 | 749 | 96 |
| 24 | *M. mulatta* GCPII iso1 | XP_001096141.2 | 735 | 94 |
| 25 | *M. mulatta* GCPII iso2 | XP_002799784.1 | 704 | 94 |

A multiple sequence alignment of *H. sapiens* (SEQ ID NO:22 and SEQ ID NO:23) and *M. mulatta* PSMA sequences (SEQ ID NO:24 and SEQ ID NO:25) was generated with PSMA antigen 2. The PSMA antigen 2 consensus sequence (SEQ ID NO:8) is 96% homologous to *H. sapiens* PSMA protein sequences and 94% homologous to *M. mulatta* PSMA protein sequences.

Example 5

A consensus STEAP antigen 1 (SEQ ID NO:10) was generated. This sequence, which comprises 339 amino acids was compared to each of the STEAP sequences set forth in Table 5. The STEAP sequences used include two full length human sequences, a full length sequence from *M. mulatta* and two shorter human sequences. Table 5 includes the SEQ ID NO: and Accession number for each sequence used in the comparison with consensus STEAP antigen 1 (SEQ ID NO:10).

TABLE 5

| SEQ ID NO | Species and protein | Accession Number | Number of amino acids | % homology to SEQ ID NO: 10 |
|---|---|---|---|---|
| 26 | *H. sapiens* STEAP1 | NP_036581.1 | 339 | 99 |
| 27 | *H. sapiens* STEAP1 | Gb_EAL24167.1 | 339 | 99 |
| 28 | *M. mulatta* STEAP1 | XP_001103605.1 | 339 | 98 |
| 29 | *H. sapiens* STEAP1 CRA b | EAW93751.1 | 259 | 94 |
| 30 | *H. sapiens* STEAP1 isofor | EAW93749.1 | 258 | 94 |

A multiple sequence alignment of *H. Sapiens* and *M. mulatta* STEAP sequences was generated with the consensus STEAP antigen 1. The STEAP antigen 1 consensus sequence (SEQ ID NO:10) is 99% homologous to human full-length isoforms (SEQ ID NO:26 and SEQ ID NO:27), 94% homologous to shorter *H. sapiens* isoforms (SEQ ID NO:29 and SEQ ID NO:30), and 94% homologous to *M. mulatta* full-length STEAP1 protein sequence (SEQ ID NO:28).

Example 6

A consensus STEAP antigen 2 (SEQ ID NO:12) was generated. This sequence, which comprises 356 amino acids was compared to each of the STEAP sequences set forth in Table 6. The STEAP sequences used include two full length human sequences, a full length sequence from *M. mulatta* and two shorter human sequences. Table 6 includes the SEQ ID NO: and Accession number for each sequence used in the comparison with consensus STEAP antigen 2 (SEQ ID NO:12).

TABLE 6

| SEQ ID NO | Species and protein | Accession Number | Number of amino acids | % homology to SEQ ID NO: 12 |
|---|---|---|---|---|
| 26 | *H. sapiens* STEAP1 | NP_036581.1 | 339 | 94 |
| 27 | *H. sapiens* STEAP1 | Gb_EAL24167.1 | 339 | 94 |
| 28 | *M. mulatta* STEAP1 | XP_001103605.1 | 339 | 94 |
| 29 | *H. sapiens* STEAP1 CRA b | EAW93751.1 | 259 | 88 |
| 30 | *H. sapiens* STEAP1 isofor | EAW93749.1 | 258 | 88 |

A multiple sequence alignment of *H. Sapiens* and *M. mulatta* STEAP1 sequences was generated with the consensus STEAP1 antigen 2. The STEAP1 antigen 2 consensus sequence (SEQ ID NO:12) is 94% homologous to full-length human isoforms (SEQ ID NO:26 and SEQ ID NO:27), 88% homologous to shorter *H. sapiens* isoforms (SEQ ID NO:29 and SEQ ID NO:30), and 94% homologous to *M. mulatta* full-length STEAP1 protein sequences (SEQ ID NO:28).

Example 7

A consensus PSCA antigen (SEQ ID NO:14) was generated. This sequence, which comprises 131 amino acids included the IgE leader sequence was compared to PSCA sequence set forth in Table 7. The PSCA sequence used was a full length human sequence. Table 7 includes the SEQ ID NO: and Accession number for the sequence used in the comparison with consensus PSCA antigen (SEQ ID NO:14).

TABLE 7

| SEQ ID NO | Species and protein | Accession Number | Number of amino acids | % homology to SEQ ID NO: 14 |
|---|---|---|---|---|
| 31 | *H. sapiens* PSCA | NP_005663.2 | 114 | 87 |

A multiple sequence alignment of *H. Sapiens* PSCA sequence (SEQ ID NO:31) was generated with the consensus PSCA antigen (SEQ ID NO:14). The PSCA antigen consensus sequence is 87% homologous to full-length *H. sapiens* PSCA.

Example 8

In vitro translation performed to confirm the expression of the PSA and PSMA antigens. The TNT® Quick Coupled Transcription/Translation System and 35S-methionine (Promega) were used. The pVAX vector alone (negative control) or pVAX backbone with the PSA or PSMA antigen inserts and 35S-methionine was added to the reaction mixture according to the manufacturer's instructions. The reaction was carried out at 30° C. for 2 hours. Labeled proteins were immunoprecipitated with anti-HA Affinity Gel (Sigma, St. Louis, Mo.) by rotation overnight in radioimmunoprecipitation assay (RIPA) buffer at 4° C. The immunoprecipitated proteins were electrophoresed on a SDS-PAGE gel that was subsequently fixed and dried. Expression of the 35S-labeled proteins was detected by autoradiography. The results are shown in FIG. 1.

Example 9

Cellular immunogenicity of the PSA and PSMA antigens was determined by Interferon-gamma ELISpot.

Female 4 to 6-week-old BALB/c mice were purchased from Jackson Laboratories (Bar Harbor, Me.). All animals were housed in a temperature-controlled, light-cycled facility at the University of Pennsylvania. Animal care was carried out according to the guidelines of the National Institutes of Health and the University of Pennsylvania Institutional Care and Use Committee.

For cellular immunogenicity studies, 10 or 20 µg of each antigen was delivered to the tibialis anterior muscle of Balb/c mice by intramuscular injection followed by electroporation using the CELLECTRA® adaptive constant current device (Inovio Pharmaceuticals, Inc., Blue Bell, Pa.). Mice (n=5 per group) received 2 immunizations at weeks 0 and 2. Two 0.1 Amp constant current square-wave pulses were delivered through a triangular 3-electrode array consisting of 26-gauge solid stainless steel electrodes. Each pulse was 52 milliseconds in length with a 1 second delay between pulses. The mice received a total of 2 immunizations that were administered 2 weeks apart. Mice were humanely sacrificed 1 week after the second immunization for analysis of cellular and humoral immune responses.

Figure 2A:
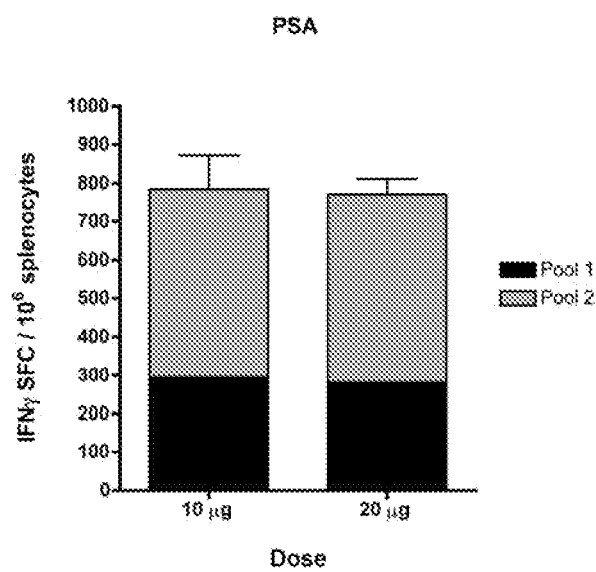
FIG. 2A shows cellular immunogenicity data. Cellular immunogenicity of PSA antigens was determined by Interferon-gamma ELISpot.
Figure 2B:
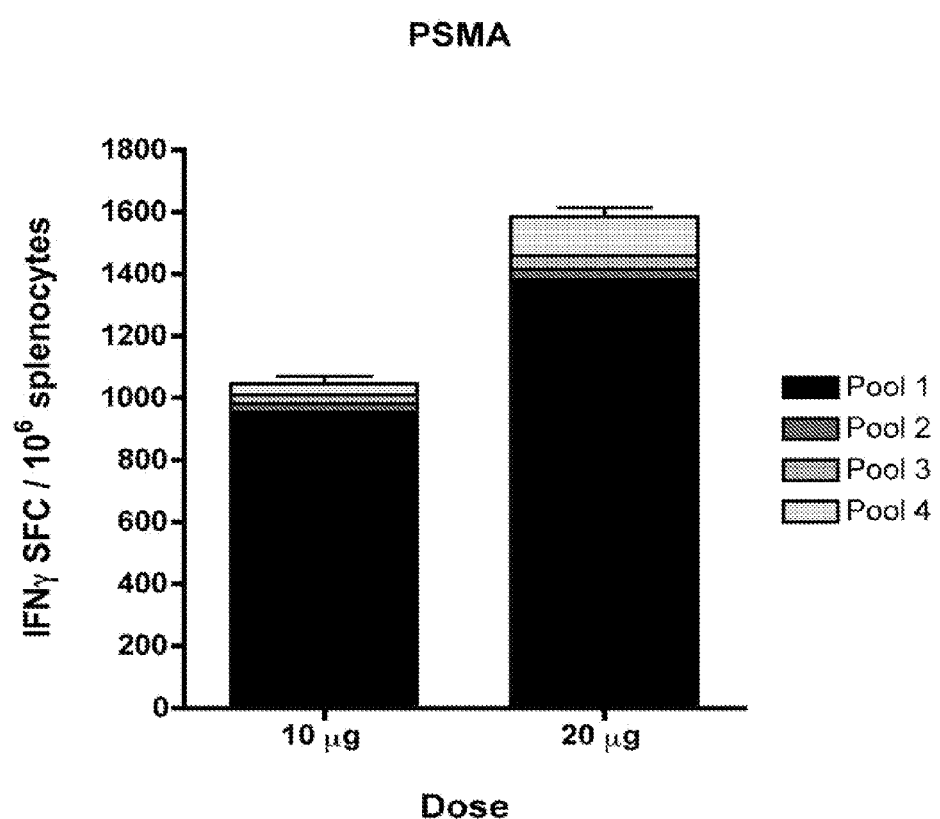
FIG. 2B shows cellular immunogenicity data. Cellular immunogenicity of PSA antigens was determined by Interferon-gamma ELISpot.

Cellular and responses were assessed 1 week after the last immunization (week 5). ELISpot analysis was used to determine antigen-specific secretion of IFNγ. Mouse IFNγ capture antibody (R&D Systems, Minneapolis, Minn.) was used to coat flat-bottom Immobilon-P plates (Millipore, Billerica, Mass.) overnight at 4° C. Splenocytes were aseptically isolated and resuspended at in R10 media (Rosewell Park Memorial Institute medium 1640 with supplemented with 10% fetal bovine serum, 1% antibiotic-antimycotic and 0.1% 2-mercaptoethanol). $2 \times 10^5$ splenocytes from immunized mice were added in to each well of the 96-well plate and stimulated overnight at 37° C., 5% CO2, in the presence of R10 (negative control), concanavalin A (positive control) (Sigma, St. Louis, Mo.) or antigen-specific peptide pools. The next day, mouse IFNγ detection antibody (R&D Systems, Minneapolis, Minn.) was added to the plates that were then incubated overnight at 4° C. The following day, streptavidin-ALP (MabTech, Sweden) was added to the plates for 2 hours and antigen-specific spots were visualized with BCIP/NPT substrate (MabTech, Sweden). PSA and PSMA peptides were 15-mer peptides spanning the entire length of the consensus immunogen, not including the HA tag or leader sequence, overlapping by 11 amino acids, and were synthesized by GenScript (Piscataway, N.J.). PSA and PSMA peptides were used at a final concentration of 1.0 µg/mL for each peptide. IFNγ ELISpot was used to evaluate antigen-specific cellular responses 1 week after the last immunization. For PSA, IFNγ responses were similar for the 10 µg (772.2+/−138.2 SFU) and 20 µg (771.1+/−155.2 SFU) vaccine doses (FIG. 2A). In contrast, there was a dose-dependant increase in PSMA-specific FNγ responses with 20 microgram of the vaccine (1585.0+/−194.0 SFU) as compared to 10 µg of the vaccine (1047.2+/−160.7 SFU) (FIG. 2B). Minimal background was observed for PSA or PSMA responses in naïve mice.

Example 10

Vaccine-Induced CD4+ and CD8+ T Cell Production of IFNγ, IL-2 and TNFα

Cellular immunogenicity was further characterized by flow cytometry for the co-delivery of the PSA and PSMA vaccines. Antigen-specific CD4+ and CD8+ T cell production of IFNγ, IL-2 and TNFα was determined for the total vaccine-specific response and the PSA and PSMA components of the total vaccine-specific response (n=5).

Cellular immune responses were also determined by intracellular cytokine staining and flow cytometry using the Cyto-Fix/CytoPerm kit per manufacteurer's instructions (BD Biosciences, San Diego, Calif.). Splenocytes harvested from immunized mice were washed with PBS and then resuspended in R10 media to a final concentration of 107 cells/ml. Cells were seeded in 96-well round bottom plates in a volume of 100 µl and an additional 100 µl of R10 media (negative control), media containing antigen-specific peptides pools or media containing phorbol myristate acetate (PMA, 10 ng/ml) and ionomycin (250 ng/ml; positive control) (Sigma, St. Louis, Mo.) was added and plates were incubated at 37° C., 5% CO2, for 6 hours. All stimulation media contained 1 µg/µL each of GolgiPlug and GolgiStop (BD Biosciences, San Diego, Calif.). At the end of the incubation period plates were spun down and washed twice with PBS. Cells were then stained with a violet dye for viability (LIVE/DEAD Violet Viability Dye, Invitrogen; Carlsbad, Calif.) for 30 minutes at 4° C. After washing as above with PBS, cells were stained externally for 30 minutes with anti-CD4 PerCPCy5.5 and anti-CD8 APC at 4° C., followed by fixing and permeabilization. Anti-CD3 PE-Cy5, anti-IL-2 PE, anti-IFNγ AlexaFluor-700 and anti-TNFα FITC (BD Biosciences, San Diego, Calif.) were added and cells were incubated again at 4° C. for 30 minutes. Cells were given a final wash with PBS and fixed in 1% PFA.

Figure 3A:
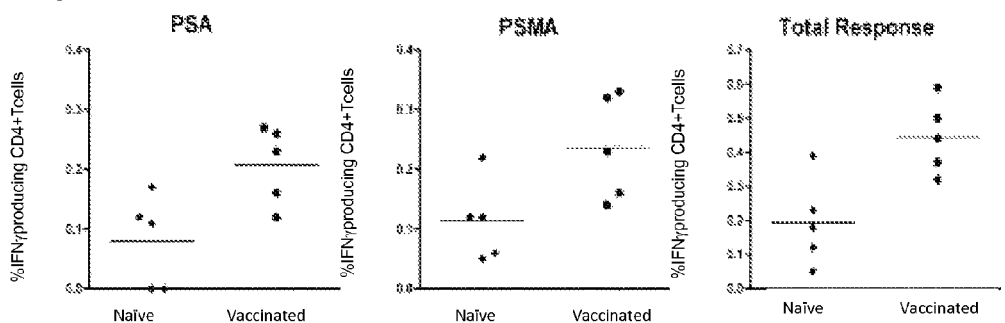
FIGS. 3A-C shows CD4+ T cell responses as characterized by flow cytometry by displaying graphs showing PSA-specific (left panel), PSMA-specific (middle panel) and total vaccine-specific (right panel) cytokine production: % IFNγ producing CD4+ T cells (FIG. 3A); % IL-2 producing CD4+ T cells (FIG. 3B); and % TNFα producing CD4+ T cells (FIG. 3C).
Figure 3B:
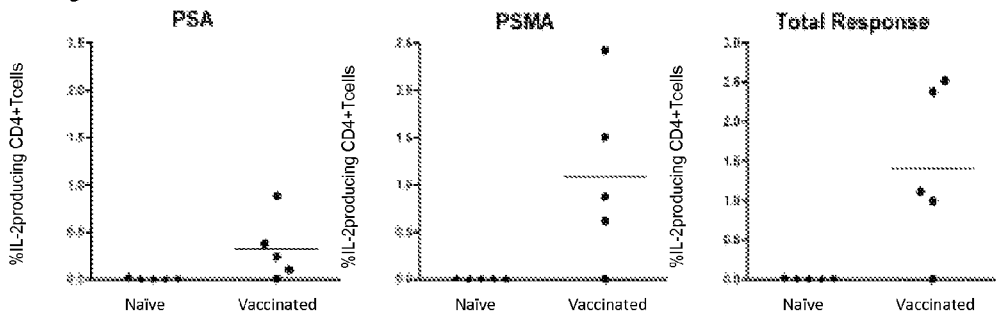
Figure 3C:
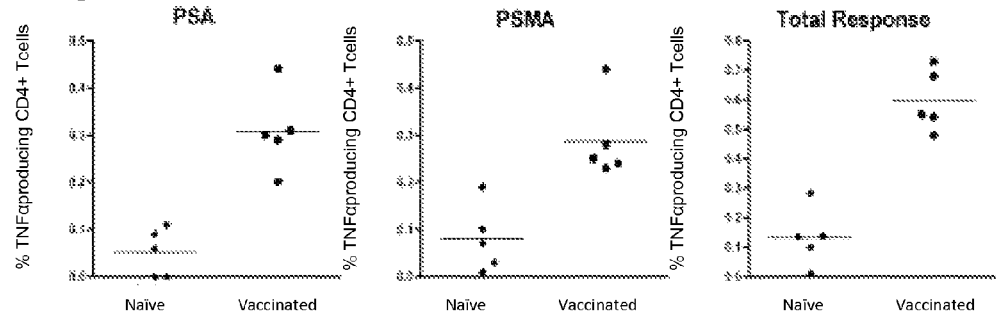

Co-delivery of the PSA and PSMA vaccine induced robust CD4+ secretion of IFNγ, IL-2 and TNFα. The percentage of PSA-specific (0.21%) and PSMA-specific (0.24%) IFNγ producing CD4+ T cells contributed equally to the total vaccine-specific CD4+ T cell IFNγ response (0.44%) (FIG. 3A). PSMA-specific CD4+ T cells producing IL-2 (1.08%) comprised the majority of the total percentage of CD4+ T cells producing vaccine-specific IL-2 (1.40%) (FIG. 3B). The percentage of PSA (0.31%) and PSMA (0.29%) induced CD4+ T cell production of TNFα contributed equally to the total vaccine-specific response (0.60%) (FIG. 3C). Overall, CD4+ T cell responses were well balanced between PSA and PSMA, with the exception of PSMA inducing the majority of the vaccine-specific CD4+ T cell IL-2 production.

Figure 4A:
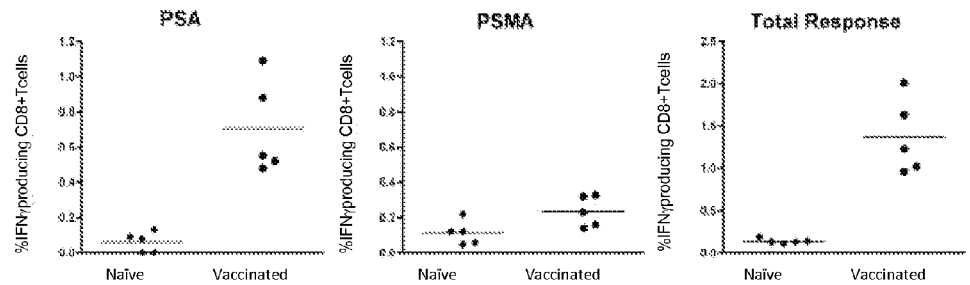
FIGS. 4A-C shows CD8+ T cell responses as characterized by flow cytometry by displaying graphs showing PSA-specific (left panel), PSMA-specific (middle panel) and total vaccine-specific (right panel) cytokine production: % IFNγ producing CD8+ T cells (FIG. 4A); % IL-2 producing CD8+ T cells (FIG. 4B); and % TNFα producing CD8+ T cells (FIG. 4C).
Figure 4B:
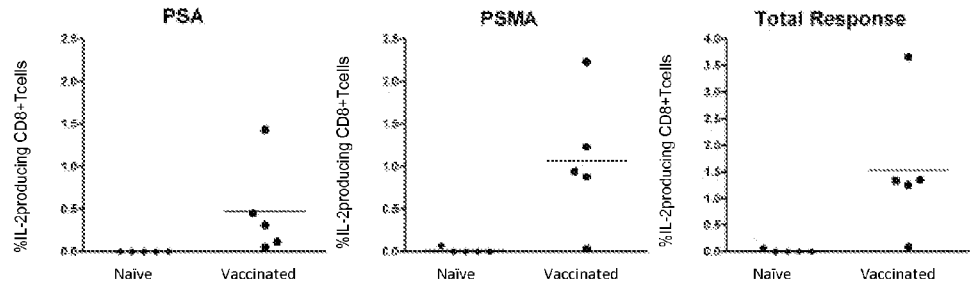
Figure 4C:
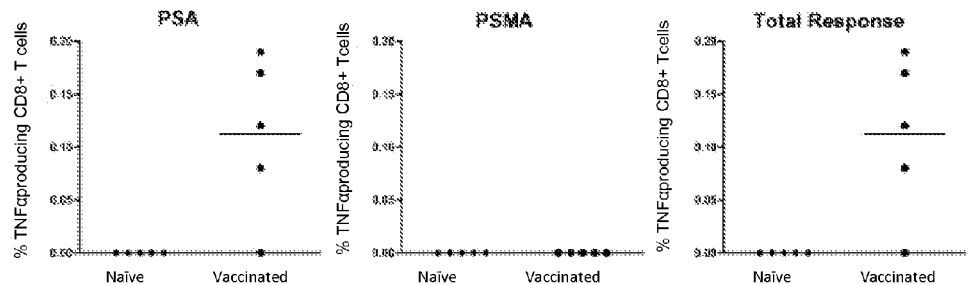

The vaccine induced strong antigen-specific CD8+ T cell production of IFNγ and IL-2 and, to a lesser extent, TNFα. Both PSA (0.70%) and PSMA (0.67%) induced robust CD8+ T cell IFNγ production. In fact, vaccine-specific CD8+ T cells secreting of IFNγ comprised 1.37% of the total CD8+ T cell population (FIG. 4A). The vaccine also induced a strong CD8+ T cell IL-2 response (1.54%). Similar to the CD4+ T cell IL-2 response, the percentage of PSMA-specific (1.06%) CD8+ T cells secreting IL-2 was approximately 2-fold higher than PSA-specific (0.47%) (FIG. 4B). The total percentage of vaccine-specific CD8+ T cell production of TNFα (0.11%) was in response to the PSA component of the vaccine (FIG. 4C). In summary, there was a high percentage of vaccine-specific CD8+ T cells production of IFNγ and IL-2. Similar to CD4+ T cell responses, IFNγ production was equally balanced between PSA and PSMA and the magnitude of the IL-2 PSMA-specific response was greater than that of the PSA-specific response.

Example 11

PSA-Specific IgG Seroconversion

Antibody response can play an important role in tumor immunotherapy. Accordingly we next examined this parameter of the immune response to the PSA antigen based on protein target availability.

Figure 5A:
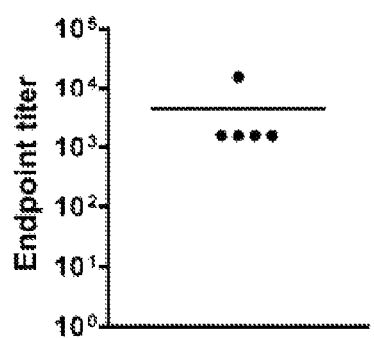
FIGS. 5A-B shows ELISA data for PSA-specific antibodies one week after the final immunization.
Figure 5B:
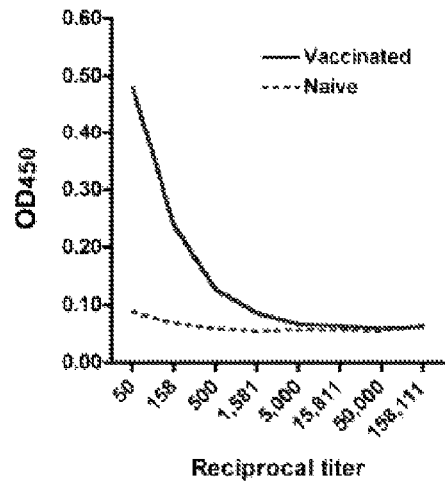

To determine PSA-specific sera antibody titers, 96-well Nunc-Immuno MaxiSorp plates (Nunc, Rochester, N.Y.) were coated overnight at 4° C. with 1 µg/well of recombinant PSA protein (Fitzgerald Industries, Acton, Mass.) diluted in PBS. Plates were washed with PBS, 0.05% Tween 20 (PBST), blocked for 1 hour at room temperature with 10% BSA/PBST, and incubated with serial dilutions of serum from immunized or naïve animals for 1 hour at room temperature. Plates were then washed 3 times with PBST and goat anti-mouse IgG (Santa Cruz, Santa Cruz, Calif.) was added a dilution of 1:5,000 in PBST. Bound enzyme was detected by SigmaFAST O-phenylenediamine dihydrochloride (OPD; Sigma-Aldrich, St. Louis, Mo.), and the optical density was determined at 450 nm on a Biotek (Winooski, Vt.) plate reader as shown in FIG. 5B. Endpoint titers were determined as previously described (Frey, A. et al. 1998). Briefly, the upper prediction limit was calculated using the Student t-distribution. The mathematical formula that defines the upper prediction limit is expressed as the standard deviation multiplied by a factor that was based on the number of negative controls (n=5) and the confidence level (95%). The endpoint titer was reported as the reciprocal of the last dilution above the upper predication limit.

In addition to conferring robust cellular-mediated immunity, the PSA vaccine also induced strong antigen-specific humoral responses. Antibody titers were determined by ELISA in sera isolated from mice one week after the last immunization (n=5). The vaccine induced an average PSA-specific antibody endpoint titer of 4,427 (range 1581-15,811) (FIG. 5A). The longevity of these responses may be important as well.

Example 12

Prostate specific antigen amino acid sequences available on GenBank include the following: gb_EAW71923.1_ H.sapiens_klk3_CRAb; _001639.1_ H.sapiens_PSA_iso1_preproprotein; gb_AAA59995.1_ H.sapiens_PSA_precursor; gb_AAA60193.1_ H.sapiens_PSA; gb_EAW71933.1_ H.sapiens_klk3_CRA_1; NP_001025218.1_ H.sapiens_PSA_iso3_preproprotein; gb_CAD54617.1_ H.sapiens_PSA; gb_CAD30844.1_H.sapiens_PSA; gb_AAA59996.1_H.sapiens_PSA_precursor; gb_AAD14185.1_H.sapiens_PSA; Q6DT45.1_M.fascicularis_KLK3; NP_001036241.1_M.mulatta_PSA_precursor; AAZ82258.1_M.mulatta_PSA; AAZ82255.1_G.gorilla_PSA; gi|1163838666|ref|NP_001106216.1|plasma kallikrein [Papio anubis]; gi|73746696|gb|AAZ82261.1|prostate specific antigen [Papio anubis]; i|73746692|gb|AAZ82259.1|prostate specific antigen [Erythrocebus patas]; gi|73746694|gb|AAZ82260.1|prostate specific antigen [Cercopithecus cephus]; gi|73746682|gb|AAZ82254.1|prostate specific antigen [Pan paniscus]; gi|73746680|gb|AAZ82253.1|prostate specific antigen [Pan troglodytes]; gi|73746686|gb|AAZ82256.1|prostate specific antigen [Pongo pygmaeus]; and 3746688|gb|AAZ82257.1|prostate specific antigen [Nomascus gabriellae].

PSMA amino acid sequences available on GenBank include the following: NP_004467.1_Human_GCPII_iso1; Human PSMA_AAC83972.1; M.mulatta_GCPII_iso1 XP_001096141.2; and M.mulatta_GCPII_iso2 XP_002799784.1.

STEAP amino acid sequences available on GenBank include the following: NP036581.1_Human_STEAP1; EAL24167.1_Human_STEAP1; XP001103605.1M.mulatta_STEAP1_iso3; EAW93751.1_HumanSTEAP1_CRAb; EAW93749.1_Human_STEAP1_CRAa; XP001164838.1_ P.troglodytes_STEAPiso2; XP002818311.1_P.abeli-i_STEAP1; NP001162459.1_P.anubis_STEAP1; NP_999470.1_S.scrofa_STEAP1; and NP_081675.2_M.musculusSTEAP1.

NP_005663.2_Human_PSCA is the accession number of a PSCA amino acid sequence available on GenBank.

The invention claimed is:

1. A protein selected from the group consisting of:
   a) SEQ ID NO:2, a protein that is 98% homologous to SEQ ID NO:2, provided amino acids 69, 78, 80, 82, 102, 110, 137, 139, 165, 189, 203, 220, 232 and 248 of SEQ ID NO:2 are conserved; or an immunogenic fragment of SEQ ID NO:2 comprising amino acids corresponding to at least 256 amino acid residues of SEQ ID NO:2, provided amino acids 69, 78, 80, 82, 102, 110, 137, 139, 165, 189, 203, 220, 232 and 248 of SEQ ID NO:2 are conserved;
   b) SEQ ID NO:4, a protein that is 98% homologous to SEQ ID NO:4, provided amino acids 21, 86, 127, 129, 154, 156, 182, 195, 206, 218, 220, 237, 249, 255, 265, 271 or 275 of SEQ ID NO:4 are conserved; or an immunogenic fragment of SEQ ID NO:4 comprising amino acids corresponding to at least 274 amino acid residues of SEQ ID NO:4, provided amino acids 21, 86, 127, 129, 154, 156, 182, 195, 206, 218, 220, 237, 249, 255, 265, 271 or 275 of SEQ ID NO:4 are conserved;
   c) SEQ ID NO:6; a protein that is 98% homologous to SEQ ID NO:6, provided amino acids 14, 15, 32, 47, 58, 79, 111, 157, 223, 320, 350, 475, 499, 569, 613, 624, 653, 660, 663, 733 and 734 of SEQ ID NO:6 are conserved; or an immunogenic fragment of SEQ ID NO:6 comprising amino acids corresponding to at least 735 amino acid residues of SEQ ID NO:6, provided amino acids 14, 15, 32, 47, 58, 79, 111, 157, 223, 320, 350, 475, 499, 569, 613, 624, 653, 660, 663, 733 and 734 of SEQ ID NO:6 are conserved; and
   d) SEQ ID NO:8, a protein that is 98% homologous to SEQ ID NO:8, provided amino acids 21, 31, 32, 49, 64, 75, 96, 128, 174, 240, 337, 367, 492, 516, 565, 586, 630, 641, 670, 677, 680, 750, and 751 of SEQ ID NO:8 are conserved, or an immunogenic fragment of SEQ ID NO:8 comprising amino acids corresponding to at least 752 amino acid residues of SEQ ID NO:8, provided amino acids 21, 31, 32, 49, 64, 75, 96, 128, 174, 240, 337, 367, 492, 516, 565, 586, 630 641 670 677 680 750 and 751 of SEQ ID NO:8 are conserved.

2. The protein of claim 1 selected from the group comprising: at least one selected from either elements a) or b), and at least one selected from either elements c) or d).

3. The protein of claim 1 encoding a protein selected from the group comprising: SEQ ID NO:2; SEQ ID NO:4; SEQ ID NO:6; or SEQ ID NO:8.

* * * * *

SEQUENCE LISTING

```
<160> NUMBER OF SEQ ID NOS: 32

<210> SEQ ID NO 1
<211> LENGTH: 789
<212> TYPE: DNA
<213> ORGANISM: Artificial Sequence
<220> FEATURE:
<223> OTHER INFORMATION: PSA antigen 1 nucleic acid consensus sequence

<400> SEQUENCE: 1
atgtgggtcc tggtggtgtt cctgactctg agcgtcacat ggatcggcgc cgctccactg      60
attctgagcc gcctggtggg cgggtgggag tgcgaaaagc actcccagcc atggcaggtg     120
ctggtcgctt ctagggccg agcagtgtgc ggaggcgtgc tggtccaccc tcagtgggtc      180
ctgaccgcag cccattgtat ccgacagaag agcgtgattc tgctggggcg acaccagcca     240
ttctaccccg aggacacagg acaggtgttc caggtctctc acagttttcc ccatcctctg     300
tacaacatga gcctgctgaa aaacagatat ctgggacctg gcgacgatag ctcccatgat     360
```

```
ctgatgctgc tgaggctgtc cgagccagcc gaactgactg acgctgtgca ggtcctggat    420
ctgcccaccc aggagcctgc cctgggaacc acatgttatg cttcaggctg ggggagcatc    480
gaaccagagg aacatctgac tcccaagaaa ctgcagtgcg tggacctgca cctgattagt    540
aacgatgtgt gtgcacaggt ccattcacag aaggtgacaa agttcatgct gtgcgccggc    600
tcttggatgg gcggcaagtc aacttgcagc ggggactccg gcgggccact ggtgtgtgat    660
ggagtcctgc agggcatcac ctcttggggc agtcagcctt gtgccctgcc tcggagacca    720
agtctgtaca ctaaggtggt ccggtatagg aaatggattc aggacactat tgccgctaac    780
ccctgataa                                                            789

<210> SEQ ID NO 2
<211> LENGTH: 261
<212> TYPE: PRT
<213> ORGANISM: Artificial Sequence
<220> FEATURE:
<223> OTHER INFORMATION: PSA antigen 1 amino acid consensus sequence

<400> SEQUENCE: 2

Met Trp Val Leu Val Val Phe Leu Thr Leu Ser Val Thr Trp Ile Gly
 1               5                  10                  15

Ala Ala Pro Leu Ile Leu Ser Arg Leu Val Gly Gly Trp Glu Cys Glu
                20                  25                  30

Lys His Ser Gln Pro Trp Gln Val Leu Val Ala Ser Arg Gly Arg Ala
            35                  40                  45

Val Cys Gly Gly Val Leu Val His Pro Gln Trp Val Leu Thr Ala Ala
        50                  55                  60

His Cys Ile Arg Gln Lys Ser Val Ile Leu Leu Gly Arg His Gln Pro
65                  70                  75                  80

Phe Tyr Pro Glu Asp Thr Gly Gln Val Phe Gln Val Ser His Ser Phe
                85                  90                  95

Pro His Pro Leu Tyr Asn Met Ser Leu Leu Lys Asn Arg Tyr Leu Gly
               100                 105                 110

Pro Gly Asp Asp Ser Ser His Asp Leu Met Leu Leu Arg Leu Ser Glu
           115                 120                 125

Pro Ala Glu Leu Thr Asp Ala Val Gln Val Leu Asp Leu Pro Thr Gln
       130                 135                 140

Glu Pro Ala Leu Gly Thr Thr Cys Tyr Ala Ser Gly Trp Gly Ser Ile
145                 150                 155                 160

Glu Pro Glu Glu His Leu Thr Pro Lys Lys Leu Gln Cys Val Asp Leu
               165                 170                 175

His Leu Ile Ser Asn Asp Val Cys Ala Gln Val His Ser Gln Lys Val
           180                 185                 190

Thr Lys Phe Met Leu Cys Ala Gly Ser Trp Met Gly Gly Lys Ser Thr
       195                 200                 205

Cys Ser Gly Asp Ser Gly Gly Pro Leu Val Cys Asp Gly Val Leu Gln
210                 215                 220

Gly Ile Thr Ser Trp Gly Ser Gln Pro Cys Ala Leu Pro Arg Arg Pro
225                 230                 235                 240

Ser Leu Tyr Thr Lys Val Val Arg Tyr Arg Lys Trp Ile Gln Asp Thr
               245                 250                 255

Ile Ala Ala Asn Pro
           260
```

<210> SEQ ID NO 3
<211> LENGTH: 840
<212> TYPE: DNA
<213> ORGANISM: Artificial Sequence
<220> FEATURE:
<223> OTHER INFORMATION: PSA antigen 2 nucleic acid consensus sequence

<400> SEQUENCE: 3

```
atggactgga catggattct gttcctggtc gccgccgcaa ctcgcgtgca ttcctgggtc    60
ctggtggtgt tcctgactct gagcgtcaca tggatcggcg ccgctccact gattctgagc   120
cgcctggtgg gcgggtggga gtgcgaaaag cactcccagc catggcaggt gctggtcgct   180
tctaggggcc gagcagtgtg cggaggcgtg ctggtccacc ctcagtgggt cctgaccgca   240
gcccattgta tccgacagaa gagcgtgatt ctgctggggc gacaccagcc attctacccc   300
gaggacacag acaggtgttt ccaggtctct cacagttttc cccatcctct gtacaacatg   360
agcctgctga aaacagata tctgggacct ggcgacgata gctcccatga tctgatgctg   420
ctgaggctgt ccgagccagc cgaactgact gacgctgtgc aggtcctgga tctgcccacc   480
caggagcctg ccctgggaac cacatgttat gcttcaggct ggggagcat cgaaccagag   540
gaacatctga ctcccaagaa actgcagtgc gtggacctgc acctgattag taacgatgtg   600
tgtgcacagg tccattcaca gaaggtgaca aagttcatgc tgtgcgccgg ctcttggatg   660
ggcggcaagt caacttgcag cggggactcc ggcgggccac tggtgtgtga tggagtcctg   720
cagggcatca cctcttgggg cagtcagcct tgtgccctgc ctcggagacc aagtctgtac   780
actaaggtgg tccggtatag gaatggatt caggacacta ttgccgctaa cccctgataa   840
```

<210> SEQ ID NO 4
<211> LENGTH: 278
<212> TYPE: PRT
<213> ORGANISM: Artificial Sequence
<220> FEATURE:
<223> OTHER INFORMATION: PSA antigen 2 amino acid consensus sequence

<400> SEQUENCE: 4

```
Met Asp Trp Thr Trp Ile Leu Phe Leu Val Ala Ala Ala Thr Arg Val
1               5                   10                  15

His Ser Trp Val Leu Val Val Phe Leu Thr Leu Ser Val Thr Trp Ile
            20                  25                  30

Gly Ala Ala Pro Leu Ile Leu Ser Arg Leu Val Gly Gly Trp Glu Cys
        35                  40                  45

Glu Lys His Ser Gln Pro Trp Gln Val Leu Val Ala Ser Arg Gly Arg
    50                  55                  60

Ala Val Cys Gly Gly Val Leu Val His Pro Gln Trp Val Leu Thr Ala
65                  70                  75                  80

Ala His Cys Ile Arg Gln Lys Ser Val Ile Leu Leu Gly Arg His Gln
                85                  90                  95

Pro Phe Tyr Pro Glu Asp Thr Gly Gln Val Phe Gln Val Ser His Ser
            100                 105                 110

Phe Pro His Pro Leu Tyr Asn Met Ser Leu Leu Lys Asn Arg Tyr Leu
        115                 120                 125

Gly Pro Gly Asp Asp Ser Ser His Asp Leu Met Leu Leu Arg Leu Ser
    130                 135                 140

Glu Pro Ala Glu Leu Thr Asp Ala Val Gln Val Leu Asp Leu Pro Thr
145                 150                 155                 160

Gln Glu Pro Ala Leu Gly Thr Thr Cys Tyr Ala Ser Gly Trp Gly Ser
                165                 170                 175
```

```
Ile Glu Pro Glu Glu His Leu Thr Pro Lys Lys Leu Gln Cys Val Asp
            180                 185                 190

Leu His Leu Ile Ser Asn Asp Val Cys Ala Gln Val His Ser Gln Lys
            195                 200                 205

Val Thr Lys Phe Met Leu Cys Ala Gly Ser Trp Met Gly Gly Lys Ser
            210                 215                 220

Thr Cys Ser Gly Asp Ser Gly Gly Pro Leu Val Cys Asp Gly Val Leu
225                 230                 235                 240

Gln Gly Ile Thr Ser Trp Gly Ser Gln Pro Cys Ala Leu Pro Arg Arg
                245                 250                 255

Pro Ser Leu Tyr Thr Lys Val Val Arg Tyr Arg Lys Trp Ile Gln Asp
            260                 265                 270

Thr Ile Ala Ala Asn Pro
            275

<210> SEQ ID NO 5
<211> LENGTH: 2283
<212> TYPE: DNA
<213> ORGANISM: Artificial Sequence
<220> FEATURE:
<223> OTHER INFORMATION: PSMA antigen 1 nucleic acid consensus sequence

<400> SEQUENCE: 5
atgtggaacg cactgcatga gactgattct gctgtcgcac tgggacggag accccggtgg       60
ctgtgcgctg gagcactggt gctggccggc gggggattcc tgctgggatt cctgtttggc      120
tggtttatca aaagctccag cgaggctacc aatattaccc ctaagcacaa taagaaagca      180
ttcctggatg aactgaaagc cgagaacatc aagaaattcc tgtacaactt cacaagaatt      240
ccacatctgg ctggcactga gcagaacttc agctggcaa acagatcca gagtcagtgg       300 aaggaatttg gctggactc agtggagctg acccactacg atgtcctgct gtcctatcca      360
aataagactc atcccaacta catctctatc attaacgaag acggaaatga gattttcaac      420
acctctctgt ttgaaccccc tccacccggc tatgagaatg tcagtgacgt ggtccctcca      480
ttctcagcct tcagccccca ggggatgcct gaggagatc tggtgtacgt caattatgct      540
agaacagaag acttctttaa gctggagagg gatatgaaaa tcaactgttc cggcaagatc      600
gtgattgccc ggtacgggaa ggtgttcaga ggaaataagg tcaaaaacgc tcagctggcc      660
ggagctaccg gcgtgatcct gtacagcgac cccgctgatt attttgcacc tggcgtgaag      720
tcctatccag acggatggaa tctgcccggc ggggagtgc agaggggaaa catcctgaac      780
ctgaatggag ccggcgatcc tctgactcca ggataccccg ccaacgaata cgcttatcgc      840
cggggaattg cagaggccgt gggcctgcct agcatcccag tccatcccat ggctatac       900 gatgcccaga gctgctgga gaaaatgggc gggagcgctc cccctgactc tagttggaag      960
ggctccctga agtgcctta caatgtcggg ccaggattca ctgggaactt ttctacccag     1020
aaggtgaaaa tgcacatcca tagtaccagc gaggtgacac gaatctacaa cgtcattggc     1080
accctgagag gcgccgtgga gcctgatcgc tatgtcattc tgggaggcca cagagactca     1140
tgggtgttcg gggaatcga tccacagagc ggagcagctg tggtccatga aattgtgcgc     1200
agctttggga ccctgaagaa agagggatgg cgacccaggc gcacaatcct gttcgcatcc     1260
tgggacgccg aggaatttgg ctgctgggc agcacagaat gggccgagga aattctcgc      1320 ctgctgcagg agcgagggt ggcttacatc aatgcagact caagcattga aggaaactat     1380
accctgcggg tggattgcac accctgatg tacagtctgg tctataacct gacaaaggag     1440
```

```
ctgaaatcac ctgacgaggg cttcgaaggg aaaagcctgt acgaatcctg gactgagaag    1500
agcccatccc ccgaattcag cggcatgcct aggatctcta agctgggcag tgggaacgat    1560
tttgaggtgt tctttcagcg cctgggaatt gcctctggcc gagctcggta cacaaaaaat    1620
tgggagacta acaagttctc ctcttaccca ctgtatcaca gcgtgtacga gacttatgaa    1680
ctggtcgaga aattctacga ccccactttt aagtatcatc tgaccgtggc acaggtcagg    1740
ggcgggatgg tgttcgaact ggccaatagc atcgtcctgc catttgactg tcgagattac    1800
gctgtggtcc tgcggaagta cgcagacaag atctataaca tctccatgaa gcaccccccag   1860 gagatgaagg cctattctgt gagtttcgat tccctgtttt ctgccgtcaa aaatttcacc    1920
gaaatcgcta gtaagttttc agagcgcctg caggacctgg ataagtccaa tcccatcctg    1980
ctgcggatta tgaacgatca gctgatgttc ctggaaagag cctttatcga ccctctgggc    2040
ctgcctgata gaccattcta caggcacgtg atctacgcac tagttcaca taacaagtac     2100 gccggcgagt ctttcccagg gatctatgac gctctgtttg atattgaatc aaaggtggac    2160
cccagcaaag catggggcga ggtcaagaga cagatcagca ttgcagcctt tacagtgcag    2220
gccgccgccg aaaccctgtc cgaagtcgct tacccatacg atgtccccga ttacgcatga    2280
taa                                                                  2283
```

<210> SEQ ID NO 6
<211> LENGTH: 750
<212> TYPE: PRT
<213> ORGANISM: Artificial Sequence
<220> FEATURE:
<223> OTHER INFORMATION: PSMA antigen 1 amino acid consensus sequence

<400> SEQUENCE: 6

```
Met Trp Asn Ala Leu His Glu Thr Asp Ser Ala Val Ala Leu Gly Arg
1               5                   10                  15

Arg Pro Arg Trp Leu Cys Ala Gly Ala Leu Val Leu Ala Gly Gly Gly
            20                  25                  30

Phe Leu Leu Gly Phe Leu Phe Gly Trp Phe Ile Lys Ser Ser Ser Glu
        35                  40                  45

Ala Thr Asn Ile Thr Pro Lys His Asn Lys Lys Ala Phe Leu Asp Glu
    50                  55                  60

Leu Lys Ala Glu Asn Ile Lys Lys Phe Leu Tyr Asn Phe Thr Arg Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Thr His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Gly Tyr Glu Asn Val Ser Asp Val Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205
```

```
Phe Arg Gly Asn Lys Val Lys Asn Ala Gln Leu Ala Gly Ala Thr Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
                245                 250                 255

Asn Ile Leu Asn Leu Asn Gly Ala Gly Asp Pro Leu Thr Pro Gly Tyr
                260                 265                 270

Pro Ala Asn Glu Tyr Ala Tyr Arg Arg Gly Ile Ala Glu Ala Val Gly
            275                 280                 285

Leu Pro Ser Ile Pro Val His Pro Ile Gly Tyr Tyr Asp Ala Gln Lys
290                 295                 300

Leu Leu Glu Lys Met Gly Gly Ser Ala Pro Pro Asp Ser Ser Trp Lys
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Ser Glu Val
                340                 345                 350

Thr Arg Ile Tyr Asn Val Ile Gly Thr Leu Arg Gly Ala Val Glu Pro
            355                 360                 365

Asp Arg Tyr Val Ile Leu Gly Gly His Arg Asp Ser Trp Val Phe Gly
    370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
                420                 425                 430

Glu Trp Ala Glu Glu Asn Ser Arg Leu Leu Gln Glu Arg Gly Val Ala
            435                 440                 445

Tyr Ile Asn Ala Asp Ser Ser Ile Glu Gly Asn Tyr Thr Leu Arg Val
    450                 455                 460

Asp Cys Thr Pro Leu Met Tyr Ser Leu Val Tyr Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Glu Lys Ser Pro Ser Pro Glu Phe Ser Gly Met Pro Arg Ile
                500                 505                 510

Ser Lys Leu Gly Ser Gly Asn Asp Phe Glu Val Phe Phe Gln Arg Leu
            515                 520                 525

Gly Ile Ala Ser Gly Arg Ala Arg Tyr Thr Lys Asn Trp Glu Thr Asn
    530                 535                 540

Lys Phe Ser Ser Tyr Pro Leu Tyr His Ser Val Tyr Glu Thr Tyr Glu
545                 550                 555                 560

Leu Val Glu Lys Phe Tyr Asp Pro Thr Phe Lys Tyr His Leu Thr Val
                565                 570                 575

Ala Gln Val Arg Gly Gly Met Val Phe Glu Leu Ala Asn Ser Ile Val
                580                 585                 590

Leu Pro Phe Asp Cys Arg Asp Tyr Ala Val Val Leu Arg Lys Tyr Ala
            595                 600                 605

Asp Lys Ile Tyr Asn Ile Ser Met Lys His Pro Gln Glu Met Lys Ala
    610                 615                 620
```

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Leu Asp Lys Ser
            645                 650                 655

Asn Pro Ile Leu Leu Arg Ile Met Asn Asp Gln Leu Met Phe Leu Glu
                660                 665                 670

Arg Ala Phe Ile Asp Pro Leu Gly Leu Pro Asp Arg Pro Phe Tyr Arg
            675                 680                 685

His Val Ile Tyr Ala Pro Ser Ser His Asn Lys Tyr Ala Gly Glu Ser
        690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Ser Ile Ala Ala
                725                 730                 735

Phe Thr Val Gln Ala Ala Ala Glu Thr Leu Ser Glu Val Ala
            740                 745                 750

<210> SEQ ID NO 7
<211> LENGTH: 2334
<212> TYPE: DNA
<213> ORGANISM: Artificial Sequence
<220> FEATURE:
<223> OTHER INFORMATION: PSMA antigen 2 nucleic acid consensus sequence

<400> SEQUENCE: 7

```
atggactgga catggattct gttcctggtc gccgccgcaa ctcgcgtgca ttcctggaac      60
gcactgcatg agactgattc tgctgtcgca ctgggacgga gaccccggtg gctgtgcgct     120
ggagcactgg tgctggccgg cgggggattc ctgctgggat tcctgtttgg ctggtttatc     180
aaaagctcca gcgaggctac caatattacc cctaagcaca ataagaaagc attcctggat     240
gaactgaaag ccgagaacat caagaaattc ctgtacaact tcacaagaat ccacatctg      300 gctggcactg agcagaactt ccagctggca aacagatcc agagtcagtg aaggaatt       360 gggctggact cagtggagct gacccactac gatgtcctgc tgtcctatcc aaataagact     420
catcccaact acatctctat cattaacgaa gacggaaatg agattttcaa cacctctctg     480
tttgaacccc ctccacccgg ctatgagaat gtcagtgacg tggtccctcc attctcagcc     540
ttcagccccc aggggatgcc tgagggagat ctggtgtacg tcaattatgc tagaacagaa     600
gacttcttta agctggagag ggatatgaaa atcaactgtt ccggcaagat cgtgattgcc     660
cggtacggga aggtgttcag aggaaataag gtcaaaaacg ctcagctggc cggagctacc     720
ggcgtgatcc tgtacagcga ccccgctgat tattttgcac ctggcgtgaa gtcctatcca     780
gacggatgga tctgcccggg cggggagtg cagaggggaa acatcctgaa cctgaatgga     840
gccggcgatc ctctgactcc aggataccc gccaacgaat acgcttatcg ccggggaatt     900
gcagaggccg tgggcctgcc tagcatccca gtccatccca ttggctatta cgatgcccag     960
aagctgctgg agaaaatggg cgggagcgct ccccctgact agttggaa gggctccctg    1020 aaagtgcctt acaatgtcgg gccaggattc actgggaact tttctaccca gaaggtgaaa    1080
atgcacatcc atagtaccag cgaggtgaca cgaatctaca cgtcattgg caccctgaga    1140 ggcgccgtgg agcctgatcg ctatgtcatt ctgggaggcc acagagactc atgggtgttc    1200
gggggaatcg atccacagag cggagcagct gtggtccatg aaattgtgcg cagctttggg    1260
accctgaaga agagggatg cgacccagg cgcacaatcc tgttcgcatc ctgggacgcc    1320
gaggaatttg gctgctggg cagcacagaa tgggccgagg aaaattctcg cctgctgcag    1380
```

```
gagcgagggg tggcttacat caatgcagac tcaagcattg aaggaaacta tacccctgcgg   1440
gtggattgca caccccctgat gtacagtctg gtctataacc tgacaaagga gctgaaatca   1500
cctgacgagg gcttcgaagg gaaaagcctg tacgaatcct ggactgagaa gagcccatcc   1560
cccgaattca gcggcatgcc taggatctct aagctgggca gtgggaacga ttttgaggtg   1620
ttctttcagc gcctgggaat tgcctctggc cgagctcggt acacaaaaaa ttgggagact   1680
aacaagttct cctcttaccc actgtatcac agcgtgtacg agacttatga actggtcgag   1740
aaattctacg accccacttt taagtatcat ctgaccgtgg cacaggtcag gggcgggatg   1800
gtgttcgaac tggccaatag catcgtcctg ccatttgact gtcgagatta cgctgtggtc   1860
ctgcggaagt acgcagacaa gatctataac atctccatga agcaccccca ggagatgaag   1920
gcctattctg tgagtttcga ttccctgttt tctgccgtca aaaatttcac cgaaatcgct   1980
agtaagtttt cagagcgcct gcaggacctg gataagtcca atcccatcct gctgcggatt   2040
atgaacgatc agctgatgtt cctggaaaga gcctttatcg accctctggg cctgcctgat   2100
agaccattct acaggcacgt gatctacgca cctagttcac ataacaagta cgccggcgag   2160
tctttcccag ggatctatga cgctctgttt gatattgaat caaaggtgga ccccagcaaa   2220
gcatggggcg aggtcaagag acagatcagc attgcagcct ttacagtgca ggccgccgcc   2280
gaaaccctgt ccgaagtcgc ttacccatac gatgtccccg attacgcatg ataa         2334
```

<210> SEQ ID NO 8
<211> LENGTH: 767
<212> TYPE: PRT
<213> ORGANISM: Artificial Sequence
<220> FEATURE:
<223> OTHER INFORMATION: PSMA antigen 2 amino acid consensus sequence

<400> SEQUENCE: 8

```
Met Asp Trp Thr Trp Ile Leu Phe Leu Val Ala Ala Thr Arg Val
1               5                   10                  15

His Ser Trp Asn Ala Leu His Glu Thr Asp Ser Ala Val Ala Leu Gly
            20                  25                  30

Arg Arg Pro Arg Trp Leu Cys Ala Gly Ala Leu Val Leu Ala Gly Gly
        35                  40                  45

Gly Phe Leu Leu Gly Phe Leu Phe Gly Trp Phe Ile Lys Ser Ser Ser
    50                  55                  60

Glu Ala Thr Asn Ile Thr Pro Lys His Asn Lys Lys Ala Phe Leu Asp
65                  70                  75                  80

Glu Leu Lys Ala Glu Asn Ile Lys Lys Phe Leu Tyr Asn Phe Thr Arg
                85                  90                  95

Ile Pro His Leu Ala Gly Thr Glu Gln Asn Phe Gln Leu Ala Lys Gln
            100                 105                 110

Ile Gln Ser Gln Trp Lys Glu Phe Gly Leu Asp Ser Val Glu Leu Thr
        115                 120                 125

His Tyr Asp Val Leu Leu Ser Tyr Pro Asn Lys Thr His Pro Asn Tyr
    130                 135                 140

Ile Ser Ile Ile Asn Glu Asp Gly Asn Glu Ile Phe Asn Thr Ser Leu
145                 150                 155                 160

Phe Glu Pro Pro Pro Gly Tyr Glu Asn Val Ser Asp Val Val Pro
                165                 170                 175

Pro Phe Ser Ala Phe Ser Pro Gln Gly Met Pro Glu Gly Asp Leu Val
            180                 185                 190
```

-continued

```
Tyr Val Asn Tyr Ala Arg Thr Glu Asp Phe Phe Lys Leu Glu Arg Asp
            195                 200                 205
Met Lys Ile Asn Cys Ser Gly Lys Ile Val Ile Ala Arg Tyr Gly Lys
    210                 215                 220
Val Phe Arg Gly Asn Lys Val Lys Asn Ala Gln Leu Ala Gly Ala Thr
225                 230                 235                 240
Gly Val Ile Leu Tyr Ser Asp Pro Ala Asp Tyr Phe Ala Pro Gly Val
                245                 250                 255
Lys Ser Tyr Pro Asp Gly Trp Asn Leu Pro Gly Gly Val Gln Arg
            260                 265                 270
Gly Asn Ile Leu Asn Leu Asn Gly Ala Gly Asp Pro Leu Thr Pro Gly
            275                 280                 285
Tyr Pro Ala Asn Glu Tyr Ala Tyr Arg Arg Gly Ile Ala Glu Ala Val
    290                 295                 300
Gly Leu Pro Ser Ile Pro Val His Pro Ile Gly Tyr Tyr Asp Ala Gln
305                 310                 315                 320
Lys Leu Leu Glu Lys Met Gly Ser Ala Pro Pro Asp Ser Ser Trp
                325                 330                 335
Lys Gly Ser Leu Lys Val Pro Tyr Asn Val Gly Pro Gly Phe Thr Gly
            340                 345                 350
Asn Phe Ser Thr Gln Lys Val Lys Met His Ile His Ser Thr Ser Glu
    355                 360                 365
Val Thr Arg Ile Tyr Asn Val Ile Gly Thr Leu Arg Gly Ala Val Glu
    370                 375                 380
Pro Asp Arg Tyr Val Ile Leu Gly Gly His Arg Asp Ser Trp Val Phe
385                 390                 395                 400
Gly Gly Ile Asp Pro Gln Ser Gly Ala Ala Val Val His Glu Ile Val
                405                 410                 415
Arg Ser Phe Gly Thr Leu Lys Lys Glu Gly Trp Arg Pro Arg Arg Thr
                420                 425                 430
Ile Leu Phe Ala Ser Trp Asp Ala Glu Glu Phe Gly Leu Leu Gly Ser
            435                 440                 445
Thr Glu Trp Ala Glu Glu Asn Ser Arg Leu Leu Gln Glu Arg Gly Val
    450                 455                 460
Ala Tyr Ile Asn Ala Asp Ser Ser Ile Glu Gly Asn Tyr Thr Leu Arg
465                 470                 475                 480
Val Asp Cys Thr Pro Leu Met Tyr Ser Leu Val Tyr Asn Leu Thr Lys
                485                 490                 495
Glu Leu Lys Ser Pro Asp Glu Gly Phe Glu Gly Lys Ser Leu Tyr Glu
            500                 505                 510
Ser Trp Thr Glu Lys Ser Pro Ser Pro Glu Phe Ser Gly Met Pro Arg
            515                 520                 525
Ile Ser Lys Leu Gly Ser Gly Asn Asp Phe Glu Val Phe Phe Gln Arg
            530                 535                 540
Leu Gly Ile Ala Ser Gly Arg Ala Arg Tyr Thr Lys Asn Trp Glu Thr
545                 550                 555                 560
Asn Lys Phe Ser Ser Tyr Pro Leu Tyr His Ser Val Tyr Glu Thr Tyr
                565                 570                 575
Glu Leu Val Glu Lys Phe Tyr Asp Pro Thr Phe Lys Tyr His Leu Thr
            580                 585                 590
Val Ala Gln Val Arg Gly Gly Met Val Phe Glu Leu Ala Asn Ser Ile
            595                 600                 605
Val Leu Pro Phe Asp Cys Arg Asp Tyr Ala Val Val Leu Arg Lys Tyr
```

Ala Asp Lys Ile Tyr Asn Ile Ser Met Lys His Pro Gln Glu Met Lys
625                 630                 635                 640

Ala Tyr Ser Val Ser Phe Asp Ser Leu Phe Ser Ala Val Lys Asn Phe
            645                 650                 655

Thr Glu Ile Ala Ser Lys Phe Ser Glu Arg Leu Gln Asp Leu Asp Lys
                660                 665                 670

Ser Asn Pro Ile Leu Leu Arg Ile Met Asn Asp Gln Leu Met Phe Leu
            675                 680                 685

Glu Arg Ala Phe Ile Asp Pro Leu Gly Leu Pro Asp Arg Pro Phe Tyr
690                 695                 700

Arg His Val Ile Tyr Ala Pro Ser Ser His Asn Lys Tyr Ala Gly Glu
705                 710                 715                 720

Ser Phe Pro Gly Ile Tyr Asp Ala Leu Phe Asp Ile Glu Ser Lys Val
                725                 730                 735

Asp Pro Ser Lys Ala Trp Gly Glu Val Lys Arg Gln Ile Ser Ile Ala
                740                 745                 750

Ala Phe Thr Val Gln Ala Ala Ala Glu Thr Leu Ser Glu Val Ala
            755                 760                 765

<210> SEQ ID NO 9
<211> LENGTH: 1023
<212> TYPE: DNA
<213> ORGANISM: Artificial Sequence
<220> FEATURE:
<223> OTHER INFORMATION: STEAP antigen 1 nucleic acid consensus sequence

<400> SEQUENCE: 9
atggagagcc gcaaggacat cacaaatcag gaagagctgt ggaagatgaa accacggaga    60
aacctggagg aagacgatta cctgcacaag gacaccggcg aaacaagtat gctgaaaaga   120
ccagtgctgc tgcacctgca tcagactgct catgcagacg agtttgattg ccccctctga   180
ctgcagcaca cccaggagct gttcccacag tggcatctgc ccatcaagat tgccgctatc   240
attgcttcac tgacatttct gtatactctg ctgagagaag tgatccaccc tctggccacc   300
agccatcagc agtacttcta taagatccct attctggtca tcaacaaggt cctgccaatg   360
gtgagcatca cactgctggc cctggtctac ctgcctggcg tgatcgcagc cattgtccag   420
ctgcacaacg gaacaaagta caagaagttc ccacattggc tggataagtg gatgctgact   480
aggaaacagt tcgggctgct gtccttcttt ttcgccgtgc tgcacgctat ctacagcctg   540
tcctatccca tgaggcgctc ttaccgatat aagctgctga actgggctta ccagcaggtg   600
cagcagaaca aggaggacgc atggattgaa cacgatgtgt ggcggatgga aatctatgtg   660
tctctgggca ttgtcgggct ggccatcctg gctctgctgg cagtgaccag tatcccttct   720
gtcagtgact cactgacatg gcgcgagttt cactacattc agagcaagct gggaatcgtg   780
tccctgctgc tggcaccat ccatgcactg atttttgcct ggaataagtg gatcgatatc   840
aagcagttcg tgtggtatac tcccctacc tttatgattg ccgtcttcct gcccatcgtg   900
gtcctgattt ttaagtccat cctgttcctg ccttgtctgc gaaagaaaat cctgaaaatc   960
cgacatgggt gggaagacgt gacaaaaatc aataagaccg aaatctcaag ccagctgtga  1020
taa                                                                1023

<210> SEQ ID NO 10
<211> LENGTH: 339
<212> TYPE: PRT

<213> ORGANISM: Artificial Sequence
<220> FEATURE:
<223> OTHER INFORMATION: STEAP antigen 1 amino acid consensus sequence

<400> SEQUENCE: 10

```
Met Glu Ser Arg Lys Asp Ile Thr Asn Gln Glu Glu Leu Trp Lys Met
1               5                   10                  15

Lys Pro Arg Arg Asn Leu Glu Glu Asp Asp Tyr Leu His Lys Asp Thr
            20                  25                  30

Gly Glu Thr Ser Met Leu Lys Arg Pro Val Leu Leu His Leu His Gln
        35                  40                  45

Thr Ala His Ala Asp Glu Phe Asp Cys Pro Ser Glu Leu Gln His Thr
    50                  55                  60

Gln Glu Leu Phe Pro Gln Trp His Leu Pro Ile Lys Ile Ala Ala Ile
65                  70                  75                  80

Ile Ala Ser Leu Thr Phe Leu Tyr Thr Leu Arg Glu Val Ile His
                85                  90                  95

Pro Leu Ala Thr Ser His Gln Gln Tyr Phe Tyr Lys Ile Pro Ile Leu
                100                 105                 110

Val Ile Asn Lys Val Leu Pro Met Val Ser Ile Thr Leu Leu Ala Leu
            115                 120                 125

Val Tyr Leu Pro Gly Val Ile Ala Ala Ile Val Gln Leu His Asn Gly
        130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Ala Val Leu His Ala
                165                 170                 175

Ile Tyr Ser Leu Ser Tyr Pro Met Arg Arg Ser Tyr Arg Tyr Lys Leu
                180                 185                 190

Leu Asn Trp Ala Tyr Gln Gln Val Gln Gln Asn Lys Glu Asp Ala Trp
            195                 200                 205

Ile Glu His Asp Val Trp Arg Met Glu Ile Tyr Val Ser Leu Gly Ile
        210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Ser Lys
                245                 250                 255

Leu Gly Ile Val Ser Leu Leu Leu Gly Thr Ile His Ala Leu Ile Phe
            260                 265                 270

Ala Trp Asn Lys Trp Ile Asp Ile Lys Gln Phe Val Trp Tyr Thr Pro
        275                 280                 285

Pro Thr Phe Met Ile Ala Val Phe Leu Pro Ile Val Val Leu Ile Phe
    290                 295                 300

Lys Ser Ile Leu Phe Leu Pro Cys Leu Arg Lys Lys Ile Leu Lys Ile
305                 310                 315                 320

Arg His Gly Trp Glu Asp Val Thr Lys Ile Asn Lys Thr Glu Ile Ser
                325                 330                 335

Ser Gln Leu
```

<210> SEQ ID NO 11
<211> LENGTH: 1074
<212> TYPE: DNA
<213> ORGANISM: Artificial Sequence
<220> FEATURE:
<223> OTHER INFORMATION: STEAP antigen 2 nucleic acid consensus sequence

```
<400> SEQUENCE: 11
atggactgga catggattct gtttctggtc gctgccgcaa cccgcgtgca ttcagagagc     60
cgcaaggaca tcacaaatca ggaagagctg tggaagatga accacggaga aaacctggag    120
gaagacgatt acctgcacaa ggacaccggc gaaacaagta tgctgaaaag accagtgctg    180
ctgcacctgc atcagactgc tcatgcagac gagtttgatt gccctctga  actgcagcac    240 acccaggagc tgttcccaca gtggcatctg cccatcaaga ttgccgctat cattgcttca    300
ctgacatttc tgtatactct gctgagagaa gtgatccacc ctctggccac cagccatcag    360
cagtacttct ataagatccc tattctggtc atcaacaagg tcctgccaat ggtgagcatc    420
acactgctgg ccctggtcta cctgcctggc gtgatcgcag ccattgtcca gctgcacaac    480
ggaacaaagt acaagaagtt cccacattgg ctggataagt ggatgctgac taggaaacag    540
ttcgggctgc tgtccttctt tttcgccgtg ctgcacgcta tctacagcct gtcctatccc    600
atgaggcgct cttaccgata taagctgctg aactgggctt accagcaggt gcagcagaac    660
aaggaggacg catggattga acacgatgtg tggcggatgg aaatctatgt gtctctgggc    720
attgtcgggc tggccatcct ggctctgctg cagtgaccgta tatcccttc tgtcagtgac     780 tcactgacat ggcgcgagtt tcactacatt cagagcaagc tgggaatcgt gtccctgctg    840
ctgggcacca tccatgcact gattttttgcc tggaataagt ggatcgatat caagcagttc    900
gtgtggtata ctccccctac ctttatgatt gccgtcttcc tgcccatcgt ggtcctgatt    960
tttaagtcca tcctgttcct gccttgtctg cgaaagaaaa tcctgaaaat ccgacatggg   1020
tgggaagacg tgacaaaaat caataagacc gaaatctcaa gccagctgtg ataa         1074

<210> SEQ ID NO 12
<211> LENGTH: 356
<212> TYPE: PRT
<213> ORGANISM: Artificial Sequence
<220> FEATURE:
<223> OTHER INFORMATION: STEAP antigen 2 amino acid consensus sequence

<400> SEQUENCE: 12

Met Asp Trp Thr Trp Ile Leu Phe Leu Val Ala Ala Thr Arg Val
1               5                   10                  15

His Ser Glu Ser Arg Lys Asp Ile Thr Asn Gln Glu Glu Leu Trp Lys
            20                  25                  30

Met Lys Pro Arg Arg Asn Leu Glu Glu Asp Asp Tyr Leu His Lys Asp
        35                  40                  45

Thr Gly Glu Thr Ser Met Leu Lys Arg Pro Val Leu Leu His Leu His
    50                  55                  60

Gln Thr Ala His Ala Asp Glu Phe Asp Cys Pro Ser Glu Leu Gln His
65                  70                  75                  80

Thr Gln Glu Leu Phe Pro Gln Trp His Leu Pro Ile Lys Ile Ala Ala
                85                  90                  95

Ile Ile Ala Ser Leu Thr Phe Leu Tyr Thr Leu Leu Arg Glu Val Ile
            100                 105                 110

His Pro Leu Ala Thr Ser His Gln Gln Tyr Phe Tyr Lys Ile Pro Ile
        115                 120                 125

Leu Val Ile Asn Lys Val Leu Pro Met Val Ser Ile Thr Leu Leu Ala
    130                 135                 140

Leu Val Tyr Leu Pro Gly Val Ile Ala Ala Ile Val Gln Leu His Asn
145                 150                 155                 160

Gly Thr Lys Tyr Lys Lys Phe Pro His Trp Leu Asp Lys Trp Met Leu
```

```
                165                 170                 175
Thr Arg Lys Gln Phe Gly Leu Leu Ser Phe Phe Phe Ala Val Leu His
            180                 185                 190

Ala Ile Tyr Ser Leu Ser Tyr Pro Met Arg Arg Ser Tyr Arg Tyr Lys
            195                 200                 205

Leu Leu Asn Trp Ala Tyr Gln Gln Val Gln Gln Asn Lys Glu Asp Ala
            210                 215                 220

Trp Ile Glu His Asp Val Trp Arg Met Glu Ile Tyr Val Ser Leu Gly
225                 230                 235                 240

Ile Val Gly Leu Ala Ile Leu Ala Leu Leu Ala Val Thr Ser Ile Pro
                245                 250                 255

Ser Val Ser Asp Ser Leu Thr Trp Arg Glu Phe His Tyr Ile Gln Ser
                260                 265                 270

Lys Leu Gly Ile Val Ser Leu Leu Leu Gly Thr Ile His Ala Leu Ile
                275                 280                 285

Phe Ala Trp Asn Lys Trp Ile Asp Ile Lys Gln Phe Val Trp Tyr Thr
            290                 295                 300

Pro Pro Thr Phe Met Ile Ala Val Phe Leu Pro Ile Val Val Leu Ile
305                 310                 315                 320

Phe Lys Ser Ile Leu Phe Leu Pro Cys Leu Arg Lys Lys Ile Leu Lys
                325                 330                 335

Ile Arg His Gly Trp Glu Asp Val Thr Lys Ile Asn Lys Thr Glu Ile
                340                 345                 350

Ser Ser Gln Leu
        355

<210> SEQ ID NO 13
<211> LENGTH: 399
<212> TYPE: DNA
<213> ORGANISM: Artificial Sequence
<220> FEATURE:
<223> OTHER INFORMATION: PSCA antigen nucleic acid consensus sequence

<400> SEQUENCE: 13
atggactgga catggattct gtttctggtc gccgccgcaa cccgcgtgca ttctgctggc      60
ctggcactgc agcctggaac cgccctgctg tgctactctt gtaaggccca ggtgagtaac     120
gaggactgcc tgcaggtcga aaattgtact cagctgggag agcagtgctg gaccgcacgg     180
atcagagcag tgggactgct gacagtcatt agcaaagggg ctccctgaa ctgtgtggac      240
gatagccagg attactatgt cggaaagaaa aacatcacct gctgtgacac agatctgtgt     300
aatgcttctg gcgcccacgc tctgcagccc gcagccgcta ttctggctct gctgcccgct     360
ctgggactgc tgctgtgggg acccggacag ctgtgataa                            399

<210> SEQ ID NO 14
<211> LENGTH: 131
<212> TYPE: PRT
<213> ORGANISM: Artificial Sequence
<220> FEATURE:
<223> OTHER INFORMATION: PSCA antigen amino acid consensus sequence

<400> SEQUENCE: 14

Met Asp Trp Thr Trp Ile Leu Phe Leu Val Ala Ala Ala Thr Arg Val
1               5                   10                  15

His Ser Ala Gly Leu Ala Leu Gln Pro Gly Thr Ala Leu Leu Cys Tyr
            20                  25                  30

Ser Cys Lys Ala Gln Val Ser Asn Glu Asp Cys Leu Gln Val Glu Asn
```

```
            35                  40                  45
Cys Thr Gln Leu Gly Glu Gln Cys Trp Thr Ala Arg Ile Arg Ala Val
     50                  55                  60

Gly Leu Leu Thr Val Ile Ser Lys Gly Cys Ser Leu Asn Cys Val Asp
 65                  70                  75                  80

Asp Ser Gln Asp Tyr Tyr Val Gly Lys Lys Asn Ile Thr Cys Cys Asp
                 85                  90                  95

Thr Asp Leu Cys Asn Ala Ser Gly Ala His Ala Leu Gln Pro Ala Ala
            100                 105                 110

Ala Ile Leu Ala Leu Leu Pro Ala Leu Gly Leu Leu Leu Trp Gly Pro
        115                 120                 125

Gly Gln Leu
        130

<210> SEQ ID NO 15
<211> LENGTH: 54
<212> TYPE: DNA
<213> ORGANISM: Artificial Sequence
<220> FEATURE:
<223> OTHER INFORMATION: IgE leader nucleic acid sequence

<400> SEQUENCE: 15
atggactgga catggattct gtttctggtc gctgccgcaa cccgcgtgca ttca          54

<210> SEQ ID NO 16
<211> LENGTH: 18
<212> TYPE: PRT
<213> ORGANISM: Artificial Sequence
<220> FEATURE:
<223> OTHER INFORMATION: IgE leader amino acid sequence

<400> SEQUENCE: 16

Met Asp Trp Thr Trp Ile Leu Phe Leu Val Ala Ala Thr Arg Val
 1               5                  10                  15

His Ser

<210> SEQ ID NO 17
<211> LENGTH: 261
<212> TYPE: PRT
<213> ORGANISM: Homo sapiens

<400> SEQUENCE: 17

Met Trp Val Pro Val Val Phe Leu Thr Leu Ser Val Thr Trp Ile Gly
 1               5                  10                  15

Ala Ala Pro Leu Ile Leu Ser Arg Ile Val Gly Gly Trp Glu Cys Glu
             20                  25                  30

Lys His Ser Gln Pro Trp Gln Val Leu Val Ala Ser Arg Gly Arg Ala
         35                  40                  45

Val Cys Gly Gly Val Leu Val His Pro Gln Trp Val Leu Thr Ala Ala
     50                  55                  60

His Cys Ile Arg Asn Lys Ser Val Ile Leu Leu Gly Arg His Ser Leu
 65                  70                  75                  80

Phe His Pro Glu Asp Thr Gly Gln Val Phe Gln Val Ser His Ser Phe
                 85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125
```

Pro Ala Glu Leu Thr Asp Ala Val Lys Val Met Asp Leu Pro Thr Gln
130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
        195                 200                 205

Cys Ser Gly Asp Ser Gly Gly Pro Leu Val Cys Asn Gly Val Leu Gln
210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260

<210> SEQ ID NO 18
<211> LENGTH: 262
<212> TYPE: PRT
<213> ORGANISM: Homo sapiens

<400> SEQUENCE: 18

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
                20                  25                  30

Lys His Ser Gln Pro Trp Gln Val Leu Val Ala Ser Arg Gly Arg Ala
            35                  40                  45

Val Cys Gly Gly Val Leu Val His Pro Gln Trp Val Leu Thr Ala Ala
        50                  55                  60

His Cys Ile Arg Lys Cys Lys Ser Val Ile Leu Leu Gly Arg His Ser
65                  70                  75                  80

Leu Phe His Pro Glu Asp Thr Gly Gln Val Phe Gln Val Ser His Ser
                85                  90                  95

Phe Pro His Pro Leu Tyr Asp Met Ser Leu Leu Lys Asn Arg Phe Leu
            100                 105                 110

Arg Pro Gly Asp Asp Ser Ser His Asp Leu Met Leu Leu Arg Leu Ser
        115                 120                 125

Glu Pro Ala Glu Leu Thr Asp Ala Val Lys Val Met Asp Leu Pro Thr
130                 135                 140

Gln Glu Pro Ala Leu Gly Thr Thr Cys Tyr Ala Ser Gly Trp Gly Ser
145                 150                 155                 160

Ile Glu Pro Glu Glu Phe Leu Thr Pro Lys Lys Leu Gln Cys Val Asp
                165                 170                 175

Leu His Val Ile Ser Asn Asp Val Cys Ala Gln Val His Pro Gln Lys
            180                 185                 190

Val Thr Lys Phe Met Leu Cys Ala Gly Arg Trp Thr Gly Gly Lys Ser
        195                 200                 205

Thr Cys Ser Gly Asp Ser Gly Gly Pro Leu Val Cys Asn Gly Val Leu
210                 215                 220

Gln Gly Ile Thr Ser Trp Gly Ser Glu Pro Cys Ala Leu Pro Glu Arg
225                 230                 235                 240

Pro Ser Leu Tyr Thr Lys Val His Tyr Arg Lys Trp Ile Lys Asp
            245                 250                 255

Thr Ile Val Ala Asn Pro
            260

<210> SEQ ID NO 19
<211> LENGTH: 261
<212> TYPE: PRT
<213> ORGANISM: Macaca fascicularis

<400> SEQUENCE: 19

Met Trp Val Leu Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser His Gly Arg Ala
        35                  40                  45

Val Cys Gly Gly Val Leu Val His Pro Gln Trp Val Leu Thr Ala Ala
    50                  55                  60

His Cys Ile Arg Ser His Ser Val Ile Leu Leu Gly Arg His Asn Pro
65                  70                  75                  80

Tyr Tyr Pro Glu Asp Thr Gly Gln Val Phe Gln Val Ser His Ser Phe
                85                  90                  95

Pro His Pro Leu Tyr Asn Met Ser Leu Leu Lys Asn Arg Tyr Leu Gly
            100                 105                 110

Pro Gly Asp Asp Ser Ser His Asp Leu Met Leu Leu Arg Leu Ser Glu
        115                 120                 125

Pro Ala Glu Ile Thr Asp Ala Val Gln Val Leu Asp Leu Pro Thr Trp
    130                 135                 140

Glu Pro Glu Leu Gly Thr Thr Cys Tyr Ala Ser Gly Trp Gly Ser Ile
145                 150                 155                 160

Glu Pro Glu Glu His Leu Thr Pro Lys Lys Leu Gln Cys Val Asp Leu
                165                 170                 175

His Ile Ile Ser Asn Asp Val Cys Ala Gln Val His Ser Gln Lys Val
            180                 185                 190

Thr Lys Phe Met Leu Cys Ala Gly Ser Trp Met Gly Gly Lys Ser Thr
        195                 200                 205

Cys Ser Gly Asp Ser Gly Gly Pro Leu Val Cys Asp Gly Val Leu Gln
    210                 215                 220

Gly Ile Thr Ser Trp Gly Ser Gln Pro Cys Ala Leu Pro Arg Arg Pro
225                 230                 235                 240

Ser Leu Tyr Thr Lys Val Val Arg Tyr Arg Lys Trp Ile Gln Asp Thr
                245                 250                 255

Ile Met Ala Asn Pro
            260

<210> SEQ ID NO 20
<211> LENGTH: 261
<212> TYPE: PRT
<213> ORGANISM: Macaca mulatta

<400> SEQUENCE: 20

Met Trp Val Leu Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

```
Lys His Ser Gln Pro Trp Gln Val Leu Val Ala Ser Arg Gly Arg Ala
            35                  40                  45

Val Cys Gly Gly Val Leu Val His Pro Gln Trp Val Leu Thr Ala Ala
 50                  55                  60

His Cys Ile Arg Ser Asn Ser Val Ile Leu Leu Gly Arg His Asn Pro
 65                  70                  75                  80

Tyr Tyr Pro Glu Asp Thr Gly Gln Val Phe Gln Val Ser His Ser Phe
                 85                  90                  95

Pro His Pro Leu Tyr Asn Met Ser Leu Leu Lys Asn Arg Tyr Leu Gly
                100                 105                 110

Pro Gly Asp Asp Ser Ser His Asp Leu Met Leu Leu Arg Leu Ser Glu
            115                 120                 125

Pro Ala Glu Ile Thr Asp Ala Val Gln Val Leu Asp Leu Pro Thr Trp
130                 135                 140

Glu Pro Glu Leu Gly Thr Thr Cys Tyr Ala Ser Gly Trp Gly Ser Ile
145                 150                 155                 160

Glu Pro Glu Glu His Leu Thr Pro Lys Lys Leu Gln Cys Val Asp Leu
                165                 170                 175

His Ile Ile Ser Asn Asp Val Cys Ala Gln Val His Ser Gln Lys Val
            180                 185                 190

Thr Lys Phe Met Leu Cys Ala Gly Ser Trp Met Gly Gly Lys Ser Thr
            195                 200                 205

Cys Ser Gly Asp Ser Gly Gly Pro Leu Val Cys Asp Gly Val Leu Gln
210                 215                 220

Gly Ile Thr Ser Trp Gly Ser Gln Pro Cys Ala Leu Pro Arg Arg Pro
225                 230                 235                 240

Ser Leu Tyr Thr Lys Val Val Arg Tyr Arg Lys Trp Ile Gln Asp Thr
                245                 250                 255

Ile Met Ala Asn Pro
            260

<210> SEQ ID NO 21
<211> LENGTH: 244
<212> TYPE: PRT
<213> ORGANISM: Macaca mulatta

<400> SEQUENCE: 21

Ala Pro Leu Ile Leu Ser Arg Ile Val Gly Gly Trp Glu Cys Glu Lys
 1               5                  10                  15

His Ser Gln Pro Trp Gln Val Leu Val Ala Ser Arg Gly Arg Ala Val
                 20                  25                  30

Cys Gly Gly Val Leu Val His Pro Gln Trp Val Leu Thr Ala Ala His
             35                  40                  45

Cys Ile Arg Ser Asn Ser Val Ile Leu Leu Gly Arg His Asn Pro Tyr
 50                  55                  60

Tyr Pro Glu Asp Thr Gly Gln Val Phe Gln Val Ser His Ser Phe Pro
 65                  70                  75                  80

His Pro Leu Tyr Asn Met Ser Leu Leu Lys Asn Arg Tyr Leu Gly Pro
                 85                  90                  95

Gly Asp Asp Ser Ser His Asp Leu Met Leu Leu Arg Leu Ser Glu Pro
            100                 105                 110

Ala Glu Ile Thr Asp Ala Val Gln Val Leu Asp Leu Pro Thr Trp Glu
            115                 120                 125

Pro Glu Leu Gly Thr Thr Cys Tyr Ala Ser Gly Trp Gly Ser Ile Glu
```

```
            130                 135                 140
Pro Glu Glu His Leu Thr Pro Lys Lys Leu Gln Cys Val Asp Leu His
145                 150                 155                 160

Ile Ile Ser Asn Asp Val Cys Ala Gln Val His Ser Gln Lys Val Thr
            165                 170                 175

Lys Phe Met Leu Cys Ala Gly Ser Trp Met Gly Lys Ser Thr Cys
                180                 185                 190

Ser Gly Asp Ser Gly Gly Pro Leu Val Cys Asp Gly Val Leu Gln Gly
            195                 200                 205

Ile Thr Ser Trp Gly Ser Gln Pro Cys Ala Leu Pro Arg Arg Pro Ser
        210                 215                 220

Leu Tyr Thr Lys Val Val Arg Tyr Arg Lys Trp Ile Gln Asp Thr Ile
225                 230                 235                 240

Met Ala Asn Pro

<210> SEQ ID NO 22
<211> LENGTH: 750
<212> TYPE: PRT
<213> ORGANISM: Homo sapiens

<400> SEQUENCE: 22

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
                245                 250                 255

Asn Ile Leu Asn Leu Asn Gly Ala Gly Asp Pro Leu Thr Pro Gly Tyr
```

```
              260                 265                 270
Pro Ala Asn Glu Tyr Ala Tyr Arg Arg Gly Ile Ala Glu Ala Val Gly
            275                 280                 285
Leu Pro Ser Ile Pro Val His Pro Ile Gly Tyr Tyr Asp Ala Gln Lys
            290                 295                 300
Leu Leu Glu Lys Met Gly Gly Ser Ala Pro Pro Asp Ser Ser Trp Arg
305                 310                 315                 320
Gly Ser Leu Lys Val Pro Tyr Asn Val Gly Pro Gly Phe Thr Gly Asn
                325                 330                 335
Phe Ser Thr Gln Lys Val Lys Met His Ile His Ser Thr Asn Glu Val
                340                 345                 350
Thr Arg Ile Tyr Asn Val Ile Gly Thr Leu Arg Gly Ala Val Glu Pro
            355                 360                 365
Asp Arg Tyr Val Ile Leu Gly Gly His Arg Asp Ser Trp Val Phe Gly
            370                 375                 380
Gly Ile Asp Pro Gln Ser Gly Ala Ala Val Val His Glu Ile Val Arg
385                 390                 395                 400
Ser Phe Gly Thr Leu Lys Lys Glu Gly Trp Arg Pro Arg Arg Thr Ile
                405                 410                 415
Leu Phe Ala Ser Trp Asp Ala Glu Glu Phe Gly Leu Leu Gly Ser Thr
                420                 425                 430
Glu Trp Ala Glu Glu Asn Ser Arg Leu Leu Gln Glu Arg Gly Val Ala
            435                 440                 445
Tyr Ile Asn Ala Asp Ser Ser Ile Glu Gly Asn Tyr Thr Leu Arg Val
            450                 455                 460
Asp Cys Thr Pro Leu Met Tyr Ser Leu Val His Asn Leu Thr Lys Glu
465                 470                 475                 480
Leu Lys Ser Pro Asp Glu Gly Phe Glu Gly Lys Ser Leu Tyr Glu Ser
                485                 490                 495
Trp Thr Lys Lys Ser Pro Ser Pro Glu Phe Ser Gly Met Pro Arg Ile
                500                 505                 510
Ser Lys Leu Gly Ser Gly Asn Asp Phe Glu Val Phe Phe Gln Arg Leu
            515                 520                 525
Gly Ile Ala Ser Gly Arg Ala Arg Tyr Thr Lys Asn Trp Glu Thr Asn
            530                 535                 540
Lys Phe Ser Gly Tyr Pro Leu Tyr His Ser Val Tyr Glu Thr Tyr Glu
545                 550                 555                 560
Leu Val Glu Lys Phe Tyr Asp Pro Met Phe Lys Tyr His Leu Thr Val
                565                 570                 575
Ala Gln Val Arg Gly Gly Met Val Phe Glu Leu Ala Asn Ser Ile Val
            580                 585                 590
Leu Pro Phe Asp Cys Arg Asp Tyr Ala Val Val Leu Arg Lys Tyr Ala
            595                 600                 605
Asp Lys Ile Tyr Ser Ile Ser Met Lys His Pro Gln Glu Met Lys Thr
            610                 615                 620
Tyr Ser Val Ser Phe Asp Ser Leu Phe Ser Ala Val Lys Asn Phe Thr
625                 630                 635                 640
Glu Ile Ala Ser Lys Phe Ser Glu Arg Leu Gln Asp Phe Asp Lys Ser
                645                 650                 655
Asn Pro Ile Val Leu Arg Met Met Asn Asp Gln Leu Met Phe Leu Glu
            660                 665                 670
Arg Ala Phe Ile Asp Pro Leu Gly Leu Pro Asp Arg Pro Phe Tyr Arg
            675                 680                 685
```

```
His Val Ile Tyr Ala Pro Ser Ser His Asn Lys Tyr Ala Gly Glu Ser
        690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
                740                 745                 750

<210> SEQ ID NO 23
<211> LENGTH: 749
<212> TYPE: PRT
<213> ORGANISM: Homo sapiens

<400> SEQUENCE: 23

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
                20                  25                  30

Phe Leu Leu Gly Phe Leu Phe Gly Trp Phe Ile Lys Ser Ser Asn Glu
            35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu His Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
                100                 105                 110

Tyr Asp Val Leu Leu Ser Tyr Pro Asn Lys Thr His Pro Asn Tyr Ile
            115                 120                 125

Ser Ile Ile Asn Glu Asp Gly Asn Glu Ile Phe Asn Thr Ser Leu Phe
    130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
                180                 185                 190

Lys Ile Asn Cys Ser Gly Lys Ile Val Ile Ala Arg Tyr Gly Lys Val
            195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
                245                 250                 255

Asn Ile Leu Asn Leu Asn Gly Ala Gly Asp Pro Leu Thr Pro Gly Tyr
                260                 265                 270

Pro Ala Asn Glu Tyr Ala Tyr Arg Arg Gly Ile Ala Glu Ala Val Gly
            275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
```

```
            305                 310                 315                 320
        Gly Ser Leu Lys Val Pro Tyr Asn Val Gly Pro Gly Phe Thr Gly Asn
                        325                 330                 335

Phe Ser Thr Gln Lys Val Lys Met His Ile His Ser Thr Asn Glu Val
                        340                 345                 350

Thr Arg Ile Tyr Asn Val Ile Gly Thr Leu Arg Gly Ala Val Glu Pro
                        355                 360                 365

Asp Arg Tyr Val Ile Leu Gly Gly His Arg Asp Ser Trp Val Phe Gly
                        370                 375                 380

Gly Ile Asp Pro Gln Ser Gly Ala Ala Val Val His Glu Ile Val Arg
        385                 390                 395                 400

Ser Phe Gly Thr Leu Lys Lys Glu Gly Trp Arg Pro Arg Arg Thr Ile
                        405                 410                 415

Leu Phe Ala Ser Trp Asp Ala Glu Glu Phe Gly Leu Leu Gly Ser Thr
                        420                 425                 430

Glu Trp Ala Glu Glu Asn Ser Arg Leu Leu Gln Glu Arg Gly Val Ala
                        435                 440                 445

Tyr Ile Asn Ala Asp Ser Ser Ile Glu Gly Asn Tyr Thr Leu Arg Val
                        450                 455                 460

Asp Cys Thr Pro Leu Met Tyr Ser Leu Val His Asn Leu Thr Lys Glu
        465                 470                 475                 480

Leu Lys Ser Pro Asp Glu Gly Phe Glu Gly Lys Ser Leu Tyr Glu Ser
                        485                 490                 495

Trp Thr Lys Lys Ser Pro Ser Pro Glu Phe Ser Gly Met Pro Arg Ile
                        500                 505                 510

Ser Lys Leu Gly Ser Gly Asn Asp Phe Glu Val Phe Phe Gln Arg Leu
                        515                 520                 525

Gly Ile Ala Ser Gly Arg Ala Arg Tyr Thr Lys Asn Trp Glu Thr Asn
                        530                 535                 540

Phe Ser Gly Tyr Pro Leu Tyr His Ser Val Tyr Glu Thr Tyr Glu Leu
        545                 550                 555                 560

Val Glu Lys Phe Tyr Asp Pro Met Phe Lys Tyr His Leu Thr Val Ala
                        565                 570                 575

Gln Val Arg Gly Gly Met Val Phe Glu Leu Ala Asn Ser Ile Val Leu
                        580                 585                 590

Pro Phe Asp Cys Arg Asp Tyr Ala Val Val Leu Arg Lys Tyr Ala Asp
                        595                 600                 605

Lys Ile Tyr Ser Ile Ser Met Lys His Pro Gln Glu Met Lys Thr Tyr
                        610                 615                 620

Ser Val Ser Phe Asp Ser Leu Phe Ser Ala Val Lys Asn Phe Thr Glu
        625                 630                 635                 640

Ile Ala Ser Lys Phe Ser Glu Arg Leu Gln Asp Phe Asp Lys Ser Asn
                        645                 650                 655

Pro Ile Val Leu Arg Met Met Asn Asp Gln Leu Met Phe Leu Glu Arg
                        660                 665                 670

Ala Phe Ile Asp Pro Leu Gly Leu Pro Asp Arg Pro Phe Tyr Arg His
                        675                 680                 685

Val Ile Tyr Ala Pro Ser Ser His Asn Lys Tyr Ala Gly Glu Ser Phe
                        690                 695                 700

Pro Gly Ile Tyr Asp Ala Leu Phe Asp Ile Glu Ser Lys Val Asp Pro
        705                 710                 715                 720

Ser Lys Ala Trp Gly Glu Val Lys Arg Gln Ile Tyr Val Ala Ala Phe
                        725                 730                 735
```

Thr Val Gln Ala Ala Ala Glu Thr Leu Ser Glu Val Ala
            740                 745

<210> SEQ ID NO 24
<211> LENGTH: 735
<212> TYPE: PRT
<213> ORGANISM: Macaca mulatta

<400> SEQUENCE: 24

Met Ile Ala Gly Ser Ser Tyr Pro Leu Leu Ala Ala Tyr Ala Cys
1               5                   10                  15

Thr Gly Cys Leu Ala Glu Arg Leu Gly Trp Phe Ile Lys Ser Ser
                20                  25                  30

Glu Ala Thr Asn Ile Thr Pro Lys His Asn Met Lys Ala Phe Leu Asp
                35                  40                  45

Glu Leu Lys Ala Glu Asn Ile Lys Lys Phe Leu His Asn Phe Thr Gln
            50                  55                  60

Ile Pro His Leu Ala Gly Thr Glu Gln Asn Phe Gln Leu Ala Lys Gln
65                  70                  75                  80

Ile Gln Ser Gln Trp Lys Glu Phe Gly Leu Asp Ser Val Glu Leu Thr
                85                  90                  95

His Tyr Asp Val Leu Leu Ser Tyr Pro Asn Lys Thr His Pro Asn Tyr
                100                 105                 110

Ile Ser Ile Ile Asn Glu Asp Gly Asn Glu Ile Phe Asn Thr Ser Leu
            115                 120                 125

Phe Glu Pro Pro Pro Ala Gly Tyr Glu Asn Val Ser Asp Ile Val Pro
130                 135                 140

Pro Phe Ser Ala Phe Ser Pro Gln Gly Met Pro Glu Gly Asp Leu Val
145                 150                 155                 160

Tyr Val Asn Tyr Ala Arg Thr Glu Asp Phe Phe Lys Leu Glu Arg Asp
                165                 170                 175

Met Lys Ile Asn Cys Ser Gly Lys Ile Val Ile Ala Arg Tyr Gly Lys
            180                 185                 190

Val Phe Arg Gly Asn Lys Val Lys Asn Ala Gln Leu Ala Gly Ala Thr
        195                 200                 205

Gly Val Ile Leu Tyr Ser Asp Pro Ala Asp Tyr Phe Ala Pro Gly Val
    210                 215                 220

Lys Ser Tyr Pro Asp Gly Trp Asn Leu Pro Gly Gly Gly Val Gln Arg
225                 230                 235                 240

Gly Asn Ile Leu Asn Leu Asn Gly Ala Gly Asp Pro Leu Thr Pro Gly
                245                 250                 255

Tyr Pro Ala Asn Glu Tyr Ala Tyr Arg Arg Gly Met Ala Glu Ala Val
            260                 265                 270

Gly Leu Pro Ser Ile Pro Val His Pro Ile Gly Tyr Tyr Asp Ala Gln
        275                 280                 285

Lys Leu Leu Glu Lys Met Gly Gly Ser Ala Ser Pro Asp Ser Ser Trp
    290                 295                 300

Arg Gly Ser Leu Lys Val Pro Tyr Asn Val Gly Pro Gly Phe Thr Gly
305                 310                 315                 320

Asn Phe Ser Thr Gln Lys Val Lys Met His Ile His Ser Thr Ser Glu
                325                 330                 335

Val Thr Arg Ile Tyr Asn Val Ile Gly Thr Leu Arg Gly Ala Val Glu
            340                 345                 350

Pro Asp Arg Tyr Val Ile Leu Gly Gly His Arg Asp Ser Trp Val Phe

```
                    355                 360                 365
Gly Gly Ile Asp Pro Gln Ser Gly Ala Ala Val Val His Glu Ile Val
        370                 375                 380
Arg Ser Phe Gly Thr Leu Lys Lys Glu Gly Trp Pro Arg Arg Thr
385                 390                 395                 400
Ile Leu Phe Ala Ser Trp Asp Ala Glu Phe Gly Leu Leu Gly Ser
                405                 410                 415
Thr Glu Trp Ala Glu Glu Asn Ser Arg Leu Leu Gln Glu Arg Gly Val
                420                 425                 430
Ala Tyr Ile Asn Ala Asp Ser Ser Ile Glu Gly Asn Tyr Thr Leu Arg
            435                 440                 445
Val Asp Cys Thr Pro Leu Met Tyr Ser Leu Val Tyr Asn Leu Thr Lys
    450                 455                 460
Glu Leu Glu Ser Pro Asp Glu Gly Phe Glu Gly Lys Ser Leu Tyr Glu
465                 470                 475                 480
Ser Trp Thr Lys Lys Ser Pro Ser Pro Glu Phe Ser Gly Met Pro Arg
                485                 490                 495
Ile Ser Lys Leu Gly Ser Gly Asn Asp Phe Glu Val Phe Phe Gln Arg
                500                 505                 510
Leu Gly Ile Ala Ser Gly Arg Ala Arg Tyr Thr Lys Asn Trp Glu Thr
            515                 520                 525
Asn Lys Phe Ser Ser Tyr Pro Leu Tyr His Ser Val Tyr Glu Thr Tyr
            530                 535                 540
Glu Leu Val Glu Lys Phe Tyr Asp Pro Met Phe Lys Tyr His Leu Thr
545                 550                 555                 560
Val Ala Gln Val Arg Gly Gly Met Val Phe Glu Leu Ala Asn Ser Val
                565                 570                 575
Val Leu Pro Phe Asp Cys Arg Asp Tyr Ala Val Val Leu Arg Lys Tyr
                580                 585                 590
Ala Asp Lys Ile Tyr Asn Ile Ser Met Lys His Pro Gln Glu Met Lys
            595                 600                 605
Thr Tyr Ser Val Ser Phe Asp Ser Leu Phe Ser Ala Val Lys Asn Phe
    610                 615                 620
Thr Glu Ile Ala Ser Lys Phe Ser Glu Arg Leu Arg Asp Phe Asp Lys
625                 630                 635                 640
Ser Asn Pro Ile Leu Leu Arg Met Met Asn Asp Gln Leu Met Phe Leu
                645                 650                 655
Glu Arg Ala Phe Ile Asp Pro Leu Gly Leu Pro Asp Arg Pro Phe Tyr
                660                 665                 670
Arg His Val Ile Tyr Ala Pro Ser His Asn Lys Tyr Ala Gly Glu
        675                 680                 685
Ser Phe Pro Gly Ile Tyr Asp Ala Leu Phe Asp Ile Glu Ser Lys Val
    690                 695                 700
Asp Pro Ser Gln Ala Trp Gly Glu Val Lys Arg Gln Ile Ser Ile Ala
705                 710                 715                 720
Thr Phe Thr Val Gln Ala Ala Glu Thr Leu Ser Glu Val Ala
                725                 730                 735

<210> SEQ ID NO 25
<211> LENGTH: 704
<212> TYPE: PRT
<213> ORGANISM: Macaca mulatta

<400> SEQUENCE: 25
```

-continued

```
Met Ile Ala Gly Ser Ser Tyr Pro Leu Leu Ala Ala Tyr Ala Cys
1               5                   10                  15

Thr Gly Cys Leu Ala Glu Arg Leu Gly Trp Phe Ile Lys Ser Ser Ser
            20                  25                  30

Glu Ala Thr Asn Ile Thr Pro Lys His Asn Met Lys Ala Phe Leu Asp
            35                  40                  45

Glu Leu Lys Ala Glu Asn Ile Lys Lys Phe Leu His Asn Phe Thr Gln
50                  55                  60

Ile Pro His Leu Ala Gly Thr Glu Gln Asn Phe Gln Leu Ala Lys Gln
65                  70                  75                  80

Ile Gln Ser Gln Trp Lys Glu Phe Gly Leu Asp Ser Val Glu Leu Thr
                85                  90                  95

His Tyr Asp Val Leu Leu Ser Tyr Pro Asn Lys Thr His Pro Asn Tyr
                100                 105                 110

Ile Ser Ile Ile Asn Glu Asp Gly Asn Glu Ile Phe Asn Thr Ser Leu
                115                 120                 125

Phe Glu Pro Pro Ala Gly Tyr Glu Asn Val Ser Asp Ile Val Pro
                130                 135                 140

Pro Phe Ser Ala Phe Ser Pro Gln Gly Met Pro Glu Gly Asp Leu Val
145                 150                 155                 160

Tyr Val Asn Tyr Ala Arg Thr Glu Asp Phe Phe Lys Leu Glu Arg Asp
                165                 170                 175

Met Lys Ile Asn Cys Ser Gly Lys Ile Val Ile Ala Arg Tyr Gly Lys
                180                 185                 190

Val Phe Arg Gly Asn Lys Val Lys Asn Ala Gln Leu Ala Gly Ala Thr
                195                 200                 205

Gly Val Ile Leu Tyr Ser Asp Pro Ala Asp Tyr Phe Ala Pro Gly Val
                210                 215                 220

Lys Ser Tyr Pro Asp Gly Trp Asn Leu Pro Gly Gly Val Gln Arg
225                 230                 235                 240

Gly Asn Ile Leu Asn Leu Asn Gly Ala Gly Asp Pro Leu Thr Pro Gly
                245                 250                 255

Tyr Pro Ala Asn Glu Tyr Ala Tyr Arg Arg Gly Met Ala Glu Ala Val
                260                 265                 270

Gly Leu Pro Ser Ile Pro Val His Pro Ile Gly Tyr Tyr Asp Ala Gln
                275                 280                 285

Lys Leu Leu Glu Lys Met Gly Gly Ser Ala Ser Pro Asp Ser Ser Trp
290                 295                 300

Arg Gly Ser Leu Lys Val Pro Tyr Asn Val Gly Pro Gly Phe Thr Gly
305                 310                 315                 320

Asn Phe Ser Thr Gln Lys Val Lys Met His Ile His Ser Thr Ser Glu
                325                 330                 335

Val Thr Arg Ile Tyr Asn Val Ile Gly Thr Leu Arg Gly Ala Val Glu
                340                 345                 350

Pro Asp Arg Tyr Val Ile Leu Gly Gly His Arg Asp Ser Trp Val Phe
                355                 360                 365

Gly Gly Ile Asp Pro Gln Ser Gly Ala Ala Val Val His Glu Ile Val
                370                 375                 380

Arg Ser Phe Gly Thr Leu Lys Lys Glu Gly Trp Arg Pro Arg Arg Thr
385                 390                 395                 400

Ile Leu Phe Ala Ser Trp Asp Ala Glu Glu Phe Gly Leu Leu Gly Ser
                405                 410                 415

Thr Glu Trp Ala Glu Glu Asn Ser Arg Leu Leu Gln Glu Arg Gly Val
```

```
            420                 425                 430
Ala Tyr Ile Asn Ala Asp Ser Ser Ile Glu Gly Asn Tyr Thr Leu Arg
            435                 440                 445
Val Asp Cys Thr Pro Leu Met Tyr Ser Leu Val Tyr Asn Leu Thr Lys
            450                 455                 460
Glu Leu Glu Ser Pro Asp Glu Gly Phe Glu Gly Lys Ser Leu Tyr Glu
465                 470                 475                 480
Ser Trp Thr Lys Lys Ser Pro Ser Pro Glu Phe Ser Gly Met Pro Arg
                    485                 490                 495
Ile Ser Lys Leu Gly Ser Gly Asn Asp Phe Glu Val Phe Phe Gln Arg
                500                 505                 510
Leu Gly Ile Ala Ser Gly Arg Ala Arg Tyr Thr Lys Asn Trp Glu Thr
            515                 520                 525
Asn Lys Phe Ser Ser Tyr Pro Leu Tyr His Ser Val Tyr Glu Thr Tyr
            530                 535                 540
Glu Leu Val Glu Lys Phe Tyr Asp Pro Met Phe Lys Tyr His Leu Thr
545                 550                 555                 560
Val Ala Gln Val Arg Gly Gly Met Val Phe Glu Leu Ala Asn Ser Val
                    565                 570                 575
Val Leu Pro Phe Asp Cys Arg Asp Tyr Ala Val Val Leu Arg Lys Tyr
                580                 585                 590
Ala Asp Lys Ile Tyr Asn Ile Ser Met Lys His Pro Gln Glu Met Lys
            595                 600                 605
Thr Tyr Ser Val Ser Phe Asp Ser Leu Phe Ser Ala Val Lys Asn Phe
            610                 615                 620
Thr Glu Ile Ala Ser Lys Phe Ser Glu Arg Leu Arg Asp Phe Asp Lys
625                 630                 635                 640
Ser Lys His Val Ile Tyr Ala Pro Ser Ser His Asn Lys Tyr Ala Gly
                    645                 650                 655
Glu Ser Phe Pro Gly Ile Tyr Asp Ala Leu Phe Asp Ile Glu Ser Lys
                660                 665                 670
Val Asp Pro Ser Gln Ala Trp Gly Glu Val Lys Arg Gln Ile Ser Ile
            675                 680                 685
Ala Thr Phe Thr Val Gln Ala Ala Glu Thr Leu Ser Glu Val Ala
            690                 695                 700

<210> SEQ ID NO 26
<211> LENGTH: 339
<212> TYPE: PRT
<213> ORGANISM: Homo sapiens

<400> SEQUENCE: 26

Met Glu Ser Arg Lys Asp Ile Thr Asn Gln Glu Glu Leu Trp Lys Met
1               5                   10                  15
Lys Pro Arg Arg Asn Leu Glu Glu Asp Asp Tyr Leu His Lys Asp Thr
                20                  25                  30
Gly Glu Thr Ser Met Leu Lys Arg Pro Val Leu Leu His Leu His Gln
            35                  40                  45
Thr Ala His Ala Asp Glu Phe Asp Cys Pro Ser Glu Leu Gln His Thr
            50                  55                  60
Gln Glu Leu Phe Pro Gln Trp His Leu Pro Ile Lys Ile Ala Ala Ile
65                  70                  75                  80
Ile Ala Ser Leu Thr Phe Leu Tyr Thr Leu Leu Arg Glu Val Ile His
                85                  90                  95
```

```
Pro Leu Ala Thr Ser His Gln Gln Tyr Phe Tyr Lys Ile Pro Ile Leu
            100                 105                 110

Val Ile Asn Lys Val Leu Pro Met Val Ser Ile Thr Leu Leu Ala Leu
        115                 120                 125

Val Tyr Leu Pro Gly Val Ile Ala Ala Ile Val Gln Leu His Asn Gly
    130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Ala Val Leu His Ala
                165                 170                 175

Ile Tyr Ser Leu Ser Tyr Pro Met Arg Arg Ser Tyr Arg Tyr Lys Leu
            180                 185                 190

Leu Asn Trp Ala Tyr Gln Gln Val Gln Gln Asn Lys Glu Asp Ala Trp
        195                 200                 205

Ile Glu His Asp Val Trp Arg Met Glu Ile Tyr Val Ser Leu Gly Ile
    210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Ser Lys
                245                 250                 255

Leu Gly Ile Val Ser Leu Leu Leu Gly Thr Ile His Ala Leu Ile Phe
            260                 265                 270

Ala Trp Asn Lys Trp Ile Asp Ile Lys Gln Phe Val Trp Tyr Thr Pro
        275                 280                 285

Pro Thr Phe Met Ile Ala Val Phe Leu Pro Ile Val Val Leu Ile Phe
    290                 295                 300

Lys Ser Ile Leu Phe Leu Pro Cys Leu Arg Lys Lys Ile Leu Lys Ile
305                 310                 315                 320

Arg His Gly Trp Glu Asp Val Thr Lys Ile Asn Lys Thr Glu Ile Cys
                325                 330                 335

Ser Gln Leu

<210> SEQ ID NO 27
<211> LENGTH: 339
<212> TYPE: PRT
<213> ORGANISM: Homo sapiens

<400> SEQUENCE: 27

Met Glu Ser Arg Lys Asp Ile Thr Asn Gln Glu Leu Trp Lys Met
1               5                   10                  15

Lys Pro Arg Arg Asn Leu Glu Glu Asp Asp Tyr Leu His Lys Asp Thr
                20                  25                  30

Gly Glu Thr Ser Met Leu Lys Arg Pro Val Leu Leu His Leu Gln Gln
            35                  40                  45

Thr Ala His Ala Asp Glu Phe Asp Cys Pro Ser Glu Leu Gln His Thr
    50                  55                  60

Gln Glu Leu Phe Pro Gln Trp His Leu Pro Ile Lys Ile Ala Ala Ile
65                  70                  75                  80

Ile Ala Ser Leu Thr Phe Leu Tyr Thr Leu Leu Arg Glu Val Ile His
                85                  90                  95

Pro Leu Ala Thr Ser His Gln Gln Tyr Phe Tyr Lys Ile Pro Ile Leu
            100                 105                 110

Val Ile Asn Lys Val Leu Pro Met Val Ser Ile Thr Leu Leu Ala Leu
        115                 120                 125
```

Val Tyr Leu Pro Gly Val Ile Ala Ala Ile Val Gln Leu His Asn Gly
130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Ala Val Leu His Ala
                165                 170                 175

Ile Tyr Ser Leu Ser Tyr Pro Met Arg Arg Ser Tyr Arg Tyr Lys Leu
                180                 185                 190

Leu Asn Trp Ala Tyr Gln Gln Val Gln Gln Asn Lys Glu Asp Ala Trp
            195                 200                 205

Ile Glu His Asp Val Trp Arg Met Glu Ile Tyr Val Ser Leu Gly Ile
210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Ser Lys
                245                 250                 255

Leu Gly Ile Val Ser Leu Leu Leu Gly Thr Ile His Ala Leu Ile Phe
            260                 265                 270

Ala Trp Asn Lys Trp Ile Asp Ile Lys Gln Phe Val Trp Tyr Thr Pro
            275                 280                 285

Pro Thr Phe Met Ile Ala Val Phe Leu Pro Ile Val Val Leu Ile Phe
            290                 295                 300

Lys Ser Ile Leu Phe Leu Pro Cys Leu Arg Lys Lys Ile Leu Lys Ile
305                 310                 315                 320

Arg His Gly Trp Glu Asp Val Thr Lys Ile Asn Lys Thr Glu Ile Cys
                325                 330                 335

Ser Gln Leu

<210> SEQ ID NO 28
<211> LENGTH: 339
<212> TYPE: PRT
<213> ORGANISM: Macaca mulatta

<400> SEQUENCE: 28

Met Glu Ser Arg Lys Asp Ile Thr Asn Glu Glu Leu Trp Lys Met
1               5                   10                  15

Lys Pro Arg Arg Asn Leu Glu Glu Asp Asp Tyr Leu His Lys Asp Thr
                20                  25                  30

Gly Glu Thr Ser Met Leu Lys Arg Pro Val Leu Leu His Leu His Gln
            35                  40                  45

Thr Ala His Ala Asp Glu Phe Asp Cys Pro Ser Glu Leu Gln His Thr
50                  55                  60

Gln Glu Leu Phe Pro Gln Trp His Leu Pro Ile Lys Ile Ala Ala Ile
65                  70                  75                  80

Ile Ala Ser Leu Thr Phe Leu Tyr Thr Leu Leu Arg Glu Val Ile His
                85                  90                  95

Pro Leu Ala Thr Ser His Gln Gln Tyr Phe Tyr Lys Ile Pro Ile Leu
                100                 105                 110

Val Ile Asn Lys Val Leu Pro Met Val Ser Ile Thr Leu Leu Ala Leu
            115                 120                 125

Val Tyr Leu Pro Gly Val Ile Ala Ala Ile Val Gln Leu His Asn Gly
130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Ala Val Leu His Ala
                165                 170                 175

Ile Tyr Ser Leu Ser Tyr Pro Met Arg Arg Ser Tyr Arg Tyr Lys Leu
            180                 185                 190

Leu Asn Trp Ala Tyr Gln Gln Val Gln Gln Asn Lys Glu Asp Ala Trp
        195                 200                 205

Ile Glu His Asp Val Trp Arg Met Glu Ile Tyr Val Ser Leu Gly Ile
    210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Ser Lys
                245                 250                 255

Leu Gly Ile Val Ser Leu Leu Leu Ala Thr Ile His Ala Leu Ile Phe
            260                 265                 270

Ala Trp Asn Lys Trp Ile Asp Ile Lys Gln Phe Val Trp Tyr Thr Pro
        275                 280                 285

Pro Thr Phe Met Ile Ala Val Phe Leu Pro Val Val Leu Ile Phe
    290                 295                 300

Lys Ser Ile Leu Phe Leu Pro Cys Leu Arg Lys Lys Ile Leu Lys Ile
305                 310                 315                 320

Arg His Gly Trp Glu Asp Val Thr Lys Ile Asn Lys Met Glu Ile Ser
                325                 330                 335

Ser Gln Leu

<210> SEQ ID NO 29
<211> LENGTH: 259
<212> TYPE: PRT
<213> ORGANISM: Homo sapiens

<400> SEQUENCE: 29

Met Glu Ser Arg Lys Asp Ile Thr Asn Gln Glu Ile Trp Lys Met
1               5                   10                  15

Lys Pro Arg Arg Asn Leu Glu Asp Asn Asp Tyr Leu His Lys Asp Thr
            20                  25                  30

Gly Glu Thr Ser Met Leu Lys Arg Pro Val Leu Leu His Leu Gln Gln
        35                  40                  45

Thr Ala His Ala Asp Glu Phe Asp Cys Pro Ser Glu Leu Gln His Ala
    50                  55                  60

Gln Glu Leu Phe Pro Gln Trp His Leu Pro Ile Lys Ile Ala Ala Val
65                  70                  75                  80

Met Ala Ser Leu Thr Phe Leu Tyr Thr Leu Arg Glu Val Ile His
                85                  90                  95

Pro Leu Ala Thr Ser His Gln Gln Tyr Phe Tyr Lys Ile Pro Ile Leu
            100                 105                 110

Val Ile Asn Lys Val Leu Pro Met Val Ser Ile Thr Leu Leu Ala Leu
        115                 120                 125

Val Tyr Leu Pro Gly Val Ile Ala Ala Ile Val Gln Val His Asn Gly
    130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Leu Phe Phe Ala Val Leu His Ala
                165                 170                 175

Ile Tyr Thr Leu Ser Tyr Ala Met Arg Arg Ser Tyr Arg Tyr Lys Leu
            180                 185                 190

Leu Asn Trp Ala Tyr Gln Gln Val Gln Gln Asn Lys Glu Asp Ala Trp
            195                 200                 205

Ile Glu His Asp Val Trp Arg Met Glu Ile Tyr Val Ser Leu Gly Ile
        210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Arg Leu
                245                 250                 255

Leu Gln Glu

<210> SEQ ID NO 30
<211> LENGTH: 258
<212> TYPE: PRT
<213> ORGANISM: Homo sapiens

<400> SEQUENCE: 30

Met Glu Ser Arg Lys Asp Ile Thr Asn Gln Glu Ile Trp Lys Met
1               5                   10                  15

Lys Pro Arg Arg Asn Leu Glu Asp Asn Asp Tyr Leu His Lys Asp Thr
                20                  25                  30

Gly Glu Thr Ser Met Leu Lys Arg Pro Val Leu Leu His Leu Gln Gln
            35                  40                  45

Thr Ala His Ala Asp Glu Phe Asp Cys Pro Ser Glu Leu Gln His Ala
    50                  55                  60

Gln Glu Leu Phe Pro Gln Trp His Leu Pro Ile Lys Ile Ala Ala Val
65                  70                  75                  80

Met Ala Ser Leu Thr Phe Leu Tyr Thr Leu Leu Arg Glu Val Ile His
                85                  90                  95

Pro Leu Ala Thr Ser His Gln Gln Tyr Phe Tyr Lys Ile Pro Ile Leu
                100                 105                 110

Val Ile Asn Lys Val Leu Pro Met Val Ser Ile Thr Leu Leu Ala Leu
            115                 120                 125

Val Tyr Leu Pro Gly Val Ile Ala Ala Ile Val Gln Val His Asn Gly
130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Leu Phe Phe Ala Val Leu His Ala
                165                 170                 175

Ile Tyr Thr Leu Ser Tyr Ala Met Arg Arg Ser Tyr Arg Tyr Lys Leu
            180                 185                 190

Leu Asn Trp Ala Tyr Gln Gln Val Gln Gln Asn Lys Glu Asp Ala Trp
            195                 200                 205

Ile Glu His Asp Val Trp Arg Met Glu Ile Tyr Val Ser Leu Gly Ile
        210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Val Asn
                245                 250                 255

Asn Ile

<210> SEQ ID NO 31
<211> LENGTH: 114
<212> TYPE: PRT
<213> ORGANISM: Homo sapiens

<400> SEQUENCE: 31

```
Met Ala Gly Leu Ala Leu Gln Pro Gly Thr Ala Leu Leu Cys Tyr Ser
1               5                   10                  15

Cys Lys Ala Gln Val Ser Asn Glu Asp Cys Leu Gln Val Glu Asn Cys
                20                  25                  30

Thr Gln Leu Gly Glu Gln Cys Trp Thr Ala Arg Ile Arg Ala Val Gly
            35                  40                  45

Leu Leu Thr Val Ile Ser Lys Gly Cys Ser Leu Asn Cys Val Asp Asp
        50                  55                  60

Ser Gln Asp Tyr Tyr Val Gly Lys Lys Asn Ile Thr Cys Cys Asp Thr
65                  70                  75                  80

Asp Leu Cys Asn Ala Ser Gly Ala His Ala Leu Gln Pro Ala Ala Ala
                85                  90                  95

Ile Leu Ala Leu Leu Pro Ala Leu Gly Leu Leu Leu Trp Gly Pro Gly
            100                 105                 110

Gln Leu

<210> SEQ ID NO 32
<211> LENGTH: 9
<212> TYPE: PRT
<213> ORGANISM: Artificial Sequence
<220> FEATURE:
<223> OTHER INFORMATION: HA Tag amino acid sequence

<400> SEQUENCE: 32

Tyr Pro Tyr Asp Val Pro Asp Tyr Ala
1               5
```